US006379942B1

(12) United States Patent
Davis et al.

(10) Patent No.: US 6,379,942 B1
(45) Date of Patent: Apr. 30, 2002

(54) CHEMICALLY MODIFIED ENZYMES WITH MULTIPLE CHARGED VARIANTS

(75) Inventors: Benjamin G. Davis, Durham (GB); John Bryan Jones, Lakefield (CA); Richard R. Bott, Burlingame, CA (US)

(73) Assignee: Genencor International, Inc., Palo Alto, CA (US)

( * ) Notice: Subject to any disclaimer, the term of this patent is extended or adjusted under 35 U.S.C. 154(b) by 0 days.

(21) Appl. No.: 09/467,536

(22) Filed: Dec. 20, 1999

Related U.S. Application Data

(60) Provisional application No. 60/113,130, filed on Dec. 21, 1998.

(51) Int. Cl.[7] .............................. C12N 9/54; C11D 7/42
(52) U.S. Cl. ........................................ 435/221; 510/392
(58) Field of Search ................................. 435/221, 810; 510/392

(56) References Cited

U.S. PATENT DOCUMENTS

| | | | |
|---|---|---|---|
| 5,208,158 A | 5/1993 | Bech et al. | 435/219 |
| 5,244,791 A | 9/1993 | Estell | 435/68.1 |
| 5,316,935 A | 5/1994 | Arnold et al. | 435/222 |
| 5,316,941 A | 5/1994 | Estell et al. | 435/252.3 |
| 5,403,737 A | 4/1995 | Abrahmsen et al. | 435/252.3 |
| 5,629,173 A | 5/1997 | Abrahmsen et al. | 435/68.1 |

FOREIGN PATENT DOCUMENTS

| | | |
|---|---|---|
| EP | 3 328 229 A1 | 8/1989 |
| WO | WO 91/16423 | 4/1991 |
| WO | WO 96/27671 | 2/1996 |
| WO | WO 97/37007 | 10/1997 |
| WO | WO 98/23732 | 6/1998 |

OTHER PUBLICATIONS

Akabas et al., "Acetylcholine Receptor Channel Structure Probed in Cysteine–Substitution Mutants," *Science*, 258:307–310 (1992).
Alvear et al., "Inactivation of Chicken Liver Mevalonate 5–Diphosphate Decarboxylase by Sulfhydrl–Directed Reagents: Evidence of a Functional Dithiol," *Biochimica et Biophysica Acta*, 994:7–11 (1989).
Bech, et al., "Chemical modifications of a cysteinyl residue introduced in the binding site of carboxypeptidases y by site–directed mutagenesis,", *Carlsberg Res. commun.*, 53:381–393 (1988).
Bech et al., "Significance of Hydrophobic $S_4$–$P_4$ Interactions in Subtilisin 309 from *Bacillus Lentus*, " *Biochemistry*, 32:2847–2852 (1993).
Bell et al., "Kinetic Studies on the Peroxidase Activity of Selenosubtilisin," *Biochemistry*, 32:3754–3762 (1993).
Berglund et al., "Chemical Modification of Cysteine Mutants of Subtillisin *Bacillus Lentus* Can Create Better Catalysts Than The Wild–Type Enzyme," *J. Am. Chem. Soc.*, 119:5265–5266 (1997).

Berglund, et al., Altering the specificity of subtilisin B. Llentus by combining site–directed mutagenesis and chemical modification, *Bioorganic & Medicinal Chemistry Letters*, 6:2507–2512 (1996).
Bodwell et al., "Sulfhydryl–Modifying Reagents Reversibly Inhibit Binding of Glucocorticoid–Receptor Complexes to DNA–Cellulose," *Biochemistry*, 23:1392–1398 (1984).
Bonneau et al., "Alteration of the Specificity of Subtilisin BPN' by Site Directed Mutagenesis in Its $S_1$ and $S_1$' Binding Sites," *J. Am. Chem. Soc.*, 113:1026–1030 (1991).
Brockelhurst, "Specific Covalent Modification of Thiols: Applications in the Study of Enzymes and Other Biomolecules," *Int. J. Biochem.*, 10:259–274 (1979).
Bruice et al., "Novel Alkyl Alkanethiolsulfonate Sulfhydryl Reagents. Modification of Derivatives of L–Cysteine," *Journal of Protein Chemistry*, 1:47–58 (1982).
Buckwalter, et al., "Improvement in the Solution Stability of Porcine Somatotropin by Chemical Modification of Cysteine Residues," *J. Agric. Food Chem.*, 40:356–362 (1992).
Daly et al., "Formation of Mixed Disulfide Adducts at Cysteine–281 of the Lactose Repressor Protein Affects Operator And Inducer Binding Parameters," *Biochemistry*, 25:5468–5474 (1986).
Davies et al., "A Semisynthetic Metalloenzyme Based on a Protein Cavity That Catalyzes the Enantioselective Hydrolysis of Ester and Amide Substrates," *J. Am. Chem. Soc.*, 119:11643–11652 (1997).
Davis, B.G., et al., "Altering the specificity of subtilisin *Bacillus lentus* through the introduction of positive charge at single amino acid sites," *Bioorganic and Medicinial Chemistry*, (Nov. 1999) 7(11) 2303–11, XPO000892841.
Davis, B.G., et al., "The controlled introduction of multiple negative charge at single amino acid sites in *subtilisin bacillus lentus,*" *Bioorganic and Medicnal Chemistry*, (Nov. 1999) 7(11) 2293–301, XPO000892840.
Desantis, G., et al, "Probing the altered specificity and catalytic properties of mutant subtilisin chemically modified at position S156C and S166C in the S1 pocket," *Bioorganic and Medicinal Chemistry*, (1999) 7/7 (1381–1387), XP000089243.
Desantis, G., et al., "Chemical Modifications at a single site can induce significant shifts in the pH profiles of a serine protease," *J. Am. Chem. Soc.*, 120:8582–8586 (1998).
Desantis, G., et al., "Site–Directed Mutagenesis combined with chemical modification as a strategy for altering the specificity of the S1 and S1' pockets of *subtilisin bacillus lentus,*" *Biochemistry*, 37: 5968–5973 (1998).

(List continued on next page.)

*Primary Examiner*—Elizabeth Slobodyansky
(74) *Attorney, Agent, or Firm*—McCutchen, Doyle, Brown & Enersen LLP

(57) ABSTRACT

This invention provides modified enzymes comprising one or more amino acid residues replaced by cysteine residues, where the cysteine residues are modified by replacing the thiol hydrogen in the cysteine residues with a substituent group providing a thiol side chain comprising a multiply charged moiety. The enzymes show improved interaction and/or specificity and/or activity with charged substrates.

21 Claims, 11 Drawing Sheets

OTHER PUBLICATIONS

Di Bello, "Total Synthesis of Proteins by Chemical Methods: The Horse Heart Cytochrome C Example," *Gazzetta chimica Italiana*, 126:189–197 (1996).

Dickman, M., et al., "Chemically modified mutants of *subtilisin bacillus lentus* catalyze transesterification reactions better than wild type," *Tetrahedron Asymmetry*, (Dec. 11 1998) 9/23 4099–4102, XPO000891276.

Engler et al., "Critical Functional Requirement for the Guanidinium Group of the Arginine 41 Side Chain of Human Epidermal Growth Factor as Revealed by Mutagenic Inactivation and Chemical Reactivation," *The Journal of Biological Chemistry*, 267:2274–2281 (1992).

Frillingos, et al., "Cysteine–Scanning Mutagenesis of Helix II and Flanking Hydrophilic Domains in the Lactose Permease of *Escherichia coli*," *Biochemistry*, 36:269–273 (1997).

Gloss et al., "Examining the Structural and Chemical Flexibility of the Active Site Base, Lys–258, of *Escherichia coli* Aspartate Aminotransferase by Replacement with Unnatural Amino Acids," *Biochemistry*, 34: 12323–12332 (1995).

Gron et al., "A Highly Active and Oxidation–Resistant Subtilisin–Like Enzyme Produced by a Combination of Site–Directed Mutagenesis and Chemical Modification," *Eur. J. Biochem.*, 194:897–901 (1990).

Hempel et al., "Selective Chemical Modification of Human Liver Aldehyde Dehydrogenases $E_1$ and $E_2$ by Iodoacetamide," *The Journal of Biological Chemistry*, 256:10889–10896 (1981).

Hilvert et al., "A Highly Active Thermophilic Semisynthetic Flavoenzyme," *J. Am. Chem. Soc.*, 110:682–689 (1988).

Hilvert et al., "New Semisynthetic Flavoenzymes Based on a Tetrameric Protein Template, Glyceraldehyde– 3–Phosphate Dehydrogenase," *J. Am. Chem. Soc.*, 107:5805–5806 (1985).

House et al., "$^1$H NMR Spectroscopic Studies of Selenosubtilisin," *Biochemistry*, 32:3468–3473 (1993).

Huang et al., "Improving the Activity of Immobilized Subtilisin by Site–Specific Attachment to Surfaces," *Anal. Chem.*, 69:4601–4607 (1997).

International Search Report, Jul. 21, 2000.

Kaiser, "Catalytic Activity of Enzymes Altered at Their Active Sites," *Agnew. Chem. Int. Ed. Engl.*, 27:913–922 (1988).

Kanaya et al., "Role of Cysteine Residues in Ribonuclease H from *Escherichia coli*," *Biochem. J.*, 271:59–66 (1990).

Kawase et al., "Effect of Chemical Modification of Tyrosine Residues on Activities of Bacterial Lipase," *Journal of Fermentation and Bioengineering*, 72:317–319 (1991).

Kenyon, et al., "Novel Sulfhydryl Reagents," *Methods Enzymol.*, 47:407–430 (1977).

Kirley, "Reduction and Fluorescent Labeling of Cyst(e)ine–Containing Proteins for Subsequent Structure Analyses," *Analytical Biochemistry*, 180:231–236 (1989).

Kluger et al., "Amino Group Reactions of the Sulfhydryl Reagent Methyl Methanesulfonothioate. Inactivation of D–3–hydroxybutyrate Dehydrogenase and Reaction with Amines in Water," *Can. J. Biochem*, 58:629–632 (1980).

Kokubo et al., "Flavohemoglobin: A Semisynthetic Hydroxylase Acting in the Absence of Reductase," *J. Am. Chem. Soc.*, 109:606–607 (1987).

Konigsberg, "Reduction of Disulfide Bonds in Proteins with Dithiothreitol," *Methods in Enzymology*, 25:185–188 (1972).

Kuang et al., "Enantioselective Reductive Amination of α–Amino Acids by a Pyridoxamine Cofactor in A Protein Cavity," *J. Am. Chem. Soc.*, 118:10702–10706 (1996).

Lewis et al., "Determination of Interactive Thiol Ionizations in Bovine Serum Albumin, Glutathione, and Other Thiols by Potentiometric Difference Titration," *Biochemistry*, 19:6129–6137 (1980).

Liu et al., "Site–Directed Fluorescence Labeling of P–Glycoprotein on Cysteine Residues in the Nucleotide Binding Domains," *Biochemistry*, 35:11865–11873 (1996).

Miller et al., "Peroxide Modifications of Monoalkylated Glutathione Reductase," *The Journal of Biological Chemistry*, 266:19352–19350 (1991).

Nakayama et al., "Chemical Modification of Cysteinyl, Lysyl and Histidyl Residues of Mouse Liver 17β–Hydroxysteroid Dehydrogenase," *Biochimica et Biophysica Acta*, 1120:144–150 (1992).

Nishimura et al., "Reversible Modification of the Sulfhydryl Groups of *Escherichia coli* Succinic Thiokinase with Methanethiolating Reagents, 5,5'–Dithio–bis(2–Nitrobenzoic Acid), p–Hydroxymercuribenzoate, and Ethylmercurithiosalicylate," *Archives of Biochemistry and Biophysics*, 170:461–467 (1975).

O'Connor et al., "Probing an Acyl Enzyme of Selenosubtilisin by Raman Spectroscopy," *J. Am. Chem. Soc.*, 118:239–240 (1996).

Pardo et al., "Cysteine 532 and Cysteine 545 Are the N–Ethylmaleimide–Reactive Residues of the Neurospora Plassma Membrane $H^+$–ATPase," *The Journal of Biological Chemistry*, 264:9373–9379 (1989).

Peterson et al., "Nonessential Active Site Residues Modulate Selenosubtilisin's Kinetic Mechanism," *Biochemistry*, 34:6616–6620 (1995).

Peterson et al., "Selenosubtilisin's Peroxidase Activity Does Not Require an Intact Oxyanion Hole," *Tetrahedron*, 53:12311–12317 (1997).

Planas et al., "Reengineering the Catalytic Lysine of Aspartate Aminotransferase by Chemical Elaboration of a Genetically Introduced Cysteine," *Biochemistry*, 30:8268–8276 (1991).

Plettner, E., et al., "Modulation of Esterase and Amidase Activity of *Subtilisin Bacillus Lentus* by Chemical Modification of Cysteine Mutants," *Journal of the American Chemical Society*, (Jun. 2 1999) 121/21, 4977–1984, XPO000891274.

Plettner, Erika et al., "A Combinatorial Approach to Chemical Modification of *Subtilisin Bacillus Lentus,*" *Bioorganic & Medicinal Chemistry Letters* (Sep. 8, 1998) vol. 8, No. 17, pp. 2291–2296, XP0004138220.

Polgar et al., "A New Enzyme Containing a Synthetically Formed Active Site. Thiol–Subtilisin," *Journal of American Chemical Society*, 88:3153–3154 (1966).

Polgar, "Spectrophotometric Determination of Mercaptide Ion, an Activated Form of SH–Group in Thiol Enzymes," *FEBS Letters*, 38:187–190 (1974).

Radziejewski et al., "Catalysis of N–Alkyl-1,4–Dihydronicotinamide Ozidation by a Flavopapain: Rapid Reaction in All Catalytic Steps," *J. Am. Chem. Soc.*, 107:3352–3354 (1985).

Raia et al., "Activation of *Sulfolobus Solfataricus* Alcohol Dehydrogenase by Modification of Cysteine Residue 38 with Iodoacetic Acid," *Biochemistry*, 35:638–647 (1996).

Ramachandran et al., "Stabilization of Barstar by Chemical Modification of the Buried Cysteines," *Biochemistry*, 35:8776–8785 (1996).

Roberts et al., "Reactivity of Small Thiolate Anions and Cysteine–25 in Papain Toward Methyl Methanethiosulfonate," *Biochemistry*, 25:5595–5601 (1986).

Rokita et al., "Synthesis and Characterization of a New Semisynthetic Enzyme, Flavolysozyme," *J. Am. Chem. Soc.*, 108:4984–4987 (1986).

Siddiqui et al., "Arthrobacter D–Xylose Isomerase: Chemical Modification of Carboxy Groups and Protein Engineering of pH Optimum," *Biochem. J.*, 295:685–691 (1993).

Smith et al., "An Engineered Change in Substrate Specificity of Ribulosebisphosphate Carboxylase/Oxygenase," *The Journal of Biological Chemistry*, 265:1243–1245 (1990).

Smith et al., Chemical Modification of Active Site Residues in γ–Glutamyl Transpeptidase, *The Journal of Biological Chemistry*, 270:12476–12480 (1995).

Smith et al., "Nonessentiality of the Active Sulfhydryl Group of Rabbit Muscle Creatine Kinase," *The Journal of Biological Chemistry*, 249:3317–3318 (1974).

Smith et al., "Restoration of Activity to Catalytically Deficient Mutants of Ribulosebisphosphate Carboxylase/Oxygenase by Aminoethylation," *The Journal of Biological Chemistry*, 263:4921–4925 (1988).

Smith et al., "Simple Alkanethiol Groups for Temporary Blocking of Sulfhydryl Groups of Enzymes," *Biochemistry*, 14:766–771 (1975).

Smith et al., "Subtle Alteration of the Active Site of Ribulose Bisphosphate Carboxylase/Oygenase by Concerted Site–Directed Mutagenesis and Chemical Modification," *Biochemical and Biophysical Research Communications*, 152:579–584 (1988).

Soper et al., "Effects of Substrates on the Selective Modification of the Cysteinyl Residues of D–Amino Acid Transaminase," *The Journal of Biological Chemistry*, 254:10901–10905 (1979).

Stauffer, et al., "Electrostatic Potential of the Acetylcholine Binding Sites in the Nicotinic Receptor Probed by Reactions Of Binding–Site Cysteines with Charged Methanethiosulfonates," *Biochemistry*, 33:6840–6849 (1994).

Stewart et al., "Catalytic Oxidation of Dithiols by a Semisynthetic Enzyme," *J. Am. Chem. Soc.*, 108:3480–3483 (1986).

Suckling et al., "Carbon–Carbon Bond Formation Mediated by Papain Chemically Modified by Thiazolium Salts," *Bioorganic & Medicinal Chemistry Letters*, 3:531–534 (1993).

Svensson et al., "Mapping the Folding Intermediate of Human Carbonic Anhydrase II. Probing Substructure by Chemical Reactivity and Spin and Fluorescence Labeling of Engineered Cysteine Residues," *Biochemistry*, 34:8606–8620 (1995).

Valenzuela et al., "Kinetic Properties of Succinylated and Ethylenediamine–Amidated 8–Chymotrypsins," *Biochim. Biophys. Acta*, 250:538–548 (1971).

West et al., "Enzymes as Synthetic Catalysts: Mechanistic and Active–Site Considerations of Natural and Modified Chymotrypsin," *J. Am. Chem. Soc.*, 112:5313–5320 (1990).

White et al., "Sequential Site–Directed Mutagenesis and Chemical Modification to Convert the Active Site Arginine 292 Of Aspartate Aminotransferase to Homoarginine," *Journal of the American Chemical Society*, 114:292–293 (1992).

Worku et al., Identification of Histidyl and Cysteinyl Residues Essential for Catalysis by 5'–Nucleotidase, *FEBS Letters*, 167:235–240 (1984).

Wu et al., "Conversion of a Protease into an Acyl Transferase: Selenolsubtilisin," *J. Am. Chem. Soc.*, 111:4514–4515 (1989).

Wynn et al., "Comparison of Straight Chain and Cyclic Unnatural Amino Acids Embedded in the Core of Staphylococcal Nuclease," *Protein Science*, 6:1621–1626 (1997).

Wynn et al., "Mobile Unnatural Amino Acid Side Chains in the Core of Staphylococcal Nuclease," *Protein Science*, 5:1026–1031 (1996).

Wynn et al., "Unnatural Amino Acid Packing Mutants of *Escherichia Coli* Thioredoxin Produced by Combined Mutagenesis/Chemical Modification Techniques," *Protein Science*, 2:395–403 (1993).

Wynn et al., "Chemical modification of Protein Thiols: Formation of Mixed Disulfides," *Methods in Enzymology*, 251:351–356 (1995).

Xu et al., "Amino Acids Lining the Channel of the γ–Aminobutyric Acid Type A Receptor Identified by Cysteine Substitution," *The Journal of Biological Chemistry*, 268:21505–21508 (1993).

Plettner et al. (Aug. 1998) Bioorganic & Medical Chemistry Letters, vol. 8, pp. 2291–2296.*

* cited by examiner

Scheme 2

*Scheme 3*

Scheme 4

Scheme 5

US 6,379,942 B1

CHEMICALLY MODIFIED ENZYMES WITH MULTIPLE CHARGED VARIANTS

CROSS-REFERENCE TO RELATED APPLICATIONS

This application claims benefit under 35 U.S.C. §119 of provisional application U.S. Ser. No. 60/113,130, filed on Dec. 21, 1998, which is herein incorporated by reference in its entirety for all purposes.

STATEMENT AS TO RIGHTS TO INVENTIONS MADE UNDER FEDERALLY SPONSORED RESEARCH AND DEVELOPMENT

[ Not Applicable ]

FIELD OF THE INVENTION

This invention relates to the field of chemically modified mutant enzymes. In particular this invention pertains to chemically modified mutant enzymes in which multiply charged substituents are introduced to enhance interaction of the enzyme with a charged substrate.

BACKGROUND OF THE INVENTION

For both protein chemistry (Nilsson et al. (1992) *Curr. Opin. Struct. Biol* 2: 569–575; LaVallie and McCoy (1995) *Curr. Opin. Biotechnol.* 6: 501–506; Uhlen and Moks (1990) *Methods Enzymol.* 185: 129–143) and organic synthesis applications (Sears and Wong (1996) *Biotechnol. Prog.* 12: 423–433; Faber (1997) *Biotransformations in Organic Synthesis:* 3rd ed. Springer-Verlag: Heidelberg; Roberts (1993) *Preparative Biotransformations; Wiley: New York:* 1993) it is desirable to have available a diverse toolbox of inexpensive proteases with high selectivity and diverse substrate preferences. To date the most extensively exploited class of enzymes in organic synthesis applications have been the hydrolases. Among these, the serine proteases have received considerable attention due, in part, to their often exquisite stereo-, regio-, and chemo-selectivities (Sears and Wong (1996) *Biotechnol. Prog.* 12: 423–433; Faber (1997) *Biotransformations in Organic Synthesis:* 3rd ed. Springer-Verlag: Heidelberg; Roberts (1993) *Preparative Biotransformations*; Wiley: New York: 1993; Moree et al. (1997) *J. Am. Chem. Soc.* 119: 3942–3947).

While over 3000 enzymes have now been reported, of which many are proteases, significantly fewer of the latter are available inexpensively from commercial sources (Faber (1997) *Biotransformations in Organic Synthesis:* 3rd ed. Springer-Verlag: Heidelberg; Roberts (1993) *Preparative Biotransformations*; Wiley: New York: 1993; Moree et al. (1997) *J. Am. Chem. Soc.* 119: 3942–3947; Jones (1986) *Tetrahedron* 42: 3351–3403). Furthermore, since wild type enzymes do not accept all substrate structures of synthetic interest, it is attractive to contemplate the tailoring of a readily available protease in order to expand their substrate specificities in a controlled manner with the ultimate goal of creating any desired specificity at will.

In this regard, the goal of specificity alteration of enzymes has already been targeted by several different approaches. For example, site-directed mutagenesis (Perona and Craik (1995) *Protein Sci.* 4: 337–360) and random mutagenesis (Arnold (1998) *Acc. Chem. Res.* 31(3): 125–131) have been employed to tailor enzyme specificity and have permitted some insights into the electrostatic (Wells et al. (1987) *Proc. Natl. Acad. Sci. USA*, 84: 5167–5171; Wells et al. (1987) *Proc. Nat. Acad. Sci. USA*, 84: 1219–1223; Wells and Estell (1988) *TIBS* 13: 291–297; Bott et al. (1987) Pages 139–147 In: *Biotech. Agric.Chem.*; Lebanon, Mumma, Honeycutt, Duesing, eds.; Vol. ACS Symp. Ser. 334; Russell et al. (1987) *J. Mol. Biol.* 193: 803–813; Ballinger et al. (196) *Biochemistry* 33: 13579–13585), steric (Rheinnecker et al. (1994) *Biochemistry* 33: 221–225; Rheinnecker et al. (1993) *Biochemistry* 32(5): 1199–1203; Sørensen et al. (1993) *Biochemistry* 32: 8994–8999; Estell et al. (1986) *Science* 233: 659–663; Takagi et al. (1996) *FEBS Lett.* 395: 127–132; Takagi et al. (1997) *Protein Eng.* 10(9): 985–989), and hydrophobic (Estell et al. (1986) *Science* 233: 659–663; Wangikar et al. (1995) *Biochemistry* 34(38): 12302–12310; Bech et al. (1993) *Biochemistry* 32: 2845–2852) factors which govern enzyme-substrate interactions. However, the structural variations within these approaches are limited to the 20-natural amino acids. Consequently, biosynthetic methods have recently been developed to introduce unnatural amino acids into proteins (25. Cornish et al. (1995) *Angew. Chem. Int. Ed.Eng.* 34: 621–633; Parsons et al. (1998) *Biochemistry* 37: 6286–6294; Hohsaka et al. (1996) *J. Am. Chem. Soc.* 118(40): 9778–9779). Unnatural functionalities have also been incorporated by chemical modification techniques (Kuang et al. (1996) *J. Am. Chem. Soc.* 118: 10702–10706; Ory et al. (1998) *Protein. Eng.* 11(4): 253–261; Peterson: E. B.; Hilvert: D. *Biochemistry* 34: 6616– 6620; Suckling: C. J.; Zhu: L.-M. *Bioorg. Med. Chem. Lett.* 3: 531–534; Rokita and Kaiser (1986) *J. Am. Chem. Soc.* 108: 4984–4987; Kokubo et al. (1987) *J. Am. Chem. Soc.* 109: 606–607; Radziejewski et al. (1985) *J. Am. Chem. Soc.* 107: 3352–3354). Generally, however, unnatural amino acid mutagenesis approach is not yet amenable to large scale preparations, and chemical modification alone is insufficiently specific.

SUMMARY OF THE INVENTION

This invention provides novel multiply-charged chemically modified mutant enzymes. In a particularly preferred embodiment this invention provides a modified enzyme where one or more amino acid residues in the enzyme are replaced by cysteine residues. The cysteine residues are modified by replacing the thiol hydrogen in the residue with a substituent group providing a thiol side chain comprising a multiply charged moiety. Preferred enzymes include serine hydrolases, more preferably proteases (e.g. subtilisins). One particularly preferred enzyme is a *Bacillus lentus* subtilisin.

The amino acid replaced with a cysteine may include an amino acid selected from the group consisting of asparagine, leucine, methionine, and serine. Preferred replaced amino acids are in a binding site (e.g., a subsite such as S1, S1', and S2). Where the enzyme is a subtilisin-type serine hydrolase the cysteine(s) is substituted amino acid(s) corresponding to a *Bacillus lentus* subtilisin residue selected from the group consisting of residue 156, reside 166, residue 217, residue 222, residue 62, residue 96, residue 104, residue 107, reside 189, and residue 209. Where the enzyme is a trypsin-chymotrypsin-type serine protease the cysteine(s) are substituted for and amino acid corresponding to a trypsin residue selected from the group consisting of Tyr94, Leu99, Gln175, Asp189, Ser190, and Gln192. Where the enzyme is an alpha/beta serine hydrolase the cysteine(s) are substituted for and amino acid corresponding to a *Candida antartica* lipase (protein Data Bank entry 1tca) residue selected from the group consisting of Trp104, Thr138, Leu144, Val154, Ile189, Ala225, Leu278 and Ile185.

The multiply charged moiety can be negatively or positive charged and in certain embodiments, the enzyme can contain both positively and negatively multiply charged moieties.

Particularly preferred negatively charged moieties include, but are not limited to, sulfonatoethyl thiol, 4-carboxybutyl thiol, 3,5-dicarboxybenzyl thiol, 3,3-dicarboxybutyl thiol, and 3,3,4-tricarboxybutyl thiol, while particularly preferred positively charged moieties include, but are not limited to, amingethyl thiol, 2 -(trimethylammonium)ethyl thiol, 4,4-bis(aminomethyl)-3-oxo-hexyl thiol, and 2,2-bis (aminomethyl)-3-aminopropyl thiol. The multiply charged moiety can also be a dendrimer or a polymer.

In another embodiment, this invention provides methods of making novel multiply-charged chemically modified mutant enzymes. The methods involve providing an enzyme having one or more amino acids have been replaced with cysteine residues; and replacing the thiol hydrogen, in one or more cysteine residues, with a substituent group providing a thiol side chain comprising a multiply charged moiety. In certain embodiments, a native cysteine can be chemically modified and there is no need to introduce a cysteine. Preferred enzymes include serine hydrolases as identified herein. Preferred residues for replacement with a cysteine and preferred multiply-charged moieties are identified herein.

In another embodiment, this invention includes a composition comprising any one of the multiply charged chemically modified mutant enzymes as described herein and a detergent or other cleaning agent.

In still another embodiment, this invention provides methods of assaying for a preferred enzyme. The methods involve providing a swatch of material comprising a piece of material and a stain; fixing the stain to the material; applying an enzyme to the swatch; and incubating the watch and the enzyme. The method can further involve determining the degree of removal of the stain from the material. Preferred enzymes for use in this method include, but are not limited to proteases, a cellulases, amylases, laccases, and lipases. In particularly preferred embodiments, the enzymes are modified serine hydrolases as described herein. Preferred materials include, but are not limited to fabrics, plastics, or ceramics. Preferred stains include, but are not limited to blood, milk, ink, grass, gravy, chocolate, egg, cheese, clay, pigment, and oil. One particularly preferred stain is a blood/milk/ink (BMI) stain.

The method can also involve incubating the stain with a cross-linking agent (e.g., hydrogen peroxide, bleaching agents, glutaraldehyde, and carbodiimides). The enzyme can be applied to the swatch in combination with a detergent ingredient. The method can additionally involve agitating the swatch and enzyme during incubation.

In still yet another embodiment, this invention provides methods of assaying for a preferred detergent composition. These methods involve providing a swatch of material comprising a piece of material and a stain; fixing the stain to the material; applying a detergent composition to the swatch; and incubating the watch and the detergent composition. The methods can additionally involve determining the degree of removal of the stain from the material. Preferred enzymes, materials and stains are as described herein. The method can involve incubating the stain with a cross-linking agent (e.g., hydrogen peroxide, bleaching agents, glutaraldehyde, and carbodiimides). The enzyme can be applied to the swatch in combination with the enzyme. In certain embodiments, the method involves agitating the swatch and detergent composition during incubation.

This invention also provides methods of determining the catalytic efficiency of an enzyme. The methods involve providing a swatch of material comprising a piece of material and a stain; applying the enzyme to the swatch; incubating the swatch and the enzyme; removing the swatch or supernatant; and measuring a constituent of the stain. Preferred enzymes, materials and stains are as described herein. The method can involve incubating the stain with a cross-linking agent (e.g., hydrogen peroxide, bleaching agents, glutaraldehyde, and carbodiimides). In certain preferred embodiments, the constituent is in d the supernatant. The constituent can be measured by determining its fluorescence and/or absorbance (e.g. absorbance spectra).

Also included herein are kits for the practice of the methods of this invention. One kit comprises a container containing a modified enzyme where one or more amino acid residues in the enzyme are replaced by cysteine residues, and the cysteine residues are modified by replacing the thiol hydrogen in the cysteine residues with a substituent group providing a thiol side chain comprising a multiply charged moiety. Another kit comprises a container containing a methane sulfonate reagent comprising a multiply charged substituent, and instructional materials teaching the use of the sulfonate reagent to couple a mutiply-charged moiety to a cysteine residue in a protein.

Definitons

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term may also include variants on the traditional peptide linkage joining the amino acids making up the polypeptide.

The term "residue" as used herein refers to natural, synthetic, or modified amino acids.

The terms enzyme includes proteins that are capable of catalyzing chemical changes in other substances without being permanently changed themselves. The enzymes can be wild-type enzymes or variant enzymes. Enzymes within the scope of the present invention include, but are not limited to, pullulanases, proteases, cellulases, amylases, isomerases, lipases, oxidases, oxidoreductases, hydrolases, aldolases, ketolases, glycosidases, oxidoreductases, hydrolases, aldolases, ketolases, glycosidases, lyases, ligases, transferases, and ligases.

The phrase "multiply-charged" or "multiple-charge" refers to a net charge greater than +1 or less than −1 at pH 7.0. A multiply charged substituent is a substituent that when covalently coupled to a subject enzyme bears a net charge greater than +1 or less than −1 at pH 7.0.

A "mutant enzyme" is an enzyme that has been changed by replacing an amino acid residue with a cysteine (or other) residue.

A "chemically modified" enzyme is an enzyme that has been derivatized to bear a substituent not normally found at that location in the enzyme.

A "chemically modified mutant enzyme" or "CMM" is an enzyme in which an amino acid residue has been replaced with another amino acid residue (preferably a cysteine) and the replacement residue is chemically derivatized to bear a substituent not normally found on that residue.

The term "thiol side chain group", "thiol containing group", and thiol side chain" are terms that can be used interchangeably and include groups that are used to replace the thiol hydrogen of a cysteine. Commonly the thiol side chain group includes a sulfur atom through which the thiol side chain group is attached to the thiol sulfur of the cysteine. The "substitutent" typically refers to the group remains attached to the cysteine through a disulfide linkage formed by reacting the cysteine with a methanesulfonate reagent as described herein. While the term substituent preferably refers just to the group that remains attached (excluding its thiol group), the substituent can also refer to the entire thiol side chain group. The difference will be clear from the context.

The "binding site of an enzyme" consists of a series of subsites across the surface of the enzyme. The substrate residues that correspond to the subsites are labeled P and the subsites are labeled S. By convention, the subsites are labeled $S_1$, $S_2$, $S_3$, $S_4$, $S_1'$, and $S_2'$. A discussion of subsites can be found in Siezen et al. (1991) *Protein Engineering*, 4: 719–737, and Fersht (1985) *Enzyme Structure and Mechanism*, 2nd ed. Freeman, New York, 29–30. The preferred subsites include $S_1$, $S_1'$, and $S_2$.

The terms "stereoselectivity" or "stereoselective" when used in reference to an enzyme or to a reaction catalyzed by an enzyme refers to a bias in the amount or concentration of reaction products in favor of enantiomers of one chirality. Thus a stereoselective reaction or enzyme will produce reaction products that predominate in the "D" form over the "L" form (or "R" form over the "S" form) or conversely that predominate in the "L" form over the "D" form (or "S" form over the "R" form). The predominance of one chirality is preferably a detectable predominance, more preferably a substantial predominance, and most preferably a statistically significant predominance (e.g. at a confidence level of at least 80%, preferably at least 90%, more preferably at least 95%, and most preferably at least 98%).

The phrase "amino acid ##" or "amino acid ## in the XX subsite" is intended to include the amino acid at the referenced position (e.g. amino 156 of *B. lentus* subtilisin which is in the $S_1$ subsite) and the amino acids at the corresponding (homologous) position in related enzymes.

A residue (amino acid) of a enzyme is equivalent to a residue of a referenced enzyme (e.g. *B. amyloliquefaciens* subtilisin) if it is either homologous (i.e., corresponding in position in either primary or tertiary structure) or analagous to a specific residue or portion of that residue in *B. amyloliquefaciens* subtilisin (i.e., having the same or similar functional capacity to combine, react, or interact chemically).

In order to establish homology to primary structure, the amino acid sequence of the subject enzyme (e.g. a serine hydrolase) is directly compared to a reference enzyme (e.g. *B. amyloliquefaciens* subtilisin) primary sequence and particularly to a set of residues known to be invariant in all enzymes of that family (e.g subtilisins) for which sequence is known. After aligning the conserved residues, allowing for necessary insertions and deletions in order to maintain alignment (i.e., avoiding the elimination of conserved residues through arbitrary deletion and insertion), the residues equivalent to particular amino acids in the primary sequence of the reference enzyme (e.g. *B. amyloliquefaciens* subtilisin) are defined. Alignment of conserved residues preferably should conserve 100% of such residues. However, alignment of greater than 75% or as little as 50% of conserved residues is also adequate to define equivalent residues. Conservation of the catalytic triad, (e.g., Asp32/His64/Ser221) should be maintained.

The conserved residues may be used to define the corresponding equivalent amino acid residues in other related enzymes. For example, the two (reference and "target") sequences are aligned in to produce the maximum homology of conserved residues. There may be a number of insertions and deletions in the "target" sequence as compared to the reference sequence. Thus, for example, a number of deletions are seen in the thermitase sequence as compared to *B. amyloliquefaciens* subtilisin (see, e.g. U.S. Pat. No. 5,972,682). Thus, the equivalent amino acid or Tyr217 in *B. amyloliquefaciens* subtilisin in thermitase is the particular lysine shown beneath Tyr217.

The particular "equivalent" resides may be substituted by a different amino acid to produce a mutant carbonyl hydrolase since they are equivalent in primary structure.

Equivalent residues homologous at the level of tertiary structure for a particular enzyme whose tertiary structure has been determined by x-ray crystallography, are defined as those for which the atomic coordinates of 2 or more of the main chain atoms of a particular amino acid residue of the reference sequence (e.g. *B. amyloliquefaciens* subtilisin) and the sequence in question (target sequence) (N on N, CA on CA, C on C, and O on O) are within 0.13 nm and preferably 0.1 nm after alignment. Alignment is achieved after the best model has been oriented and positioned to give the maximum overlap of atomic coordinates of non-hydrogen protein atoms of the enzyme in question to the reference sequence. The best model is the crystallographic model giving the lowest R factor for experimental diffraction data at the highest resolution available.

$$R = \frac{\sum_h |fo(h)| - |fc(h)|}{\sum_h |fo(h)|}$$

Equivalent residues which are functionally analogous to a specific residue of a reference sequence (e.g. *B. amyloliquefaciens* subtilisin) are defined as those amino acids sequence in question (e.g. related subtilisin) which may adopt a conformation such that they will alter, modify or contribute to protein structure, substrate binding or catalysis in a manner defined and attributed to a specific residue of the reference sequence as described herein. Further, they are those residues of the sequence in question (for which a tertiary structure has been obtained by x-ray crystallography), which occupy an analogous position to the extent that although the main chain atoms of the given residue may not satisfy the criteria of equivalence on the basis of occupying a homologous position, the atomic coordinates of at least two of the side chain atoms of the residue lie with 0.13 nm of the corresponding side chain atoms of the reference sequence. The three dimensional structures would be aligned as outlined above. For an illustration of this procedure see U.S. Pat. No. 5,972,682.

A "serine hydrolase" is a hydrolytic enzyme utilizing an active serine side chain to serve as a nucleophile in a hydrolytic reaction. This term includes native and synthetic serine hydrolases as well as enzymes engineered to perform the reverse reaction, e.g., for synthetic purposes.

The "alpha/beta serine hydrolases" are a family of serine hydrolyases based on structural homology to enzymes including wheat germ serine carboxypeptidase's II (see, e.g., Liam et al. (1992) *Biochemistry* 31: 9796–9812; Olli's et al. (1992) *Protein Engineering*, 5: 197–211).

The "subtilisin type serine proteases" refer to a family of serine hydrolyases based on structural homology to enzymes in including subtilisin BPN' (Bott et al. (1988) *J. Biol. Chem.* 263: 7895–7906; Siezen and Louise (1997) *Protein Science* 6: 501–523). Subtilisin are bacterial or fungal proteases which generally act to cleave peptide bonds of proteins or peptides. As used herein, "subtilisin" means a naturally-occurring subtilisin or a recombinant subtilisin. A series of naturally-occurring subtilisins is known to be produced and often secreted by various microbial species. Amino acid sequences of the members of this series are not entirely homologous. However, the subtilisins in this series exhibit the same or similar type of proteolytic activity. This class of serine proteases shares a common amino acid sequence defining a catalytic triad which distinguishes them from the chymotrypsin related class of serine proteases. The subtilisins and chymotrypsin related serine proteases have a catalytic triad comprising aspartate, histidine and serine. In the subtilisin related proteases the relative order of these amino acids, reading from the amino to carboxy terminus, is aspartate-histidine-serine. In the chymotrypsin related proteases, the relative order, however, is histidine-aspartate-serine. Thus, subtilisin herein refers to a serine protease having the catalytic triad of subtilisin related proteases.

The "chymotrypsin serine protease family" refers to a family of serine hydrolyases based on structural homology to enzymes including gamma chymotrypsin (Birktoft and Blow (1972) *J. Molecular Biology* 68: 187–240).

A "dendritic polymer" is a polymer exhibiting regular dendritic branching, formed by the sequential or generational addition of branched layers to or from a core. The term dendritic polymer encompasses "dendrimers", which are characterized by a core, at least one interior branched layer, and a surface branched layer (see, e.g., Petar et al. Pages 641–645 In *Chem. in Britain*, (August 1994). A "dendron" is a species of dendrimer having branches emanating from a focal point which is or can be joined to a core, either directly or through a linking moiety to form a dendrimer. Many dendrimers comprise two or more dendrons joined to a common core. However, the term dendrimer is used broadly to encompass a single dendron.

Dendritic polymers include, but are not limited to, symmetrical and unsymmetrical branching dendrimers, cascade molecules, arborols, and the like, though the most preferred dendritic polymers are dense star polymers. The PAMAM dense star dendrimers (disclosed in U.S. Pat. No. 5,714,166) are symmetric, in that the branch arms are of equal length. The branching occurs at the hydrogen atoms of a terminal —$NH_2$ group on a preceding generation branch. The lysine-based dendrimers are unsymmetric, in that the branch arms are of a different length. One branch occurs at the epsilon nitrogen of the lysine molecule, while another branch occurs at the alpha nitrogen, adjacent to the reactive carboxy group which attaches the branch to a previous generation branch.

Even though not formed by regular sequential addition of branched layers, hyperbranched polymers, e.g., hyperbranched polyols, may be equivalent to a dendritic polymer where the branching pattern exhibits a degree of regularity approaching that of a dendrimer.

A "swatch" is a piece of material (e.g. a natural or synthetic textile) that has a stain applied thereto. The material can be, for example, a fabric made of a natural fiber (e.g. cotton, hemp, wool), or a synthetic material (e.g. nylon, polyester, rayon, etc.) or a mixture of synthetic or natural fibers. The material need not be a textile, but can be any material subject to cleaning operations (e.g. glass, ceramic, Formica, etc.).

A "smaller swatch" is one that has been cut from the swatch of material either before or after fixing a stain to the swatch and can, for example, fit into the well of a 48 or 96 well microtiter plate. The "smaller swatch" can also be made by applying a stain to a smaller piece of material. Preferably the smaller swatch is about ⅝ inch in diameter, more preferably the smaller swatch is about 0.25 inches in diameter.

The phrase "replacing the thiol hydrogen, in said one or more cysteine residues" does not require that every thiol hydrogen in every cysteine residue be replaced.

BRIEF DESCRIPTION OF THE DRAWINGS

FIG. 4A: The $k_{cat}/K_M$s for N62C CMMs alternate at moderately reduced levels, 1.5- to 3.5-fold lower than WT, which are established by the initial mutation to N62C (R=H). FIG. 4B: L217C CMMs show steady but lower levels of $k_{cat}/K_M$, 4- to 5.5-fold lower than WT, which are again established by the initial mutation to cysteine. The exception is L217C-c which is only 2.5-fold lower than WT, possibly due to favorable binding of substrate to the phenyl ring of the aromatic side chain introduced by modification. FIG. 4C: From the small reduction caused by mutation to S156C (R=H), $k_{cat}/K_M$s decrease monotonically to 6-fold lower than WT for S156C-d. The $k_{cat}/K_M$ of S156C-e is partially restored. FIG. 4D: $k_{cat}/K_M$ decreases only 2.5-fold upon mutation to S166C (R=H) but decreases dramatically to 11-fold lower than WT when the negatively charged sulfonatoethyl side chain a is introduced. In parallel to N62C and L217C CMMs, $k_{cat}/K_M$ for S166C CMMs does not decrease further to any significant extent as the level of negative charge increases. R group key: a=sulfonatoethyl; b=4-carboxybutyl; c=3,5-dicarboxybenzyl; d=3,3-dicarboxybutyl; e=3,3,4-tricarboxybutyl.

DETAILED DESCRIPTION

Figure 1:
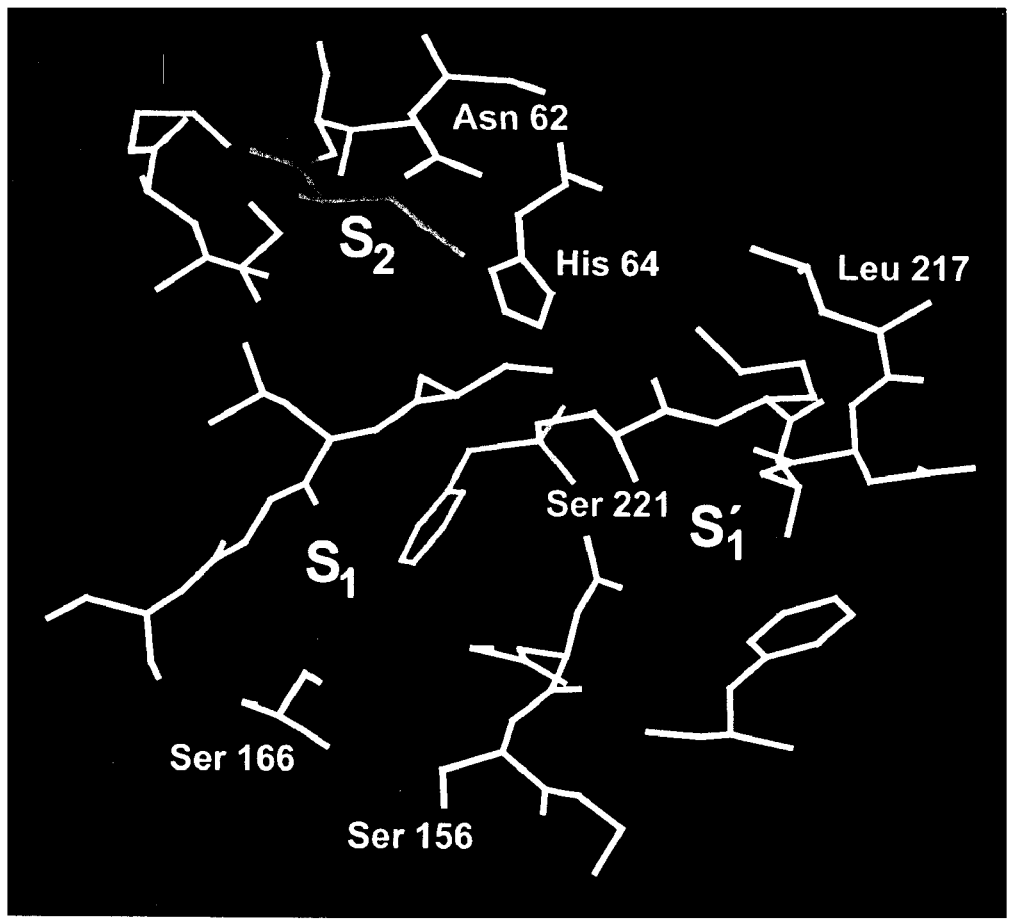
FIG. 1 illustrates the active site of SBL and shows the residues of the catalytic triad, Ser221, His64 and Asp32. The irreversible phenylmethylsulfonyl inhibitor (pink) forms a bond to the O. atom of Ser221 and its phenyl ring occupies the $S_1$ binding site. The residues chosen for mutation, Asn62 in the $S_2$ site, Ser156 and Ser166 in the $S_1$ site and Leu217 in the $S_1'$ site are highlighted.

This invention provides chemically modified mutant enzymes (CMMs) that bear multiply charged moieties. Without being bound to a particular theory, it was discovered that the addition of charge (positive or negative) improves the interaction of an enzyme with (oppositely) charged substrates. Moreover, it was a discovery of this invention that increasing the charge on the enzyme can increase the specificity and/or activity of that enzyme for a substrate, particularly for a charged substrate.

This is illustrated herein in Example 3 wherein a series of mono-, di-, and tri-negatively charged chemically modified mutant enzymes generated and all showed improved $k_{cat}/K_M$s with the positively charged $P_1$ residue containing substrate, suc-AAPR-pNA. Moreover, virtually arithmetic improvements in $k_{cat}/K_M$ were exhibited with increasing number of negative charges on the S166C-R side chain. These increases culminated in a 9-fold improvement in $k_{cat}/K_M$ for the suc-AAPR-pNA substrate and a 61-fold improvement in suc-AAPR-pNA/suc-AAPF-pNA selectivity compared to WT-SBL for the tri-negatively charged S166C-S—$CH_2CH_2C(COO^-)_3$ CMM. Conversely, the positively charged S166C-S—$CH_2CH_2NH_3^+$ CMM generated showed a 19-fold improvement in $k_{cat}/K_M$ for the suc-AAPE-pNA substrate and a 54-fold improvement in suc-AAPE-pNA/suc-AAPF-pNA selectivity relative to WT-SBL.

Thus, it is demonstrated herein that the addition of charge it to an enzyme; can have important effects on the activity of that enzyme against a charged substrate and that the magnitude of that effect is a function of the amount of charge. The addition of multiple charges using site-directed mutagenesis, however, is cumbersome, typically requiring a separate mutated residue for each charge.

This difficulty is overcome herein by the use of chemically modified mutant enzymes. In a preferred embodiment, one or more cyteines are introduced into the subject enzyme (e.g. via site-directed mutagenesis) and the sulfhydryl group on the cysteine provides a convenient relatively reactive thiol group (—SH) that can be exploited for coupling a desired (multiply-charged) substituent to the cysteine. In a preferred embodiment, the multiply-charged substitutent of interest is provided, derivatized as a methanethiosulfonate reagent which, when reacted with the cysteine, results in the substituent of interest covalently coupled to the cysteine by a disulfide linkage (—S—S—). Using this strategy, multiple charges can be added to an enzyme with as little as one mutation, or, where the enzyme naturally possesses a suitable native cysteine, with no mutations.

If will be noted that, in general, the location of the introduced charge is not critical. In general increasing the net positive or negative charge of the enzyme (e.g. by introducing charge essentially anywhere on the surface) will increase the ability of that enzyme to interact with an oppositely charged substrate. The enzyme can be routinely screened to verify that the introduced charge does not significantly diminish the activity and/or specificity of the enzyme. In certain instanc of the enzyme in question with "target substrate" in which case, it is often desirable to place added charge within a subsite of the enzyme (e.g. in the case of a serine protease in the $S_1$, $S_1'$ or S2 subsite).

I. Production of Mutant Enzymes for Chemical Modification
  A) Selection of Enzymes for Modification Virtually any enzyme can be modified (by the introduction of multiple charges) according to the methods of this invention. Such enzymes include, but are not limited to, pullulanases, proteases, cellulases, amylases, isomerases, lipases, oxidases, oxidoreductases, hydrolases, aldolases, ketolases, glycosidases, oxidoreductases, hydrolases, aldolases, ketolases, glycosidases, lyases, ligases, transferases, ligases, and the like. Preferred enzymes for modification according to this invention include the serine hydrolases. The serine hydrolases are a class of hydrolytic enzymes characterized by a hydrolytic enzymes that posses a catalytic triad composed of a serine, histidine and a carboxylate amino acid (either aspartic or glutamic acid), and which catalyze the hydrolysis, and microscopic reverse reactions thereof, of carboxylic acid derivatives including, but not restricted to, esters, peptides and amides.

Preferred serine hydrolases comprising this invention include the trypsin-chymotrypsin proteases, the subtilisin proteases, and the alpha/beta hydrolases. In a particularly preferred embodiment the enzyme is protease, more preferably a subtilisin (e.g. a *Bacillus lentus* subtilisin). Subtilisin is a serine endoprotease (MW ~27,500) which is secreted in large amounts from a wide variety of Bacillus species. The protein sequence of subtilisin has been determined from at least four different species of Bacillus (see, e.g., Markland et al. (1971) pages 561–608 In: *The Enzymes*, ed. Boyer P. D., Acad Press, New York, Vol. III, pp.; Nedkov et al. (1983) *Hoppe-Seyler's Z. Physiol. Chem.* 364: 1537–1540). The three-dimensional crystallographic structure of subtilisin BPN' (from *B. amyloliquefaciens*) to 2.5 Å resolution has also been reported (Wright et al. (1969) Nature 221, 235–242; Drenth et al. (1972) *Eur. J Biochem.* 26: 177–181. These studies indicate that although subtilisin is genetically unrelated to the mammalian serine proteases, it has a similar active site structure. The x-ray crystal structures of subtilisin containing covalently bound peptide inhibitors (Robertus, et al. (1972) *Biochemistry* 11: 2439–2449), product complexes (Robertus et al. (1972) *Biochemistry* 11: 4293–4303), and transition state analogs (Matthews et al (1975) *J. Biol. Chem.* 250: 7120–7126; Poulos et al. (1976) *J. Biol. Chem.*

251, 1097–1103), which have been reported have also provided information regarding the active site and putative substrate binding cleft of subtilisin. In addition, a large number of kinetic and chemical modification studies have been reported for subtilisin (Philipp et al. (1983) *Mol. Cell. Biochem.* 51:5–32; Svendsen (1976) *Carlsbera Res. Comm.* 41: 237–291; Markland, Id.) as well as at least one report wherein the side chain of methionine at residue 222 of subtilisin was converted by hydrogen peroxide to methionine-sulfoxide (Stauffer et al. (1965) *J. Biol. Chem.* 244: 5333–5338).

Other particularly preferred serine hydrolases for use in this invention include, but are not limited to α/β hydrolases and trypsin/chymotryspsin families of structurally serine hydrolase enzymes.

B) Selection of Residues for Modification

In general, virtually any residue of the enzyme can be selected for site-directed mutagenesis and chemical modification to introduce a multiply-charged substituent as long as the modification retains the desired level of activity of the subject enzyme. Typically this is accomplished by making the substitution at a location that does not block critical substrate interactions or drastically alter folding/conformation of the subject enzyme.

In one preferred embodiment, residues for modification in the enzyme (e.g. serine hydrolase) are rationally selected. Preferred sites include sites not in critical conformation determining regions and sites disposed away from the subsite(s) of the enzyme. However, in other preferred embodiments, particularly where it is desired to enhance, or otherwise alter, substrate specificity and/or activity, preferred amino acid residues selected for modification include residues expected to be important discriminatory sites within the subsites of the enzyme. Such resides are determined from mutagenesis experiments where the subsite residues are systematically mutagenized and the effect of such mutagenesis on binding specificity and/or enzymatic activity is determined. In addition, important residues can be identified from inspection of crystal structures and/or from predicted protein folding or protein-protein interactions determined using protein modeling software (e.g., Quanta (Molecular Simulations Inc.) and Frodo (academic software). Side chains situated to alter interaction at subsites defined by Berger and Schecter can be selected based on the crystallographic models of the enzymes and extrapolated to homologous enzymes if necessary if structural information on a specific enzyme is unavailable. In *B. lentus* subtilisin sites 62, 156, 166, 217 and 222 are important substrate specificity determining sites. Additional related sites include position 96, 104, 107, 189 and 209 in subtilisin and homologous positions in related enzymes. In preferred embodiments, such residues typically lie in the S1, S1', or S2 subsites although it will be appreciated that in certain cases, alteration of residues in other subsites can also produce dramatic effects.

In one particularly preferred embodiment, where the serine hydrolase is a subtilisin-type serine hydrolase, preferred residues for mutation include, but are not limited to residues 156 and 166 in the S1 subsite, residues 217 and 222 in the S1' subsite and residue 62 in the S2 subsite Leu96, Val104, Ile107, Phe189 and Tyr209 or residues at homologous positions within the subsites of other subtilisin-type serine proteases.

In another preferred embodiment, where the serine hydrolase is a trypsin-chymotrypsin type serine hydrolase, preferred residues for mutation include, but are not limited to, Tyr94, Leu99, Gln175, Asp189, Ser190 and Gln192 of trypsin or residues at homologous positions within the subsites of other trypsin-chymotrypsin-type serine proteases.

In still another preferred embodiment, where the serine hydrolase is an alpha/beta serine hydrolase, preferred residues for mutation include, but are not limited to, Trp104, Thr138, Leu144, Val154, Ile189, Ala225, Leu278 and Ile185 of *Candida antartica* lipase (Protein Data Bank entry 1tca) or residues at homologous positions within the subsites of other alpha/beta type serine hydrolases.

Preferably the amino acids replaced in the enzyme by cysteines are selected from the group consisting of asparagine, leucine, methionine, or serine. More preferably the amino acid to be replaced is located in a subsite of the enzyme preferably the S1, S1' or S2 subsites. More preferably, in a subtilisin the amino acids to be replaced are N62, L217, M222, S156, S166, site 104, site 107 (S4), site 96 (S2), site 189(S2'), and site 209 (S1'/S3') or their homologues where the numbered position corresponds to naturally occurring subtilisin from *Bacilus amyloliquefacients* or to equivalent amino acid residues in other subtilisins such as *Bacillus lentus* subtilisin.

C) Introduction of Cysteine

The substitution of a cysteine for one or more native residue(s) in the enzyme (e.g. serine hydrolase) can be accomplished using routine methods well known to those of ordinary skill in the art. In one preferred embodiment, the mutants described herein are most efficiently prepared by site-directed mutagenesis of the DNA encoding the wild-type enzyme of interest (e.g. *Bacillus lentis* subtilisin). Techniques for performing site-directed mutagenesis or non-random mutagenesis are known in the art. Such methods include, but are not limited to alanine scanning mutagenesis (Cunningham and Wells (1989) *Science,* 244, 1081–1085), oligonucleotide-mediated mutagenesis (Adellman et al. (1983) *DNA,* 2, 183), cassette mutagenesis (Wells et al. (1985) *Gene,* 344: 315) and binding mutagenesis (Ladner et al. WO 88/06630).

In one embodiment of the present invention, the substitute amino acid residue (e.g. cysteine) is introduced into the selected position by oligonucleotide-mediated mutagenesis using the polymerase chain reaction technique. In this approach, the gene encoding the desired native enzyme (e.g. subtilisin) is carried by a suitable plasmid. More preferably, the plasmid is an expression vector, e.g., a plasmid from the pBR, pUC, pUB, pET or pHY4 series. The plasmid can be chosen by persons skilled in the art for convenience or as desired.

For site-directed mutagenesis, the fragment containing the selected mutation site is cleaved from the gene encoding the subject enzyme by restriction endonucleases is used as the template in a modified PCR technique (see, Higuchi et al. (1988) *Nucleic Acid Res.,* 16, 7351–7367). For each target substitution, an oligonucleotide containing the desired mutation is used as a mismatch primer to initiate chain extension between 5' and 3 PCR flanking primers. The process includes two PCR reactions. In the first PCR, the mismatch primer and the 5' primer are used to generate a DNA fragment containing the desired base substitution. The fragment is separated from the primers by electrophoresis. After purification, it is then used as the new 5' primer in a second PCR with the 3' primer to generate the complete fragment containing the desired base substitution. After confirmation of the mutation by sequencing, the mutant fragment is then inserted back to the position of the original fragment.

In another approach, a cassette mutagenesis method may be used to facilitate the construction and identification of the cysteine mutants of the present invention. First, the gene encoding the serine hydrolase is obtained and sequenced in whole or in part. Then the point(s) at which it is desired to make a mutation of one or more amino acids in the expressed enzyme are identified. The sequences flanking these points are evaluated for the presence of restriction sites for replacing a short segment of the gene with an oligonucleotide which when expressed will encode the desired mutants. Such restriction sites are preferably unique sites within the serine hydrolase gene so as to facilitate the replacement of the gene segment. However, any convenient restriction site which is not overly redundant in the hydrolase gene may be used, provided the gene fragments generated by restriction digestion can be reassembled in proper sequence. If restriction sites are not present at locations within a convenient distance from the selected point (e.g., from 10 to 15 nucleotides), such sites are generated by substituting nucleotides in the gene in such a fashion that neither the reading frame nor the amino acids encoded are changed in the final construction. The task of locating suitable flanking regions and evaluating the needed changes to arrive at two convenient restriction site sequences is made routine by the redundancy of the genetic code, a restriction enzyme map of the gene and the large number of different restriction enzymes. If convenient flanking restriction site is available, the above method need be used only in connection with the flanking region which does not contain a site.

Mutation of the gene in order to change its sequence to conform to the desired sequence is accomplished e.g., M13 primer extension in accord with generally known methods. Once the gene is cloned, the restriction sites flanking the sequence to be mutated are digested with the cognate restriction enzymes and the end termini-complementary oligonucleotide cassette(s) are ligated into the gene. The mutagenesis is enormously simplified by this method because all of the oligonucleotides can be synthesized so as to have the same restriction sites, and no synthetic linkers are necessary to create the restriction sites.

A suitable DNA sequence computer search program simplifies the task of finding potential 5' and 3' convenient flanking sites. In preferred embodiments, any mutation introduced in creation of the restriction site(s) are silent to the final construction amino acid coding sequence. For a candidate restriction site 5' to the target codon a sequence preferably exists in the gene that contains at least all the nucleotides but for one in the recognition sequence 5' to the cut of the candidate enzyme. For example, the blunt cutting enzyme SmaI (CCC/GGG) would be a good 5' candidate if a nearby 5' sequence contained NCC, CNC, or CCN. Furthermore, if N needed to be altered to C this alteration preferably leaves the amino acid coding sequence intact. In cases where a permanent silent mutation is necessary to introduce a restriction site one may want to avoid the introduction of a rarely used codon. A similar situation of SmaI would apply for 3' flanking sites except the sequence NGG, GNG, or GGN must exist. The criteria for locating candidate enzymes are most relaxed for blunt cutting enzymes and most stringent for 4 base overhang enzymes. In general many candidate sites are available.

A particularly preferred of method of introducing cysteine mutants into the enzyme of interest is illustrated with respect to the subtilisin gene from *Bacillus lentus* ("SBL"). In a preferred embodiment, the gene for SBL is cloned into a bacteriophage vector (e.g. M13mp19 vector) for mutagenesis (see, e.g. U.S. Pat. No. 5,185,258). Oligonucleotide-directed mutagenesis is performed according to the method described by Zoller et al. (1983) *Meth. Enzymol.*, 100: 468–500. The mutated sequence is then cloned, excised, and reintroduced into an expression plasmid (e.g. plasmid GG274) in the *B. subtilis* host. PEG (50%) is added as a stabilizer.

The crude protein concentrate thus obtained is purified by first passing through a Sephadex™ G-25 desalting matrix with a pH 5.2 buffer (e.g. 20 mM sodium acetate, 5 mM $CaCl_2$) to remove small molecular weight contaminants. Pooled fractions from the desalting column are then applied to a strong cation exchange column (e.g. SP Sepharose™ FF) in the sodium acetate buffer described above and the SBL is eluted with a one step gradient of 0–200 mM NaCl acetate buffer, pH 5.2. Salt-free enzyme powder is obtained following dialysis of the eluent against Millipore purified water and subsequent lyophilization.

The purity of the mutant and wild-type enzymes, which are denatured by incubation with a 0.1 M HCl at 0° C. for 30 minutes is ascertained by SDS-PAGE on homogeneous gels (e.g. using the Phast™ system from Pharmacia, Uppsala, Sweden). The concentration of SBL is determined using the Bio-Rad (Hercules, Calif.) dye reagent kit which is based on the method of Bradford (1976) *Anal. Biochem.*, 72: 248–254). Specific activity of the enzymes is determined as described below and in the examples.

One of ordinary skill in the art will appreciate that the protocol described above can be routinely modified, if necessary, for use with other enzymes. Other protocols for site-directed modification of proteins are well know to those of skill in the art and can be found, for example, in U.S. Pat. Nos. 5,932,419 and 5,789,166, 5,705,479, 5,635,475, 5,556, 747, 5,354,670, 5,352,779, 5,284,760, and 5,071,743.

In addition, kits for site-directed mutagenesis are commercially available (see, e.g. Transfomer™ Site-Directed Mutagenesis Kit available from Toyobo).

D) Expression of the Mutated Enzyme

In a preferred embodiment, the mutated enzyme is expressed from a heterologous nucleic acid in a host cell. The expressed enzyme is then isolated and, if necessary, purified. The choice of host cell and expression vectors will to a large extent depend upon the enzyme of choice and its source.

A useful expression vector contains an element that permits stable integration of the vector into the host cell genome or autonomous replication of the vector in a host cell independent of the genome of the host cell, and preferably one or more phenotypic markers that permit easy selection of transformed host cells. The expression vector may also include control sequences encoding a promoter, ribosome binding site, translation initiation signal, and, optionally, a repressor gene, a selectable marker or various activator genes. To permit the secretion of the expressed protein, nucleotides encoding a signal sequence may be inserted prior to the coding sequence of the gene. For expression under the direction of control sequences, a gene or cDNA encoding a mutated enzyme to be used according to the invention is operably linked to the control sequences in the proper reading frame.

Vectors containing the mutant genes obtained by site-directed mutagenesis are then used respectively to transform suitable host cells and expressed. Suitable host cells include bacteria such as *E. coli* or Bacillus, yeast such as *S. cerevisiae*, mammalian cells such as mouse fibroblast cell, or insect cells. Preferably, a bacterial expression system is used. Most preferably, the host is Bacillus. Protein expression is performed by processes well known in the art according to factors such as the selected host cell and the expression vector to culture the transformed host cell under conditions favorable for a high-level expression of the foreign plasmid.

Methods of cloning and expression of peptides are well known to those of skill in the art. See, for example, Sambrook, et al. (1989) *Molecular Cloning: a Laboratory Manual* (2nd Ed., Vols. 1–3, Cold Spring Harbor Laboratory), Berger and Kimmel (1987) *Methods in Enzymology, Vol.* 152: *Guide to Molecular Cloning Techniquesl , Academic Press, Inc. San Diego, or Ausubel et al.* (1987) *Current Protocols in Molecular Biology*, Greene Publishing and Wiley-Interscience, New York.

As indicated above, one particularly preferred expression system is plasmid GG274 which is then expressed in a *B. subtilis* host.

II. Chemical Modification of Mutant Enzyme

A) Selection of Substitutents for Modifying Mutated Residues

A wide variety of substitutents can be used to modify the cysteine(s) introduced into the subject enzyme (e.g. serine hydrolase). As indicated above, preferred substituents are those that are multiply-charged once coupled to the target cysteine. Thus, preferred substituents, once coupled, have a net charge ±1, preferably a net charge of ±2, more preferably of ±3, and most preferably of ±4 or more.

In one preferred embodiment, the multiply charged moiety is negatively charged. Preferred multiply negatively charged moieties include, but are not limited to sulfanato, sulfinato, carboxy, phoshate, phosphite, etc. groups attached to straight chain $C_2$–$C_{15}$ alkyl, branched chain $C_3$–$C_{15}$ alkyl, and to such chains containing heteroatoms such as oxygen, sulfur, nitrogen, silicon, or substituted by aliphatic, aromatic, aralkyl, haloaliphatic, haloaromatic, haloaralkyl, heterocyclic, and poycyclic combinations thereof, groups (and their $C_3$–$C_{20}$ cycloalkyl, etc equivalents), to crown ethers, to cyclodextrins, to sugar moities, to monosaccharides, to oligosacharrides, to terpenoids, to alkaloids, and to sulfonatoethyl thiol, 4-carboxybutyl thiol, 3,5-dicarboxybenzyl thiol, 3,3-dicarboxybutyl thiol, and 3,3, 4-tricarboxybutyl thiol, and the like.

In another embodiment, the multiply charged moiety (substituent) is positively charged. Preferred multiply positively moieties include, but are not limited to, primary amino, secondary amino, tertiary amino. quaternary ammonium, guanidinium, etc. groups attached to straight chain $C_2$–$C_{15}$ alkyl, branched chain $C_3$–$C_{15}$ alkyl, and to such chains containing heteroatoms such as oxygen, sulfur, nitrogen, silicon, or substituted by aliphatic, aromatic, aralkyl, haloaliphatic, haloaromatic, haloaralkyl, heterocyclic, and poycyclic combinations thereof, groups (and their C—$C_{20}$ cycloalkyl etc equivalents), to crown ethers, to cyclodextrins, to sugar moities, to monosaccharides, to oligosacharrides, to terpenoids, to alkaloids, and to aminoethyl thiol, 2-(trimethylammonium) ethyl thiol, 4,4-bis(aminomethyl)-3-oxo-hexyl thiol, and 2,2-bis(aminomethyl)-3-aminopropyl thiol, and the like.

High levels of charge can be introduced by the use of linear polymers, branched polymers, and highly branched polymers/dendrimers. Highly charged (e.g. polycation) dendrimers are well known to those of skill in the art. For example polyionic dendrimers are typically three dimensional, highly ordered oligomeric and/or polymeric compounds formed on a core molecule or designated initiator by reiterative reaction sequences adding the oligomers and/or polymers and providing an outer surface that is positively or negatively charged. These dendrimers may be prepared as disclosed in PCT/US83/02052, and U.S. Pat. Nos. 4,507,466, 4,558,120, 4,568,737, 4,587,329, 4,631, 337, 4,694,064, 4,713,975, 4,737,550, 4,871,779, and 4,857, 599 or according to other methods well known to those of skill in the art. Typically, the dendrimers comprise a core molecule upon which polymers are added. The polymers may be oligomers or polymers which comprise terminal groups capable of acquiring a positive or negative charge. Suitable core molecules comprise at least two reactive residues which can be utilized for the binding of the core molecule to the oligomers and/or polymers. Examples of the reactive residues are hydroxyl, ester, amino, imino, imido, halide, carboxyl, carboxyhalide maleimide, dithiopyridyl and sulfhydryl, among others. Preferred core molecules are ammonia, tris-(2-aminoethyl)amine, lysine, ornithine, pentaerythritol and ethylenediamine, among others. Combinations of these residues are also suitable as are other reactive residues.

Oligomers and polymers suitable for the preparation of the dendrimer polycations of the invention include, but are not limited to polyamidoamines derived from the reaction of an alkyl ester of an a, O-ethylenically unsaturated carboxylic acid or an α,β-ethylenically unsaturated amide and an alkylene polyamine or a polyalkylene polyamine, among others. Preferred are methyl acrylate and ethylenediamine.

Preferred multiply-charged polymers and/or dendrimers for use in the methods of this invention include, but are not limited to essentially any charged polymer and/or dendrimer. Preferred dendrimers include, but are not limited to glycodendrimers. Glycodendrimers are well known to those of skill in the art (see, e.g., *Parameswaran* (1990) *Org. Prep. Proc. Intl.,* 22: 119–121, Green (1970) *Meth. Enzym.,* 18A: 418–424, and U.S. Pat. No. 2,489,237).

While in certain embodiments, the introduced multiply charged moieties are either positively charged or negatively charged, this invention need not be so restricted. Thus, for example, where it is desired to introduce a dipole moment to the subject enzyme, multiply-charged positive moieties can be introduced at one location in the enzyme and multiply-charged negative moieties can be introduced at another location within the enzyme.

B) Coupling Substituents to the Cysteine

The R group on cysteines provides a convenient relatively reactive thiol group (—SH) that can be exploited for coupling a desired multiply-charged substituent to the cysteine. In a preferred embodiment, the substitutent of interest is provided, derivatized as a methanethiosulfonate reagent which, when reacted with the cysteine, results in the substituent of interest covalently coupled to the cysteine by a disulfide linkage (—S—S—).

In a preferred embodiment, chemical modification with the methanethiosulfonate reagent(s) is carried out as described by Berglund et al. (1997) *J. Am. Chem. Soc.,* 119: 5265–5255 and DeSantis et al. (1998) *Biochemistry,* 37: 5968–5973. Briefly, 200 μL of a 1 M solution of the methanethiosulfonate (MTS) reagent is added to a solution (5–10 mg/mL, 3.5 mL) of the cysteine mutant in 70 mM CHES, 5 mM MES, 2 mM $CaCl_2$, pH 9.5. The MTS reagent is added in two portions over 30 minutes. Reaction mixtures are kept at 20° C. with continuous end-over-end mixing. Reactions are monitored by following the specific activity (e.g. with suc-AAPF-pNA) and by tests for residual free thiol (e.g. with Ellman's reagent). Once the reaction is complete, the reaction mixture is loaded on a Sephades™ (PD-10 G25 column with 5 mM MES and 2 mM CaCl2, pH 6,5. The protein fraction is then dialyzed against 1 mM CaCl2 and the dialysate is lyophilized.

In certain instances, where the substituent that is to be coupled to the cysteine, bears reactive groups the reactive groups may be derivatized with appropriate blocking/ protecting groups to prevent undesired reactions during the coupling. Similarly, where the serine hydrolase contains one or more cysteines that are not to be derivatized, the thiol group(s) on these cysteines may be derivatized with appropriate protecting groups (e.g. (e.g. benzyl, trityl, tert-butyl, MOM, acetyl, thiocarbonate, thiocarbamate, and others). The use of blocking/protecting groups is well know to those of skill in the art (see, e.g., *Protective Groups in Organic Synthesis*" Theodora W. Greene and Peter G. M. Wuts Third Edition, Wiley-Interscience, Toronto, (1999), pp 454–493.)

III. Screening Chemically Modified Mutants for Desired Activity

The multiply-charged chemically modified mutant enzymes of this invention are typically screened for the activity or activities of interest. Such activities include, but are not limited to, protease activity, lipase activity, cellulase activity, amylase activity, and the like. In a preferred embodiment the activity is measured against one or more test substrates, e.g. as illustrated in the examples. Thus, for example, the multiply charged mutant proteases can be assayed against synthetic substrates such the suc-AAPA-pNA substrate and suc-AAPF-pNA substrates illustrated in the examples. Other suitable synthetic substrates for measuring enzymatic activity are well known to those of skill in the art (see, e.g., Colowick (1970) *Proteolytic Enzymes*, Meth. Enzymology, Vol. 19 Academic Press, New York and London; Alan Fersht (1985) *Enzyme Structure and Mechanism, 2nd Edition* Alan Fersht, W. H. Freeman and Co., New York 1985).

Other assays can be utilized that more closely approximate the commercial applications contemplated for the modified enzymes of this invention. Thus, for example, hydrolases, are often a component of many of the detergent compositions that are currently on the market. One challenge facing a detergent manufacturer is the identification of new and improved enzymes and detergent compositions. Several factors can effect the determination of the "improvement" of a new enzyme (e.g. a multiply-charged chemically modified enzyme of this invention). Such factors include, but are not limited to the enzyme, the wash conditions, and the detergent composition that the enzyme is mixed with. For example, an enzyme that works well in one detergent composition may not perform as well in another. Similarly an enzyme and/or detergent composition may perform well under one set of wash conditions, e.g. Japanese (characterized by raw cottons and low surfactant levels resulting in positively charged textile surfaces), but not another set of wash conditions (e.g. North American characterized by high surfactant levels resulting in negatively charged textile surfaces).

Thus, in one embodiment this invention provides methods of assaying for a preferred enzyme and/or preferred enzyme and/or detergent composition. These methods are particularly well suited to evaluating the performance of multiply charged chemically modified mutant hydrolases of this invention. The methods preferably involve providing a swatch that typically includes a piece of material (e.g. a fabric such as cotton, wool, hemp, paper, and synthetic materials (e.g., polyester), and mixtures of natural and synthetic fibers) and a stain (e.g. blood, milk, ink, grass, gravy, chocolate, egg, cheese, clay, pigment, oil, and combinations thereof). One particularly preferred stain is a blood/milk/ink (BMI) stain. The stain is fixed to the material and a smaller swatch can, optionally, be removed from the swatch (e.g. as a test or control). An enzyme is applied to he swatch or smaller swatch and they are incubated together with or without agitation and with or without subsequent rinse.

The method can further include measuring the degree of removal of the stain from the material. In one embodiment the method can involve agitating the smaller swatch and enzyme during incubation. The enzyme can be applied to the swatch or smaller swatch in combination with one or more a detergent ingredients.

The degree of removal of the stain can then be evaluated, e.g. by visual inspection or by measuring the absorbance and/or fluorescence of, for example, ink, labeled blood, or labeled milk in a supernatant after the swatch has been incubated with an enzyme and/or detergent composition.

One aspect of this invention includes a method of agitating a microtiter plate (or other test container) to a sufficient degree to assure complete and efficient incubation of the enzyme with the smaller swatch. The methods preferably involves applying a plate sealer to the top of a microtiter plate and then clamping another lid on top of the plate sealer.

The assay; methods of this invention preferably involve the use of a treatment protocol that allows one to control of the degree of stain fixation. The use of fixed swatches leads to a dramatic improvement in the signal-to-noise ration in the wash assays. Thus, for example, untreated BMI watches washed in detergent without bleach typically release a large portion of ink, even without the help of a protease. Adding a protease leads to a small increase in ink release, but this is difficult to quantify over the large background. By controlling the degree of fixation, according to the methods of this invention, it is possible to produce swatches that release varying amounts of ink when washed in the absence of protease. Thus, the background "ink" signal can be reduced leaving an assay more sensitive to the effects of the protease. In addition, by varying the degree of fixation, one can generate stains that give optimum results under the various cleaning conditions.

The stain can be fixed to the material in a number of ways. For example, the swatch can be incubated with a cross-linking agent to fix the stain. The degree of fixation can be effected by, for example, increasing or decreasing the incubation time, varying the temperature at which the incubation takes place, and/or varying the concentration of the cross-linking chemical and/or stain agent(s).

Alternatively the assay can be optimized by using swatches having stains of known "strength". Swatches having strains of known "strength" on various types of material are commercially available (EMPA, St. Gallen, Switzerland; wfk—Testgewebe GmbH, Krefld Germany; or Center for Test Materials, Viaardingen, The Netherlands) and/or can be made by the practitioner (Morris and Prato (1982) *Textile Research Journal*, 52(4): 280–286). One particularly preferred swatch is BMI on a cotton swatch.

In one preferred embodiment of this invention, a BMI stain can be fixed to cotton with 0.0003 to 0.3% hydrogen peroxide. Other combinations include, but are not limited to, grass or spinach fixed with glutaraldehyde, gelatin and Coomassie stain fixed with glutaraldehyde, or chocolate milk and soot fixed with glutaraldehyde.

Trinitrobenzenesulfonic acid (TNBS) can be used to quantify the concentration of amino groups in the wash liquor. This can serve as a measure of the amount of protein that was removed from the swatch (see, Cayot and Tainturier (1997) *Anal. Biochem.*, 249: 184–0200). However, if a detergent or an enzyme sample leads to the formation of unusually small peptide fragments (e.g., from the presence of peptidases in the sample) then one will obtain a larger TNBS signal, i.e., more noise.

The present invention provides another and a better way to measure wash performance that is based on ink release.

For example, blood/milk/ink swatches (BMI) are used. Proteolysis of protein in the swatches leads to the release of ink particles which can be quantified by measuring the absorbance of the wash liquor. The absorbance can be measured at any wavelength between 350 and 800 nm. In a preferred embodiment, the wavelength is measured at 410 nm or 620 nm.

In a preferred embodiment of the invention, a BMI stain is fixed to cotton by applying 0.3% hydrogen peroxide to the BMI/cotton swatch for 30 minutes at 25° C. or by applying 0.03% hydrogen peroxide for 30 minutes at 60° C. Smaller swatches (e.g. approximately 0.25 inches) are cut from the BMI/cotton swatch and placed in the wells of a applying 0.3% hydrogen peroxide to the BMI/cotton swatch for 30 minutes at 25° C. or by applying 0.03% hydrogen peroxide for 30 minutes at 60° C. Smaller swatches (e.g. After placing an adhesive plate sealer onto the top of the microtiter plate, the microtiter plate is clamped to an aluminum plate and agitated for 10–200 minutes. At the end of this time, the supernatants are transferred to wells in a new microtiter plate and the absorbance of the ink at 620 nm is measured.

The performance of variant proteases (produced, for example, according to the disclosure of UUSSN 322,678) in the MSA using TNBS and ink release detection were compared. Several of these samples showed inflated wash performance when TNBS detection was used (probably due to peptidase contamination) whereas all samples result in indistinguishable signals when the absorbance of the wash liquor was measured.

The dose response of variant proteases in granular detergent under Japanese wash conditions can be examined. The absorbance of the wash liquor can be determined. Subsequently the swatches are rinsed and dried and the reflectance is measured with a flat bed scanner. An excellent correlation between both detection methods is observed which demonstrates that the absorbance of the wash liquor is a true measure of the cleaning performance. Measuring ink release is simpler, more precise, and better suited to high-throughput screening methodologies than measuring the reflectance of swatches.

To increase the throughput and make the assay suitable for screening large numbers of samples, it can be adapted to 96 well microtiter plates by using smaller (e.g. ¼")swatches. However the measurements can result in relatively large (e.g. >10%) standard deviations. It has been observed that the signal is dependent on the orientation of the swatches in the wells (horizontal versus vertical) which indicates that mixing was insufficient. To address this issue, a plate holder in which the microtiter plate is sandwiched between two outer plates (e.g. aluminum plates) can be constructed. The device can be mounted in a commercial incubator shaker. Setting the shaker to 400 rpm resulted in very efficient mixing, while leakage or cross-contamination between the wells was effectively prevented by the holder.

It will be appreciated that the forgoing assays are not limited to textile washing. Similar assays can be performed for essentially any other cleaning application. Thus, for example, the present invention can be used to determine a preferred enzyme and/or detergent composition for dish washing, for example, using a BMI stain on a suitable substrate such as cloth, plastic, glass, or ceramic. It will be appreciated that the foregoing protocol is exemplary and not limiting and numerous modifications and variants can be performed with only routine experimentation by one of ordinary skill in the art.

Production of multiply-charged chemically modified mutant enzymes and screening for particular activities of such modified enzymes is amenable to high throughput methodologies. Typically such methodologies utilize robotics to automate and speed the production and screening of large numbers of compounds. In efficient high throughput screening system, typically hundreds of thousands of reactants/reactions can be screened in a few days with only routine operator involvement. High throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

IV. Uses of the CMMs of this Invention

The multiply-charged chemically modified mutant enzymes of this invention can be used in a wide variety of applications. The applications can be the same as those in which "conventional" enzymes of the same type are used, the multiply charged variants of this invention offering improved performance (e.g. stability, specificity, activity, etc.). In preferred embodiments, the enzymes of this invention will be used where enhanced performance on charged substrates is desired.

Thus, for example, the modified hydrolases of this invention (e.g. proteases, cellulases, amylases, laccases, lipases, etc.) may be formulated into known powdered and liquid detergents. The particular multiple-charged variant will depend on the anticipated wash conditions. Thus, for example, in Japan where wash conditions typically involve naked cotton and low surfactant concentrations, the cloth surface tends to accumulate a positive charge and negative multiply charged modified enzymes are desirable. Conversely in Europe where high surfactant use results in negatively charged surfaces, positive multiply charged modified enzymes are desirable.

Typical detergent compositions will have contain the multiply charged enzymes at levels of about 0.01 to about 5%, preferably about 0.1% to about 0.5%, by weight. These detergent cleaning compositions or additives can also include other enzymes components such as builders and stabilizers, etc.

In particularly preferred embodiments, the multiply charged proteases, more preferably multiply charged subtilisins are used in formulating various detergent compositions. A number of known compounds are suitable surfactants useful in such detergent compositions. These include nonionic, anionic, cationic, anionic, or zwitterionic detergents (see, e.g., U.S. Pat. Nos. 4,404,128, and 4.261,868). A suitable detergent formulation is that described in example 7 of U.S. Pat. No. 5,204,015. The modified enzymes of this invention may provide improved was performance in a detergent composition (as compared to previously known additives). Improves wash performance typically refers to increased cleaning of certain modified enzyme-sensitive stains such as grass or blood, as determined by a standard evaluation procedure (e.g. light reflectance) after a standard wash cycle.

The art is familiar with the different formulations that can be used as cleaning compositions. In addition to typical compositions, it is readily understood that the modified enzymes of the present invention may be used for any purpose that the native or wild-type enzymes are used. Thus, these modified enzymes can be used, for example, in bar or liquid soap applications, dish care formulations, contact lens cleaning solutions or products, peptide synthesis, feed applications such as feed additives or preparation of feed additives, waste treatment, textile application such as the treatment of fabrics, and as fusion-cleavage enzymes in protein production.

In another preferred embodiment, the modified enzymes of this invention are used in a method of treating a textile. The methods involve contacting a multiply charged chemically modified mutant enzyme of this invention with a textile under conditions effective to produce a textile resistant to certain enzyme-sensitive stains (e.g. grass or blood stains). The method can be used to treat, for example, silk or wool. Enzyme treatments of such fabrics are know to those of skill in the art and are described for example in Research Disclosure 216,034, European Patent application No: 134,267, U.S. Pat. No. 4,533,359, and European Patent application 3244,259.

In still another embodiment, the modified enzymes of this invention are used in the preparation of an animal feed, for example, a cereal-based feed. The enzyme can be incorporated into essentially any cereal feed, e.g. a cereal comprising one or more of wheat, barley, maize, sorghum, rye, oats, triticale, and rice. Although the cereal component of a cereal-based feed constitutes a source of protein, it is usually necessary to include species of supplementary protein in the feed such as those derived form fish meal, meat, or vegetables. Sources of vegetable proteins include, but are not limited to soybeans, rape seeds, canola, soybean meal, rapeseed meal, and canola meal.

The inclusion of a multiply charged modified enzyme in an animal feed can enable the crude protein value and/or the digestibility and/or the amino acid content of the feed to be increased. This permits a reduction in the amounts of alternative protein sources and/or amino acid supplements that are added to the feed.

The foregoing description of uses for the modified mutant enzymes of this invention is illustrative and not intended to create any special use limitation. One will appreciate that the uses of the enzymes of this invention are myriad and not to be confined to the uses enumerated herein.

V. Kits and Products Containing Chemically Modified Mutants

In still another embodiment, this invention provides kits for synthesizing and/or screening multiply charged modified mutant enzymes of this invention. Such kits preferably include one or more mutant serine hydrolases having one or more amino acid residues substituted with a cysteine as described herein and/or include one or more multiply-charged methane sulfonate reagents as described herein that can be used to derivatized the mutant serine hydrolase. Such kits may additionally include one or more reagents and/or apparatus for performing such derivitizations.

In addition, the kits can include appropriate substrates and/or reactants for screening the chemically modified mutant enzyme for one or more desired activities as described herein.

In another embodiment this invention provides kits for the use of the modified mutant enzymes described herein. Such kits preferably contain one or more containers containing one or more of the chemically modified mutant serine hydrolases as described herein. Such kits can also include appropriate reagents and/or substrates to use the modified enzymes in one or more of the reactions described herein.

In addition, the kits may include instructional materials containing directions (i.e., protocols) preparation of the multiply charged enzymes of this invention and/or for their use. Thus, for example, in one preferred embodiment, the instructional materials provide protocols derivatizing the mutant enzyme with one or more of the multiply charged methane sulfonate reagents described herein. In another embodiment, the instructional materials may provide protocols describing the use of the modified enzyme as an additive to a cleaning agent (e.g. a laundry detergent). While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

The Controlled Introduction of Multiple Negative Charge at Single Amino Acid Sites in Subtillsin *Bacillus lentus*

Using the X-ray structure of SBL (the coordinates of SBL have been deposited at the Protein Databank at Brookhaven under the code 1JEA) (FIG. 1) as our guide, four sites were chosen for mutation because of their seminal positions in the active site. Two of these, N62 (subtilisin BPN' numbering) and L217, occupy positions that are equidistant from S221 of the catalytic triad, in the $S_2$ (Nomenclature of Schechter and Berger (1967) *Biochem. Biophys. Res. Commun.* 27: 157–162) and $S_1'$ pockets respectively. The other two sites, S156 and S166, are located at the base of the $S_1$ pocket and their side chains are directed towards SBL's surface and catalytic triad respectively. The MTS reagents $1^a$-e were selected to modify these positions.

Results And Discussion

Synthesis of Carboxyalkyl Methanethiosulfonates 1b–e

Previous work (Kenyon and Bruice (1977) *Methods Enzymol.* 47: 407–430; Berglund et al. (1997) *J. Am. Chem. Soc.* 119: 5265–5266) has demonstrated that, of the methods available (Douglass and Farah (1959) *J. Org. Chem.* 24: 973–975; Levitt and Levitt (1972) *J. Org. Chem.* 37: 332–334; Weidner and Block (1972) *J. Med. Chem.* 15: 564–567; Palumbo and Caputo (1981) *Synthesis* 888–890; Block and Zhao (1992) *J. Org. Chem.* 57: 5815–5817; Billard et al. (1996) *J. Org. Chem.* 61: 7545–7550), direct nucleophilic displacement of a primary alkyl bromide by methanethiosulfonate ion provides the most efficient method for the preparation of alkyl methanethiosulfonates. This general method was therefore adopted as the basis for the preparation of all of 1b–e. The aliphatic monocarboxylate MTS 1b (U.S. Pat. No. 4,879,249) was prepared from 5-bromopentanoic acid and $NaSSO_2CH_3$ in 80% yield.

Figure 2:
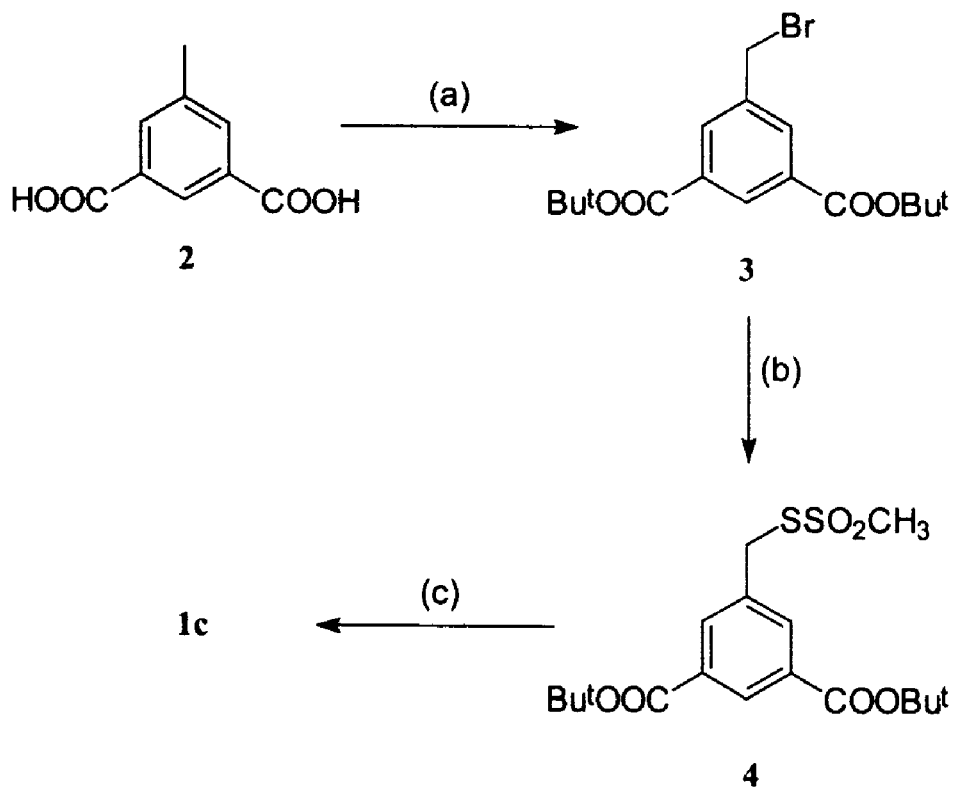
FIG. 2 shows scheme 2 for the preparation of the aromatic dicarboxylate MTS 1c from toluene-3,5-dicarboxylic acid (2) via a precursor benzylic bromide 3. (a) (i) $Im_2CO$, DMF, 40° C. then DBU, t-BuOH, 84% (ii) NBS, azobis (cyclohexanecarbonitrile), $CCl_4$, Δ, 96% (b) $NaSSO_2CH_3$, DMF, 50° C., 60% (c) $CF_3COOH$, $CH_2Cl_2$, 91%.

The aromatic dicarboxylate MTS 1c was prepared from toluene-3,5-dicarboxylic acid (2) via a precursor benzylic bromide 3 as shown in Scheme 2 (FIG. 2). Treatment of 3 with $NaSSO_2CH_3$ gave the protected aromatic MTS 4 in 60% yield. Hydrolysis of 4 with TFA gave 1c as a white solid (91% yield, 44% overall yield from 2).

Figure 3:
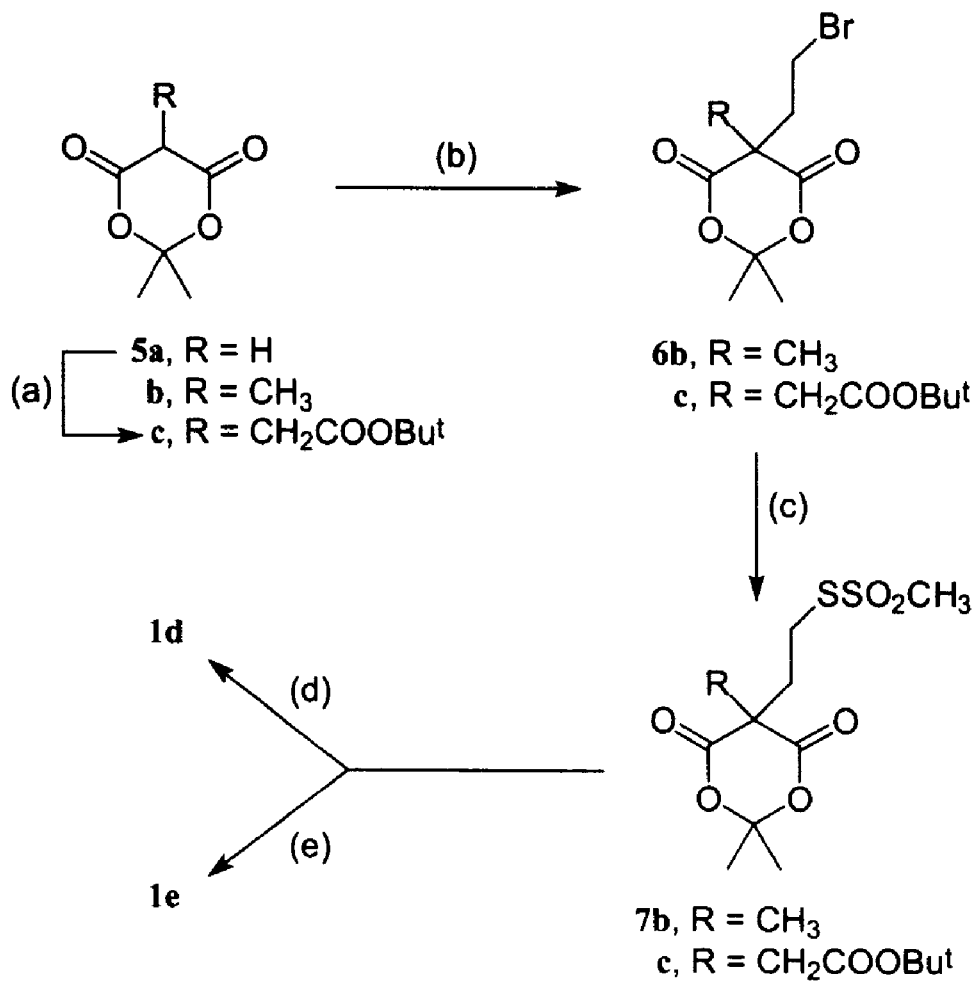
FIG. 3 shows scheme 3 illustrating the preparation of the aliphatic di- and tricarboxylates 1d,e were prepared from Meldrum's acid (5a) using 1,2-dibromoethane to introduce a brominated linker group. (a) $K_2CO_3$, DMF then $BrCH_2COOBu^t$, 59% (b) $K_2CO_3$, DMF then $Br(CH_2)_2Br$, 71% for $^{6b}$, 66% for 6c (c) $NaSSO_2CH_3$, DMF, 50° C., 83% for $^{7b}$, 86% for 7c (d) Dowex 50W($H^+$), p-dioxan, $H_2O$, 79% (e) $CF_3COOD$, $D_2O$, 50° C., 70%.

The aliphatic di- and tricarboxylates 1d,e were prepared from Meldrum's acid (5a) using 1,2-dibromoethane to introduce a brominated linker group as shown in Scheme 3 (FIG. 3). The low $pK_a$ of 5a (Arnett et al. (1984) *J. Am. Chem. Soc.* 106 :6759–6766; Arnett and Harrelson (1987) *J. Am. Chem. Soc.* 109: 809–812) allowed the use of mildly basic conditions compatible with this choice of linker. For the sake of simplicity, we chose methyl Meldrum's acid (5b) as a starting material for 1d in which one alkylation site is blocked as a methyl group. Direct alkylation of 5a with 1,2-dibromoethane led only to the formation of a spirocyclopropane derivative, the product of intramolecular cyclization, in low yield. For a recent analysis of the high propensity of the anion of 5a to form cyclic products with $\alpha,\omega$-dihalides see Ridvan (1997) *J. Tetrahedron* 53: 14793–14806. The synthesis of 1e utilized this position to introduce a third carboxylate moiety.

Alkylation of 5b with 1,2-dibromoethane afforded bromide 6b in 71% yield. Treatment of 6b with $NaSSO_2CH_3$ in DMF at 50° C. led to the displacement of the remaining bromide and resulted in the formation of protected dicarboxylate MTS 7b. Hydrolysis of 7b using acidic ion exchange resin allowed the successful formation of the aliphatic diacidic MTS 1d (79% yield, 37% overall yield from 5b).

The synthesis of the triacidic reagent 1e required the construction of a protected tricarboxylate 5c before elaboration. Alkylation of Meldrum's acid (5a) with tert-butyl bromoacetate allowed the formation of 5c with moderate selectivity in 59% yield. Elaboration of tricarboxylate 5c was carried out using 1,2-dibromoethane and then $NaSSO_2CH_3$ in an analogous manner to that used for the synthesis of 1d and gave protected tricarboxylate MTS 7c in 57% yield over 2 steps. Complete deprotection of 7c using $CF_3COOD$ in $D_2O$ was followed by $^1H$ NMR, and resulted in the formation of target 1e (70% yield, 23% overall yield from 5a).

Preparation of Chemically Modified Mutants (CMMs)

MTS reagents 1a–e were used to modify the chosen SBL cysteine mutants, N62C, S156C, S166C and L217C under conditions described previously (Berglund et al. (1997) *J. Am. Chem. Soc.* 119: 5265–5266; Stabile et al. (1996) *Bioorg. Med. Chem. Lett.* 6: 2501–2512; DeSantis et al. (1998) *Biochem.* 37: 5968–5973). These reactions proceeded rapidly and quantitatively, as judged by the monitoring of changes in specific activity and by titration of free thiols with Ellman's reagent (Ellman et al. (1961) *Biochem. Pharmacol.* 7: 88–95), respectively. The structure of the charged CMMs was confirmed by ES-MS. Non-reducing native PAGE was used to determine the purity of all the enzymes, which appeared as single bands. Consistent with the introduction of negative charge, each of the CMMs showed retarded mobility in the direction of the cathode relative to WT. The active enzyme concentration of the resulting CMM solutions was determined by active site titration with $\alpha$-toluenesulfonyl fluoride (PMSF) using a fluoride ion-sensitive electrode (Hsia et al. (196) *J. Anal. Biochem.* 242: 221–227).

Kinetic Effects of Site Specific Modification

The effects of modification upon SBL were assessed by the determination of $k_{cat}$ and $K_M$ for the hydrolysis of succinyl-AAPF-p-nitroanilide (Suc-AAPF-pNA). Our usual assay pH of 8.6 ensured complete ionization of the unnatural amino acid side-chains introduced. The kinetic parameters of the 20 CMMs generated are compared with those of Wt and unmodified mutants in Table 1 and FIG. 4.

TABLE 1

Kinetic Parameters[a] for Modified Enzymes

| Entry | Enzyme | Pocket | R[c] | Level of Charge | $k_{cat}$ ($s^{-1}$) | $K_M$ (mM) | $k_{cat}/K_M$ ($S^{-1}$ $mM^{-1}$) |
|---|---|---|---|---|---|---|---|
| 1 | SBL-WT | — | — | — | 153 ± 4 | 0.73 ± 0.05 | 209 ± 15 |
| 2 | N62C | $S_2$ | H | 0 | 174 ± 9 | 1.90 ± 0.20 | 92 ± 11 |
| 3 | | | a | 1 | 119 ± 4 | 0.93 ± 0.07 | 128 ± 11 |
| 4 | | | b | 1 | 106 ± 2 | 1.01 ± 0.05 | 105 ± 6 |
| 5 | | | c | 2 | 113 ± 7 | 1.00 ± 0.10 | 113 ± 13 |
| 6 | | | d | 2 | 90 ± 4 | 1.47 ± 0.14 | 61 ± 6 |
| 7 | | | e | 3 | 129 ± 3 | 1.46 ± 0.06 | 88 ± 4 |
| 8 | L217C | $S_1'$ | H | 0 | 41 ± 1 | 0.80 ± 0.04 | 51 ± 3 |
| 9 | | | a | 1 | 89 ± 6 | 1.80 ± 0.20 | 50 ± 6 |
| 10 | | | b | 1 | 54 ± 1 | 1.03 ± 0.06 | 52 ± 3 |
| 11 | | | c | 2 | 69 ± 2 | 0.81 ± 0.06 | 85 ± 7 |
| 12 | | | d | 2 | 63 ± 2 | 1.65 ± 0.11 | 38 ± 3 |
| 13 | | | e | 3 | 55 ± 2 | 1.48 ± 0.08 | 37 ± 3 |
| 14 | S156C | $S_1$ | H | 0 | 125 ± 4 | 0.85 ± 0.06 | 147 ± 11 |
| 15 | | | a | 1 | 87 ± 2 | 1.20 ± 0.07 | 73 ± 5 |
| 16 | | | b | 1 | 76 ± 1 | 1.08 ± 0.04 | 70 ± 3 |
| 17 | | | c | 2 | 61 ± 1 | 1.39 ± 0.10 | 44 ± 3 |
| 18 | | | d | 2 | 53 ± 1 | 1.67 ± 0.06 | 32 ± 1 |
| 19 | | | e | 3 | 74 ± 2 | 1.87 ± 0.08 | 39 ± 2 |
| 20 | S166C | | H | 0 | 42 ± 1 | 0.50 ± 0.05 | 84 ± 9 |
| 21 | | | a | 1 | 25 ± 1 | 1.34 ± 0.08 | 19 ± 1 |
| 22 | | | b | 1 | 48 ± 1[b] | 1.52 ± 0.06 | 31 ± 1[b] |
| 23 | | | c | 2 | 47 ± 3 | 1.60 ± 0.20 | 29 ± 4 |
| 24 | | | d | 2 | 67 ± 2 | 2.26 ± 0.10 | 30 ± 2 |
| 25 | | | e | 3 | 76 ± 2 | 2.46 ± 0.11 | 31 ± 2 |

[a]Michaelis-Menten constants were measured at 25° C. according to the initial rates method in 0.1 M Tris-HCl buffer at pH 8.6, 0.005% Tween 80, 1% DMSO, Suc-AAPF-pNA as the substrate.

TABLE 1-continued

Kinetic Parameters[a] for Modified Enzymes

| Entry | Enzyme | Pocket | R[c] | Level of Charge | $k_{cat}$ (s$^{-1}$) | $K_M$ (mM) | $k_{cat}/K_M$ (S$^{-1}$ mM$^{-1}$) |
|---|---|---|---|---|---|---|---|

[b]Based on total protein concentration. Certain inconsistencies between active enzyme concentration as determined by active site titration with PMSF (Hsia et al. (1996) *J. Anal. Biochem.* 242: 221–227) and total protein concentration have been reported for negatively charged mutants of SBL. These are characterized by sluggish fluoride ion concentration bursts and high rates of background PMSF hydrolysis. Active enzyme concentration values for S166C-b were low and gave rise to an anomalous value for kcat (270 ± 5 s-1). Consequently the value shown was calculated using total protein concentration as determined by absorbance at 280 nm (e280 = 23000 M-1 cm-1) (Grøn et al. (1990) *Eur. J. Biochem.* 194: 897–901). The KM value determined (1.52 ± 0.06 mM) is not concentration dependent.

[c]a = sulfonatoethyl;
b = 4-carboxybutyl;
c = 3,5-dicarboxybenzyl;
d = 3,3-dicarboxybutyl;
e = 3,3,4-tricarboxybutyl.

Position 62 in the $S_2$ pocket is the most tolerant of mutation and modification (FIG.4A) and mutation to cysteine reduces $k_{cat}/K_M$ by only a factor of 2 (Table 1, Entry 2). Upon modification, activity is partially restored and values of $k_{cat}/K_M$ for N62C-a,b,c are raised approximately 1.5-fold relative to N62C (Table 1, Entries 3–5). Modifications with aliphatic di- and tri-carboxylate MTS reagents 1d,e elicit further drops in $k_{cat}/K_M$, with N62C-d being 3.5-fold lower than WT. However, despite the increased charge, this $k_{cat}/K_M$ drop is less marked for N62C-e.

The deleterious effect of negative charges in the $S_2$ pocket upon $k_{cat}$ is apparent in the 1.3-fold decrease observed for N62C-a (Table 1, Entry 3) relative to WT. However, as the level of negative charge increases, $k_{cat}$ values do not decrease further to any significant extent. In fact, of all the CMMs, the $k_{cat}$ level of N62C-e (129 s$^{-1}$, Table 1, Entry 7) is the highest. In contrast, $K_M$ values increase continually with each additional charge, reaching values for N62C-d (Table 1, Entry 6) and N62C-e (Table 1, Entry 7) that are 2-fold higher than WT.

The effects of mutation at position 217 in the $S_1'$ pocket (FIG. 4B) are intrinsically more dramatic than at all three other sites since the value of $k_{cat}/K_M$ for L217C is 4-fold lower than WT. The introduction of a single negative charge only affects $k_{cat}/K_M$ a little and leads to near-identical $k_{cat}/K_M$ values for L217C-a,b (Table 1, Entries 9,10). As negative charge increases further, two opposite trends are observed, with the $k_{cat}/K_M$ value for aromatic L217C-e being raised 1.6-fold relative to L217C-a,b, while those for aliphatic L217C-d,e are reduced by 1.4-fold.

These slight $k_{cat}/K_M$ changes seen at position 217 are the result of larger, but counteracting changes in each of $k_{cat}$ and $K_M$. For example, while L217C-a has the highest value of $k_{cat}$, it also has the highest $K_M$ value (both 2.2-fold higher than L217C). As at position 62, when the level of negative charge increases, from L217C-a to L217C-e, $k_{cat}$ values decrease only slightly and remain 1.3- to 1.7-fold higher than L217C (Table 1, Entries 10–13). $K_M$ values increase unevenly to 2-fold higher than WT. Interestingly, the underlying cause of the out-of-line $k_{cat}/K_M$ of L217C-c is an unusually low $K_M$ (0.81 mM, Entry 11), which may be a consequence of complementary aromatic interactions between the substrate and the phenyl ring of side chain c.

Figure 4A:
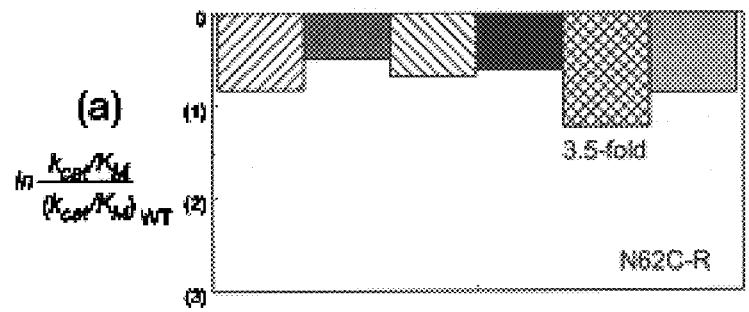
FIGS. 4A, 4B, 4C, and 4D illustrate altered specificity patterns relative to WT as the level of negative charge increases in N62C, L271 C, S156C and S166C mutants and CMMs with suc-AAPF-pNA as the substrate.
Figure 4B:
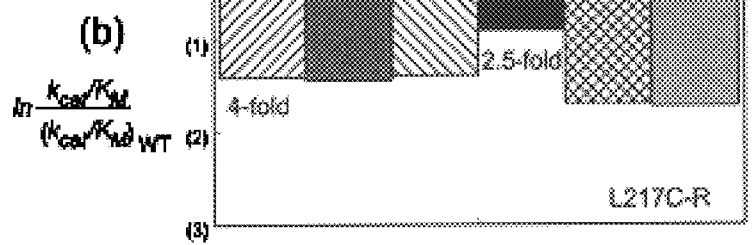
Figure 4C:
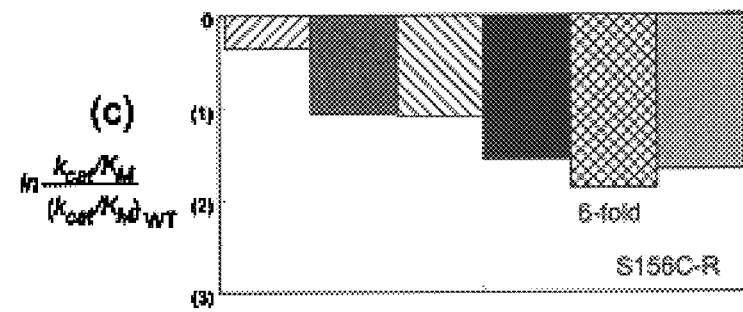
Figure 4D:
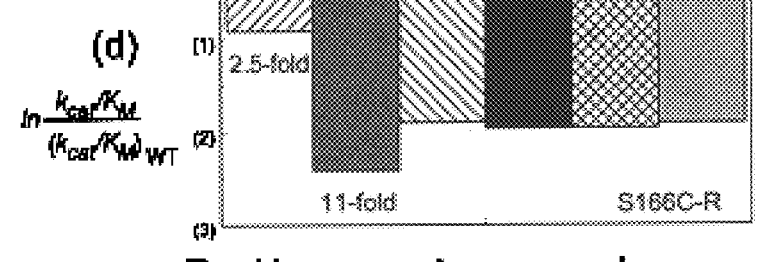

The effects of mutation and modification at positions 156 and 166 in the $S_1$ pocket are shown in FIGS. 4C and 4D. Mutation at position 156 to cysteine causes a 1.4-fold drop in $k_{cat}/K_M$ (S156C, Table 1, Entry 14). From S156C-a to S156C-d $k_{cat}/K_M$ decreases monotonically to a value that is 6-fold lower than WT. The additional negative charge present in S156C-e partially restores this value, to only 5.4-fold lower than WT.

Mutation and modification at position 166 leads to the least active negatively charged CMMs with $k_{cat}/K_M$s 6- to 11-fold lower than WT. This partly reflects the intrinsically lower $k_{cat}/K_M$ value of the unmodified mutant S166C, which is already 2.5-fold lower than WT. However, the presence of the sulfonatoethyl side chain in S166C-a causes a dramatic drop to a value that is 11-fold lower than WT. $k_{cat}/K_M$ is increased 1.5-fold for S166C-b and remains steady as the level of negative charge increases from S166C-c to S166C-e.

The $k_{cat}$ values for S156C and S166C CMMs are similar to those found for L217C CMMs, typically 2 to 2.5-fold lower than WT. As at positions 62 and 217, the detrimental effect of a single negative charge on $k_{cat}$ is not amplified by the introduction of additional negative charges. In fact, $k_{cat}$ values for S166C CMMs increase steadily from 6-fold lower than WT for S166C-a (Table 1, Entry 21) to 2-fold lower than WT for S166C-e (Table 1, Entry 25).

The $K_M$ values for both S156C and S166C CMMs increase steadily with increasing negative charge and are largest for S166C-e ($K_M$ 2.46 mM, 3.5-fold higher than WT, Table 1, Entry 25). Consistent with its surface-exposed nature these effects are less pronounced at position 156 with $K_M$ increasing to only 2.5-fold higher than WT for S156C-e (Table 1, Entry 19).

Kinetic Effects of Negative Charge

Figure 5:
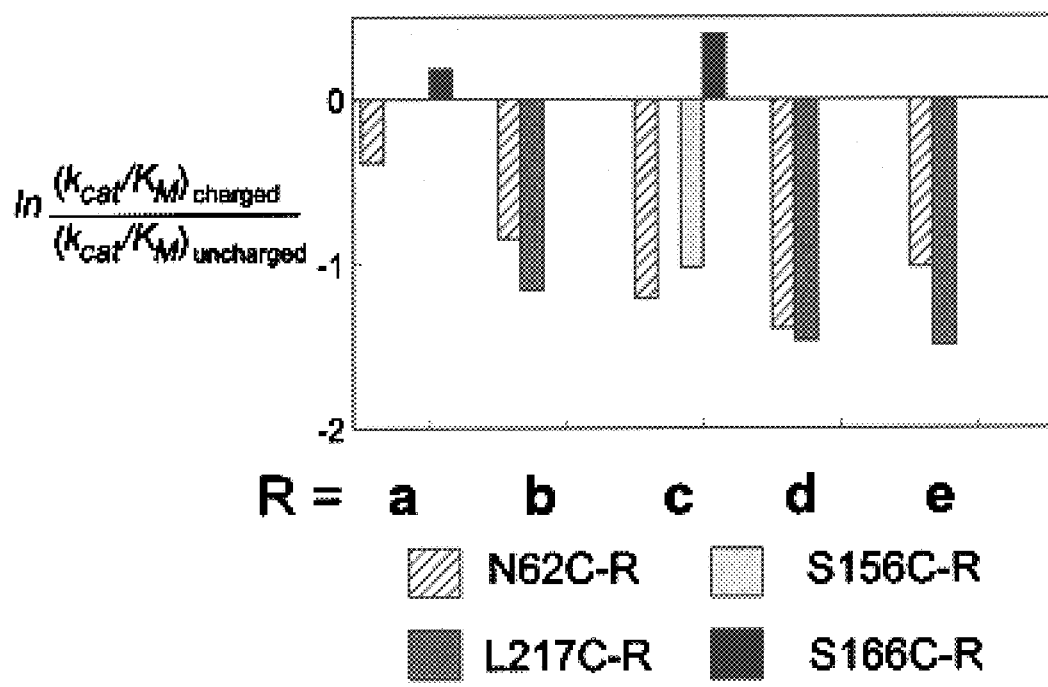
FIG. 5 illustrates the effects of introducing negative charge to CMMs: In ($k_{cat}/K_M$), with suc-AAPF-pNA as the sabstrate, of the negatively charged N62C, L217C and S156C CMMs decreases relative to that of near-isosteric uncharged CMMs as the level of negative charge increases (from side chain a to e). In contrast, this value for the corresponding S166C CMMs increases with increasing negative charge.

To separate the contribution of electrostatics from steric effects, a comparison of these charged CMMs with those containing sterically similar uncharged side chains was made. (The following kinetic parameters for the previously prepared (Berglund et al. (1997) *J. Am. Chem. Soc.* 119: 5265–5266; DeSantis et al. (1998) *Biochem.* 37: 5968–5973) near isosteric CMMs were determined under the conditions described in the experimental section; N62C-S-ethyl $k_{cat}$ 104±2 s$^{-1}$, $K_M$ 0.55±0.04 mM, $k_{cat}/K_M$ 189±14 s$^{-1}$mM$^{-1}$; N62C-S-benzyl $k_{cat}$ 129±3 s$^{-1}$, $K_M$ 0.34±0.03 mM, $k_{cat}/K_M$ 379±37 s$^{-1}$mM$^{-1}$; N62C-S-n-pentyl $k_{cat}$ 184±5 s$^{-1}$, $K_M$ 0.75±0.05 mM, $k_{cat}/K_M$ 245±18 s$^{-1}$mM$^{-1}$; L217C-S-n-pentyl $k_{cat}$ 87±3 s$^{-1}$; $K_M$ 0.52±0.05 mM, $k_{cat}/K_M$ 167±17 s$^{-1}$mM$^{-1}$; S156C-S-benzyl $k_{cat}$ 72±2 s$^{-1}$; $K_M$ 0.59±0.05 mM, $K_{cat}/K_M$ 122±11 s$^{-1}$mM$^{-1}$; S166C-S-ethyl $k_{cat}$ 11.8±0.5 s$^{-1}$; $K_M$ 0.76±0.08 mM, $k_{cat}/K_M$ 15.5±1.8 s$^{-1}$mM$^{-1}$; S166C-S-benzyl $k_{cat}$ 23.1±0.5 s$^{-1}$; $K_M$ 1.17±0.06 mM, $k_{cat}/K_M$ 19.7±1.1 s$^{-1}$mM$^{-1}$.) For example, N62C-a was compared with N62C-S-ethyl, N62C-b,d,e were compared with N62C-S-n-pentyl and N62C-c was compared with N62C-s-benzyl. FIG. 5 illustrates the results of introducing charge to these near-isosteric systems. This provides an estimates of the effect of negative charge upon the kinetics of SBL when corrected for underlying steric and hydrophobic effects.

Two differing trends emerge from FIG. 5. At positions 62, 217 and 156, the electrostatic contribution of each of side chains a–e is detrimental to $k_{cat}/K_M$. The reductions caused are similar for each side chain, vary little from site to site and increase with the level of negative charge introduced. These reduced $k_{cat}/K_M$ values resulting from the introduction of negative charge are consistent with earlier findings (Ballinger et al. (1995) Biochem. 34; 13312–13319; Berglund et al. (1997) J. Am. Chem. Soc. 199: 5265–5266; Stabile et al. (1996) Bioorg. Med. Chem. Lett.6: 2501–2512; DeSantis et al. (1998) Biochem. 37: 5968–5973.). Such effects may be attributed, in part, to destabilization of the tetrahedral oxyanion intermediate that is formed in the rate limiting step of catalysis (Jackson and Fersht (1993) Biochem. 32: 13919–13916).

In contrast, the introduction of negative charge at position 166 partially restores some of the activity lost through the introduction of near-isosteric uncharged side chains. Therefore the drastically lowered $k_{cat}/K_M$s of CMMs S166C-a–e relative to WT are, in fact, a result of steric or hydrophobic effects. Mutation analysis of subtilisin BPN' has shown that $k_{cat}/K_M$ decreases dramatically when the optimal binding volume of the $S_1$-pocket is exceeded (Estell et al. (1986) Science 233:659–663). The effect of introducing even small groups at position 166 of SBL (this space is more limited in SBL than in subtilisin BPN' as the peptide backbone that makes up the wall of the $S_1$ pocket contains four less amino acid residues) is to fill the $S_1$-pocket and this dramatically decreases $k_{cat}/K_M$. For example, uncharged CMM S166C-S-ethyl has a $k_{cat}/K_M$ 13.5-fold lower than WT. Molecular mechanics analysis of S166C CMMs has shown that charged side chains introduced at position 166 may orientate themselves towards external solvent (DeSantis et al. (1998) Biochem. 37: 5968–5973). This serves to reduce the volume of the $S_1$ pocket that is occupied by the side chain. The existence of such an orientation for S166C-a–e, which is lacking in uncharged CMM counterparts, might, in part, explain the beneficial effects of introducing charge. As a result, charged CMM S166C-S-EtSO$_3^-$, side chain a, has a $k_{cat}/K_M$ only 11-fold lower than WT.

Conclusions

In summary, we have devised short and efficient synthetic routes to three novel multiply charged methanethiosulfonates, 1c, d and e. Such compounds, as well as being of interest in our approach to the controlled tailoring of enzyme activity, may prove useful in the study of ion channels. The use of MTS reagents in techniques such as the substituted-cysteine accessibility method (SCAM) (Akabas et al. (1992) Science 258: 307–310; Akabas et al. (1994) Neuron 13: 919–927; Akabas et al. (1994) J. Biol. Chem. 269: 14865–14868) has allowed aspects of membrane ion channel topology and conformation to be determined. In particular the use of charged MTS reagents has given an invaluable insight into ion specificity (Cheung and Akabas (1997) J. Gen. Physiol 109: 289–299) and mechanism of action (Stauffer and Karlin (1994) Biochem. 33: 6840–6849; Yang et al. (1996) Neuron 16: 113–122; Holmgren et al. (1996) Neuropharmacol. 35: 797–804; Huynh et al. (1997) J. Gen. Physiol. 110: 229–242; Rassendren et al. (1997) EMBO J. 16: 3446–3454).

Using our established methodology, we selectively modified the cysteine thiols of SBL mutants, N62C, S156C, S166C, and L217C, with these reagents. Without exception, mutation and modification at all four sites led to reduced catalytic efficiency in the hydrolysis of Suc-AAPF-pNA. However these reductions do not exceed 11-fold relative to WT and the lowest $k_{cat}$ values determined were only 6-fold reduced. This reduced efficiency is manifested largely through decreased binding interactions, i.e., decreased $K_M$ values, that increase with the level of charge introduced. In contrast, $k_{cat}$ values corresponding to the introduction of multiple charge are similar to, if not higher than, those for single charge. Comparison with near-isosteric uncharged CMMs revealed that electrostatic effects are paramount at positions 62, 217 and 156. However at position 166 steric effects dominate and the introduction of negative charge is, in fact, beneficial.

Experimental

Mutants of Subtilisin Bacillus lentus (SBL) were generated, and WT and mutant enzymes purified as described previously (Stabile et al. (1996) Bioorg. Med. Chem. Lett.6: 2501–2512; DeSantis et al. (1998) Biochem. 37: 5968–5973). NaSSO$_2$CH$_3$ (Kenyon and Bruice (1977) Methods Enzymol. 47: 407–430) (mp 269–269.5° C. (dec.) [lit. (Id.), m.p. 272–273.5° C.]) and toluene-3,5-dicarboxylic acid (2) (Fittig et al. (1868) Anal. Chem. 147: 292–312) (mp 294.5–296° C. (water) [lit. (Id.), m.p. 287–288° C.]) were prepared according to literature methods. DMF was distilled under N$_2$ from CaH$_2$ and stored over molecular sieve under N$_2$ before use. CCl$_4$ was fractionally distilled before use. Sulfonatoethyl methanethiosulfonate (1a) was purchased from Toronto Research Chemicals (2 Brisbane Rd., Toronto, ON, Canada). All other chemicals were used as received from Sigma-Aldrich or Baker. All flash chromatography was performed using silica gel (Whatman, 60 Å, 230–400 Mesh). Melting points were determined using an Electrothermal IA9000 series digital melting point apparatus and are uncorrected. IR spectra were recorded on Bomem MB or Perkin-Elmer FTIR Spectrum 1000 spectrophotometers. $^1$H NMR and $^{13}$C NMR spectra were recorded on a Varian Gemini 200 NMR spectrometer at 200 and 50.3 MHz respectively. ES-MS data were acquired using a PE SCIEX API III Biomolecular mass spectrometer. All other MS and HRMS data, were acquired using Micromass 70–250S or Micromass ZAB-SE mass spectrometers according to the ionization methods indicated. Microanalyses were performed by Canadian Microanalytical Service Ltd. (Delta, B.C., V4G 1G7, Canada). Solvents were removed in vacuo.

4-Carboxybutyl Methanethiosulfonate (1b)

A solution of 5-bromopentanoic acid (1.238 g, 6.84 mmol) and NaSSO$_2$CH$_3$ (0.916 g, 6.84 mmol) in DMF (6 mL) was heated at 70° C. under N$_2$. After 2 h the solution was cooled, water (15 mL) added and the resulting mixture extracted with ether (30 mL×3). The organic fractions were combined, washed with brine, dried (MgSO$_4$), filtered and the solvent removed. The residue was purified by flash chromatography (ether: CH$_2$Cl$_2$: AcOH, 40:120:1) to give 1b (1.167 g, 80%) as a white solid; mp 61–62.5° C. [lit. (U.S. Pat. No. 4,879,249), mp 69–71° C.]; IR (KBr) 1703 cm$^{-1}$ (C=O), 1311, 1125 cm$^{-1}$ (S—SO$_2$); $^1$H NMR (CDCl$_3$) δ1.70–2.00 (m, 4H, H-2, H-3), 2.43 (t,J 6.9 Hz, 2H, H-4), 3.20 (t,J 6.8 Hz, 2H, H-1), 3.34 (s, 3H, SSO$_2$CH$_3$), 8.82 (br s, 1H, COOH); $^{13}$C NMR (CDCl$_3$) δ23.4, 28.9, 33.1, 35.9 ((CH$_2$)$_4$), 50.7 (SSO$_2$CH$_3$), 178.7 (COOH); MS m/z (EI+): 213 (M+H$^+$, 2), 195 (M+H$^+$—H$_2$O, 11), 133 (50), 115 (M$^+$—CH$_3$SO$_2$—H$_2$O, 100%); HRMS m/z (EI+): Found 213. 0251 (M+H$^+$); C$_6$H$_{13}$O$_4$S$_2$ requires 213. 0255.

3,5-Dicarboxybenzyl Methanethiosulfonate (1c)

1,1'-Carbonyldiimidazole (6.67 g, 0.0411 mol) was added to a solution of toluene-3,5-dicarboxylic acid (2) (3.364 g, 0.0187 mol) in DMF (30 mL) and the resulting mixture stirred at 40° C. under $N_2$. After 1.5 h DBU (6.15 mL, 0.041 mol) and t-BuOH (7.7 mL, 0.0822 mol) were added. After 24 h the solution was cooled, ether (150 mL) added and the mixture acidified (HCl (aq.), 1.5 M). The ethereal layer was separated and the aqueous layer further extracted (ether, 150 mL). The organic fractions were combined, washed with water and 10% $K_2CO_3$ (aq.), dried ($MgSO_4$), filtered and the solvent removed. The residue was purified by flash chromatography (EtOAc:hexane, 1:50) to afford a colorless oil which solidified upon standing to give di-tert-butyl toluene-3,5-dicarboxylate (4.58 g, 84%) as a white solid; mp 86.5–87.5° C. (hexane); IR (film) 1712 $cm^{-1}$ (C=O), 1606, 1476 $cm^{-1}$ (Ar C=C); $^1$H NMR (CDCl$_3$) δ1.60 (s, 18H, C(CH$_3$)$_3$), 2.43 (s, 3H, CH$_3$), 7.95 (br s, 2H, H-2, H-6), 8.38 (br s, 1H, H-4); $^{13}$C NMR (CDCl$_3$) δ21.4 (CH$_3$), 28.2 (C(CH$_3$)$_3$), 81.4 (C(CH$_3$)$_3$), 127.7, 132.1, 133.7, 138.1 (Ar), 165.2 (COO).

NBS (0.521 g, 2.93 mmol) and 1,1'-azobis(cyclohexanecarbonitrile) (30 mg, 0.12 mmol) were added to solution of this diester (0.712 g, 2.44 mmol) in CCl$_4$ (10 mL) and heated under reflux under $N_2$. After 3 h a second portion of initiator (30 mg, 0.12 mmol) was added. After a further 3 h the reaction solution was cooled and filtered. The filtrate was washed with sat. NaHCO$_3$ (aq.), dried (MgSO$_4$), filtered and the solvent removed. The residue was partially purified by flash chromatography (EtOAc:hexane, 1:50) to afford crude 3,5-di(tert-butoxycarbo)benzylbromide (3) (0.872 g, 96%). A solution of 3 (0.872 g, 2.35 mmol) and NaSSO$_2$CH$_3$ (0.327 g, 2.44 mmol) in DMF (1 mL) was heated at 50° C. under N$_2$. After 1 h the reaction solution was cooled, diluted with water (5 mL) and extracted with ether (15 mL×3). The combined extracts were washed with brine, dried (MgSO$_4$) and the solvent removed. The residue was purified by flash chromatography (EtOAc:hexane, 1:8) to give 3,5-di(tert-butoxycarbo)benzyl methanethiosulfonate (4) (0.570 g, 60%) as a colorless oil; IR (film) 1717 $cm^{-1}$ (C=O), 1604, 1477, 1456 $cm^{-1}$ (Ar C=C), 1328, 1135 $cm^{-1}$ (S—SO$_2$); $^1$H NMR (CDCl$_3$) δ1.59 (s, 18H, C(CH$_3$)$_3$), 3.07 (s, 3H, SO$_2$CH$_3$), 4.43 (s, 2H, CH$_2$), 8.13 (s, 2H, H-2, H-6), 8.48 (s, 1H, H-4); $^{13}$C NMR (CDCl$_3$) δ28.2 (C(CH$_3$)$_3$), 40.0 (CH$_2$), 51.3 (SO$_2$CH$_3$), 82.1 (C(CH$_3$)$_3$), 130.2, 133.2, 133.5, 135.7 (Ar), 164.3 (COO).

A solution of 4 (0.941 g, 2.30 mmol) in CF$_3$COOH:CH$_2$Cl$_2$ (1:1 v/v, 10 mL) was stirred at room temperature for 3 h, during which time a white precipitate was formed. The solvents were removed and the residue triturated with CH$_2$Cl$_2$ (5 mL). The resulting mixture was filtered, and the residue washed with CH$_2$Cl$_2$ and dried under vacuum to give 1c (0.611 g, 91% from 4) as a white solid; mp 199.5–200° C. (dec.); IR (KBr) 1716, 1693 $cm^{-1}$ (C=O), 1605, 1461 $cm^{-1}$ (Ar C=C), 1319, 1128 $cm^{-1}$ (S—SO$_2$); $^1$H NMR (acetone-d$_6$) δ3.29 (s, 3H, SO$_2$CH$_3$), 4.69 (s, 2H, CH$_2$), 8.36 (d,J 1.4 Hz, 2H, H-2, H-6), 8.61 (t,J 1.7 Hz, 1H, H-4); $^{13}$C NMR (acetone-d$_6$) δ40.0 (CH$_2$), 51.2 (SO$_2$CH$_3$), 130.8, 132.5, 135.2, 138.5 (Ar), 166.3 (COOH); MS m/z (EI+): 290 (M$^+$, 2), 273 (M$^+$—OH, 4), 210 (M$^+$—CH$_3$SO$_2$H, 100), 179 (M$^+$—SSO$_2$CH$_3$, 5); HRMS m/z (FAB+): Found 290.9987 (M+H$^+$), C$_{10}$H$_{11}$O$_6$S$_2$ requires 290.9998.

3,3-Dicarboxybutyl Methanethiosulfonate (1d)

Anhydrous K$_2$CO$_3$ (1.67 g, 12.0 mmol) was added to a solution of methyl Meldrum's acid (5b) (1 g, 6.33 mmol) in DMF (33 mL) under N$_2$ and stirred vigorously. After 1 h the supernatant liquid was added dropwise to a solution of 1,2-dibromoethane (1.9 mL, 22.2 mmol) in DMF (11 mL) under N$_2$. After 89 h TLC (EtOAc:hexane, 1:3) indicated conversion of starting material (R$_f$0.3) to a major product (R$_f$0.5). The reaction mixture was added to water (100 mL) and extracted with ether (100 mL×3). The organic fractions were combined, dried (MgSO$_4$), filtered and the solvent removed. The residue was purified by flash chromatography (EtOAc:hexane, 1:4) to give 5-(2'-bromoethyl)-2,2,5-trimethyl-1,3-dioxocyclohexa-4,6-dione (6b) (1.183 g, 71%) as a white solid; mp 84–85° C. (ether/hexane); IR (KBr) 1738, 1784 $cm^{-1}$ (C=O); $^1$H NMR (CDCl$_3$) δ1.66 (s, 3H, CH$_3$), 1.76, 1.78 (s×2, 3H×2, C(CH$_3$)$_2$), 2.61 (t,J 8 Hz, 2H, H-1), 3.32 (t,J 8 Hz, 2H, H-2'); $^{13}$C NMR (CDCl$_3$) δ25.2, 26.6, 29.1, 30.1, 42.4 (CH$_3$, C(CH$_3$)$_2$, C-1', C-2'), 49.4 (C-5), 106.0 OC(CH$_3$)$_2$), 169.5 (C-4, C-6); MS m/z (EI+): 249, 251 (M$^+$-CH$_3$, 5), 206, 208 (M$^+$—OC(CH$_3$)$_2$, 14), 162, 164 (M$^+$—C(O)OCO(CH$_3$)$_2$, 42), 69 (M$^+$—C(O)OCO(CH$_3$)$_2$—CH$_2$Br, 100%).

NaSSO$_2$CH$_3$ (776 mg, 5.80 mmol) was added to a solution of 6b (1.18 g, 4.46 mmol) in DMF (40 mL) under N$_2$ and the resulting solution warmed to 50° C. After 29 h the reaction solution was cooled and the solvent removed. The residue was purified by flash chromatography (EtOAc:hexane, 3:7 to give 2-(2',2',5'-trimethyl-1,3-dioxocyclohexa-4,6-dionyl)ethyl methanethiosulfonate (7b) (1.10 g, 83%) as a cloudy oil; IR (film) 1737, 1771 $cm^{-1}$ (C=O), 1300, 1133 $cm^{-1}$ (S—SO$_2$); $^1$H NMR (CDCl$_3$) δ1.68 (s, 3H, CH$_3$), 1.78, 1.79 (s×2, 3H×2, C(CH$_3$)$_2$), 2.47–2.55 (m, 2H, H-2), 3.08–3.16 (m, 2H, H-1), 3.34 (s, 3H, SSO$_2$CH$_3$); $^{13}$C NMR (CDCl$_3$) δ24.9, 29.3, 30.0, 31.9, 49.2 (CH$_3$, C(CH$_3$)$_2$, C-1, C-2), 49.2 (C-5'), 51.2 (SSO$_2$CH$_3$), 106.1 (C(CH$_3$)$_2$), 169.5 (C-4', C-6'); MS m/z (EI+): 281 (M$^+$—CH$_3$, 1), 269 (2), 239 (M$^+$—C$_3$H$_5$O, 3), 159 (100), 141 (56), 113 (96), 103 (23), 87 (78), 69 (M$^+$—C(O)OCO(CH$_3$)$_2$—CH$_2$SSO$_2$CH$_3$, 79%).

Dowex 50W(H$^+$) resin (2.53 g) was added to a suspension of 7b (1.08 g, 3.65 mmol) in p-dioxan (3.5 mL) and distilled water (35 mL) and stirred at room temperature. After 68 h the reaction mixture was filtered and the solvent removed. The resulting solid was recrystallized from water/acetone/ethyl acetate to give 1d (738 mg, 79%) as a white solid; mp 109–111° C.; IR (KBr) 1706 $cm^{-1}$ (C=O), 1317, 1133 $cm^{-1}$ (S—SO$_2$); $^1$H NMR (D$_2$O), δ1.43 (s, 3H, H-4), 2.25–2.33 (m, 2H, H-2), 3.16–3.24 (m, 2H, H-1), 3.45 (s, 3H, SSO$_2$CH$_3$); $^{13}$C NMR (D$_2$O) δ20.3 (C-4), 32.1, 36.4 (C-1, C-2), 50.5 (SSO$_2$CH$_3$), 54.3 (C-3), 176.0 (COOH); MS m/z (EI+): 256 (M$^+$, 6), 132 (M+H$^+$—CH$_2$SSO$_2$CH$_3$, 40), 116 (59), 87 (100%); HRMS m/z (CI–): Found 254.9996 ([M–H]$^-$); C$_7$H$_{11}$O$_6$S$_2$ requires 254.9997.

3,3,4-Tricarboxvbutyl Methanethiosulfonate (1e)

Anhydrous K$_2$CO$_3$ (1.2 g, 8.68 mmol) was added to a solution of Meldrum's acid (5a) (1 g, 6.94 mmol) in DMF (20 mL) under N$_2$ and stirred vigorously. After 2 h the supernatant liquid was added dropwise over a period of 1 h 30 min to a solution of tert-butylbromoacetate (1.14 mL, 7.63 mmol) in DMF (5 mL) under N$_2$. After a further 52 h TLC (acetone:toluene, 1:9) indicated the conversion of starting material (R$_f$ 0.45) to major (R$_f$0.5) and minor (R$_f$0.8) products. The reaction mixture was added to water (100 mL) and extracted with ether (100 mL×3). The organic fractions were combined, dried (MgSO$_4$), filtered and the solvent removed. The residue was purified by flash chromatography (EtOAc:hexane, 3:17 to 1:3) to give 5,5-di(tert-butoxycarbo)methyl-2,2-dimethyl-1,3-dioxocyclohexa-4,6-dione (412 mg, 16%); mp 103–105° C. (ether/hexane); $^1$H NMR (CDCl$_3$) δ1.41 (s, 18H, C(CH$_3$)$_3$×2), 1.92 (s, 6H, C(CH$_3$)$_2$), 2.97 (s, 4H, CH$_2$COOBu$^t$×2); $^{13}$C NMR (CDCl$_3$) δ28.5 (C(CH$_3$)$_3$), 29.2, 44.1 (CH$_2$COOBu$^t$, C(CH$_3$)$_2$) 47.2 (C-5), 83.1 (C(CH$_3$)$_3$), 108.5 (C(CH$_3$)$_2$), 168.0, 168.9 (C-4, C-6, CCOOBu$^t$); and a mixture of 5a and 5-(tert-butoxycarbo)methyl-2,2-dimethyl-1,3-dioxocyclohexa-4,6-dione (5c). This mixture was purified by repeated crystallization from ether/hexane to give 5c (1.05 g, 59%) as a white solid; mp 124–126° C. (ether/hexane); IR (KBr) 1772, 1755, 1712 cm$^{-1}$ (C=O); $^1$H NMR (CDCl$_3$) δ1.43 (s, 9H, C(CH$_3$)$_3$), 1.80 (s, 6H, C(CH$_3$)$_2$), 3.09 (d,J 4 Hz, 2H, CH$_2$COOBu$^t$), 3.70 (t,J 4 Hz, 1H, H-5); $^{13}$C NMR (CDCl$_3$) δ18.7, 28.8, 33.0, 43.4 (CH$_2$COOBu$^t$, C(CH$_3$)$_2$, C-5), 28.5 (C(CH$_3$)$_3$), 82.8 (C(CH$_3$)$_3$), 105.6 (C(CH$_3$)$_2$), 165.6, 169.6 (C-4, C-6, COOBu$^t$); MS m/z (CI-): 257 ([M-H]$^-$, 100), 200 (8), 159 (25) 143 (32%).

Anhydrous K$_2$CO$_3$ (300 mg, 2.17 mmol) was added to a solution of 5c (400 mg, 1.55 mmol) in DMF (10 mL) under N$_2$ and stirred vigorously. After 1 h the supernatant liquid was added dropwise to a solution of 1,2-dibromoethane (0.7 mL, 8.06 mmol) in DMF (3 mL) under N$_2$ at 50° C. After 70 h, t.l.c. (EtOAc:hexane, 1:9) indicated the conversion of starting material (R$_f$0.1) to a major product (R$_f$0.3). The reaction mixture was cooled, added to distilled water (50 mL) and extracted with ether (50 mL×3). The organic fractions were combined, dried (MgSO$_4$), filtered and the solvent removed. The residue was purified by flash chromatography (EtOAc:hexane, 1:9) to give 5-(2'-bromoethyl)-5-(tert-butoxycarbo)methyl-2,2-dimethyl- 1,3-dioxocyclohexa-4,6-dione (6c) (372 mg, 66%) as a white solid; mp 120–123° C. (ether/hexane); IR (KBr) 1773, 1731 cm$^{-1}$ (C=O); $^1$H NMR (CDCl$_3$) δ1.40 (s, 9H, C(CH$_3$)$_3$), 1.80, 1.93 (s×2, 3H×2, C(CH$_3$)$_2$), 2. 41 (t,J 8 Hz, 2H, H-1'), 3.11 (s, 2H, CH$_2$COOBu$^t$), 3.32 (t,J 8 Hz, 2H, H-2'); $^{13}$C NMR (CDCl$_3$) δ25.2, 29.3, 29.9, 41.0, 41.4 (CH$_2$COOBu$^t$, C(CH$_3$)$_2$, C-1', C-2'), 28.5 (C(CH$_3$)$_3$), 51.2 (C-5), 83.2 (C(CH$_3$)$_3$), 107.8 (C(CH$_3$)$_2$), 167.8, 170.2 (C-4, C-6, COOBu$^t$); MS m/z (CI-): 287 (2), 257 (M$^-$—(CH$_2$)$_2$Br, 100), 142 (15) 79, 81 (Br$^-$, 91%).

NaSSO$_2$CH$_3$ (143 mg, 1.07 mmol) was added to a solution of 6c (301 mg, 0.82 mmol) in DMF (20 mL) under N$_2$ and the resulting solution warmed to 50° C. After 29 h the reaction solution was cooled and the solvent removed. The residue was purified by flash chromatography (EtOAc:hexane, 1:3) and crystallized from ether to give 2-(5'-(tert-butoxycarbo)methyl-2',2'-dimethyl- 1,3-dioxocyclohexa-4,6-dionyl)ethyl methanethiosulfonate (7c) (280 mg, 86%) as a colorless crystalline solid; mp 103–105° C. (ether/hexane); IR (KBr) 1772, 1738, 1717 cm$^{-1}$ (C=O) 1314, 1129 cm$^{-1}$ (S—SO$_2$); $^1$H NMR (CDCl$_3$) δ1.41 (s, 9H, C(CH$_3$)$_3$), 1.83, 1.93 (s×2, 3H×2, C(CH$_3$)$_2$), 2.33–2.41 (m, 2H, H-2), 3.10–3.18 (m, 2H, H-1), 3.13 (s, 2H, CH$_2$COOBu$^t$), 3.32 (s, 3H, SSO$_2$CH$_3$); $^{13}$C NMR (CDCl$_3$) δ28.0 (C(CH$_3$)$_3$), 28.9, 29.2, 30.7, 37.9, 40.2 (CH$_2$COOBu$^t$, C(CH$_3$)$_2$, C-1, C-2), 50.0 (C-5'), 50.6 (SSO$_2$CH$_3$), 82.8 ( C(CH$_3$)$_3$), 107.3 (C(CH$_3$)$_2$), 167.2, 169.7 (C-4', C-6', COOBu$^t$); MS m/z (CI-): 395 ([M-H]$^-$, 1), 381 (M$^-$—CH$_3$, 2), 281 (M$^-$—H—CH$_2$COOBu$^t$, 5), 257 (M$^-$-(CH$_2$)$_2$SSO$_2$CH$_3$, 100), 215 (45), 158 (37%).

A solution of 7c (138 mg, 0.35 mmol) in CF$_3$COOD:D$_2$O (7:3, 2 mL) was heated to 50° C. After 32 h, $^1$H NMR spectroscopy showed the conversion of starting material to a single product. The solution was cooled and the solvent removed. The residue was purified by flash chromatography (butan-1-ol:AcOH:water, 4:1:1) and ion exchange chromatography (Amberlyst A21, 30% v/v CF$_3$COOH (aq.) as eluent) to give 1e (73 mg, 70%) as an amorphous solid; IR (KBr) 1706 cm$^{-1}$ (C=O) 1310, 1127 cm$^{-1}$ (S—SO$_2$); $^1$H NMR (D$_2$O) δ2.25–2.34 (m, 2H, H-2), 3.01 (s, 2H, H-4), 3.12–3.20 (m, 2H, H-1), 3.45 (s, 3H, SSO$_2$CH$_3$); $^{13}$C NMR (D$_2$O) δ34.3, 37.7, 41.1 (C-1, C-2, C-4), 52.9 (SSO$_2$CH$_3$), 58.0 (C-3), 177.0, 177.1 (COOH, CH$_2$COOH); MS m/z (FAB-): 299 ([M-H]$^-$, 42), 221 (21), 183 (40), 111 (49), 91 (100%). Anal. calcd. for C$_8$H$_{12}$O$_8$S$_2$: C, 32.00; H, 4.03%; found: C, 31.84; H 3.91%;

Site-specific Chemical Modification

To approximately 25 mg of each of the SBL mutants in CHES buffer (2.5 mL; 70 mM CHES, 5 mM MES, 2 mM CaCl$_2$, pH 9.5) at 20° C. was added each of the methanethiosulfonate reagents (100 μL of a 0.2 M solution: 1b in CH$_3$CN:H$_2$O (1:9), 1a,c,d,e in water), in a PEG(MW 10,000)-coated polypropylene test tube and mixed using an end-over-end rotator. The progress of modification was followed using specific activity measurement, monitored spectrophotometrically (10 μL aliquots in 0.1 M Tris-HCl buffer, pH 8.6, 0.005 % Tween 80, and 1% DMSO, with succinyl-AAPF-pNA (1 mg/mL) as substrate at 25° C., $\epsilon_{410}$=8800 M$^{-1}$ cm$^{-1}$) (Bonneau et al. (1991) J. Am. Chem. Soc. 119: 1026–1030) on a Perkin-Elmer Lambda 2 spectrophotometer. The reaction was terminated when the addition of a further 100 μL of methanethiosulfonate solution gave no further change in specific activity, typically after 2 to 3 h. The reaction solution was purified on a disposable desalting column (Pharmacia Biotech PD-10, Sephadex G-25 M) pre-equilibrated with MES buffer (5 mM MES, 2 mM CaCl$_2$, pH 6.5). The CMM was eluted with this buffer (3.5 mL), dialyzed against MES buffer (10 mM MES, 1 mM CaCl$_2$ pH 5.8, 1 L×3) at 4° C. and subsequently flash frozen and stored at −18° C. The free thiol content of all CMMs, was determined spectrophotometrically by titration with Ellman's reagent (Ellman et al. (1961) Biochem. Pharmacol. 7: 88–95) ($\epsilon_{412}$=13600 M$^{-1}$ cm$^{-1}$) in phosphate buffer 0.25 M, pH 8.0. In all cases no free thiol was detected. Modified enzymes were analyzed by nondenaturing gradient (8–25%) gels at pH 4.2, run towards the cathode, on the Pharmacia Phast-system and appeared as a single band. Each of the CMMs showed reduced mobility relative to wild-type. Prior to ES-MS analysis CMMs were purified by FPLC (BioRad, Biologic System) on a Source 15 RPC matrix (17-0727-20 from Pharmacia) with 5% acetonitrile, 0.01% TFA as the running buffer and eluted with 80% acetonitrile, 0.01% TFA in a one step gradient. MS m/z (ES–MS): N62C-a (Berglund et al. (1997) J. Am. Chem. Soc. 119: 5265–5266) calculated 26826, found 26828; S156C-a (DeSantis et al. (1998) Biochem. 37: 5968–5973) calculated 26853, found 26859; S166C-a (Id.) calculated 26853, found 26851; L217C-a (Berglund et al (1997) J. Am. Chem. Soc. 119: 5265–5266) calculated 26827, found 26828; N62C-b calculated 26819, found 26820; SI56C-b calculated 26846, found 26846; S166C-b calculated 26846, found 26846; L217C-b calculated 26820, found 26820; N62C-c calculated 26897, found 26896; S156C-c calculated 26924, found 26928; S166C-c calculated 26924, found 26928; L217C-c calculated 26898, found 26904; N62C-d calculated 26863, found 26870; S156C-d calculated 26890, found 26892; S166C-d calculated 26890, found 26894; L217C-d calculated 26864, found 26866; N62C-e calculated 26907, found 26909; S156C-e calculated 26934, found 26939; S166C-e calculated 26934, found 26939; L217C-e calculated 26908, found 26911.

Active Site Titrations

The active enzyme concentration was determined as previously described (Hsia et al. (1996) J. Anal. Biochem. 242: 221–227) by monitoring fluoride ion release upon enzyme reaction with -toluenesulfonyl fluoride (PMSF) as measured by a fluoride ion sensitive electrode (Orion Research 96-09). The active enzyme concentration determined in this way was used to calculate $k_{cat}$ values for each CMM except in the case of S166C-e for which total protein concentration as detemined by absorbance at 280 nm ($\epsilon_{280}$=23000 M$^{-1}$ cm$^{-1}$) (Grøn et al. (1990) *Eur. J. Biochem.* 194:897–901) was used.

Kinetic Measurements

Michaelis-Menten constans were measured at 25(±0.2)° C. by curve fitting (GraFit® 3.03) of the initial rate data determined at eight or nine concentrations (0.125 mM–4.0 mM) of succinyl-AAPF-pNA substrate in 0.1 M Tris-HCl buffer containing 0.005% Tween 80, 1% DMSO, pH 8.6 ($_{410}$=8800 M$^{-1}$ cm$^{-1}$) (Bonneau et al. (1991) *J. Am. Chem. Soc.* 119: 1026–1030).

Example 2

Altering the Specificity of Subtilisin *Bacillus lentus* through the Introduction of Positive Charge at Single Amino Acid Sites The use of methanethiosulfonates as thiol-specific modifying reagents in the strategy of combined site-directed mutagenesis and chemical modification allows virtually unlimited opportunities for creating new protein surface environments. As a consequence of our interest in electrostatic manipulation as a means of tailoring enzyme activity and specificity, we have adopted this approach for the controlled incorporation of multiple negative charges at single sites in the representative serine protease, subtilisin *Bacillus lentus* (SBL). We now describe the use of this strategy to introduce multiple positive charges. A series of mono-, di- and triammonium methanethiosulonates were synthesized and used to modify cysteine mutants of SBL at positions 62 in the S$_2$ site, 156 and 166 in the S$_1$ site and 217 in the S$_1$' site. Kinetic parameters for these chemically modified mutants (CMM) enzymes were determined at pH 8.6. The presence of up to three positive charges into the S$_1$, S$_1$' and S$_2$ subsites of SBL resulted in up to 77-fold lowered activity, possibly due to interference with the histidinium ion formed in the transition state of the hydrolytic reactions catalyzed.

Results And Discussion

Synthesis of Alkylammonium Methanethiosulfonates 1b-d

Previous work (Berglund et al. (1997) *J. Am. Chem. Soc.* 119: 5265–5266; Kenyon and Bruice (1977) *Methods Enzymol.* 47: 407–430) has demonstrated that, of the methods available (Douglass and Farah (1959) *J. Org. Chem.* 24: 973–975; Levitt and Levitt (1972) *J. Org. Chem.* 37: 332–334; Weidner and Block (1972) *J. Med. Chem.* 15: 564–567; Palumbo and Caputo (1981) *Synthesis* 888–890; Block and Zhao (1992) *J. Org. Chem.* 57: 5815–5817; Billard et al. (1996) *J. Org. Chem.* 61: 7545–7550), direct nucleophilic displacement of a primary alkyl bromide by methanethiosulfonate ion provides the most efficient method for the preparation of alkyl methanethiosulfonates. This general method was therefore adopted as the basis for the preparation of all of 1b–d. The singly-charged trimethylammonium MTS 1b (Ginsberg (1962) *J. Med. Pharm. Chem.* 5: 1364–1367.) was prepared from 2-bromoethyltrimethylammonium bromide and NaSSO$_2$CH$_3$ in 57% yield.

Figure 6:
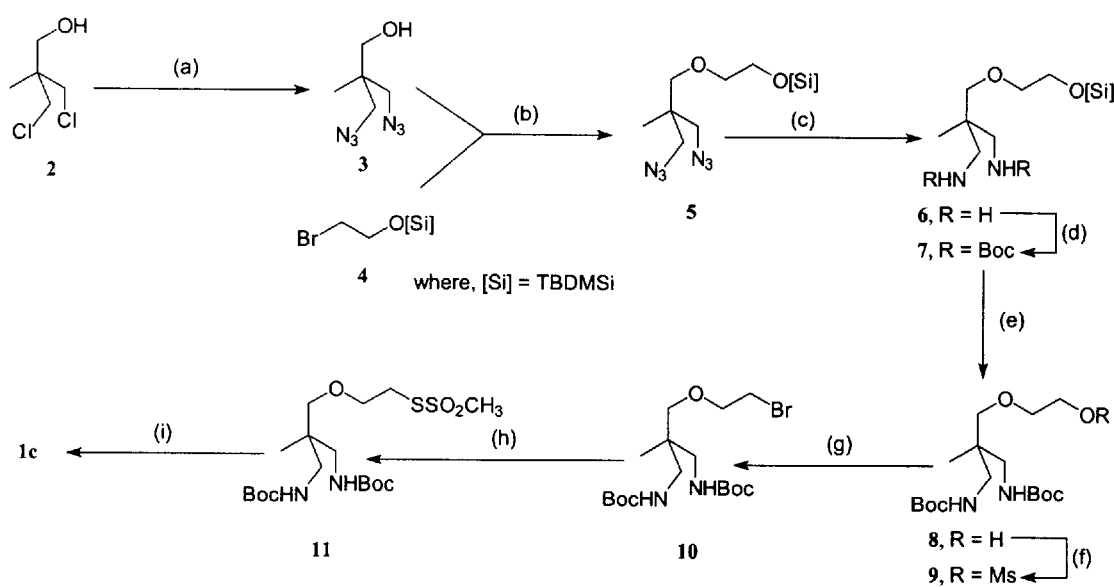
FIG. 6 shows scheme 3 for the synthesis of the doubly-charged MTS reagent 1c from the readily available dichloroalcohol 1 (. (a) $NaN_3$, 130° C., 98% (b) NaH, $Bu_4NI$, THF then 4, 55% (c) $H_2$, Pd-black, MeOH (d) $Boc_2O$, NaOH (aq.)/dioxan, 72% over 2 steps (e) TBAF, THF, 93% (f) MsCl, $Et_3N$, $CH_2Cl_2$, 99% (g) LiBr, acetone, Δ, 93% (h) $NaSSO_2CH_3$, DMF, 50° C., 87% (i) $CF_3COOH$, $CH_2Cl_2$, then ion exchange chromatography, 67%.

The doubly-charged MTS reagent 1c was synthesized from the readily available dichloroalcohol 1( ) (FIG. 6 showing scheme 3). Initial attempts at constructing an untethered dipositive MTS failed as consequence of the hindered nature of the neopentyl-like system and therefore the less-hindered tethered system 1c was adopted as a target. (Although untethered 2,2-bis(aminomethyl)-1-bromo-N,N'-di-tert-butoxycarbonyl-propane was successfully prepared, all attempts at introducing methanethiosulfonate ion under a range of conditions failed).

Nitrogen was introduced through the treatment of a solution of 1 with an excess of NaN$_3$ at 130° C. to give diazide 2 ( ), which was formed in a high degree of purity and used without further purification. Br(CH$_2$)$_2$OH protected as its tert-butyldimethylsilyl (TBDMS) ether 3 ( ) (Branchaud (1983) *J. Org. Chem.* 48 :3531–3538; Vader et al. (1989) *Tetrahedron.* 45: 2131–2142) was used to introduce an ethyl tether to 2. NaH was used to deprotonate the free alcohol in 2 and the resulting alkoxide anion was alkylated with 3 to give tethered diazide 4 in 55% yield.

Diazide 4 ( ) was hydrogenated in the presence of Pd-black in MeOH and the free amine groups thus formed were protected by treatment of diamine 5 ( ) with Boc$_2$O to give dicarbamate 6 ( ) (72% yield over 2 steps from 4). With the amine groups now suitably protected the silyl ether moiety of 6 was selectively deprotected using TBAF to give alcohol 7 ( ) in 93% yield. Treatment of 7 with MsCl and then LiBr allowed the formation of the primary bromide 9 ( ) via the corresponding mesylate 8 ( ) in 93% yield. The primary bromide group in 9 was displaced with methanethiosulfonate to give protected diammonium MTS 10 ( ) in 87% yield. Gratifyingly, deprotection of the Boc groups in 10 using TFA in DCM allowed the successful preparation of target dipositive MTS reagent 1c in 67% yield (35% overall yield from dichloroalcohol.

Figure 7:
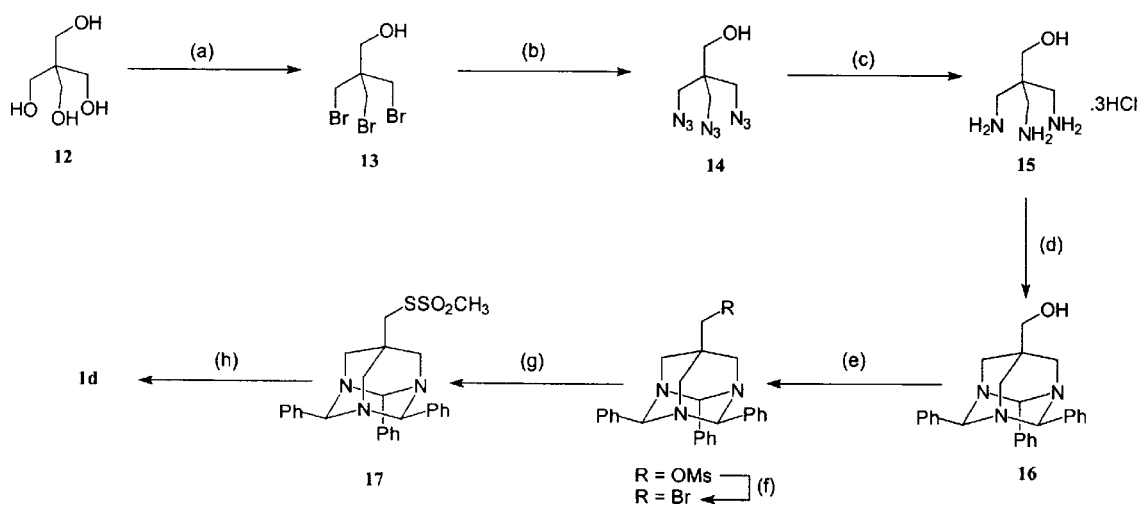
FIG. 7 show scheme 4 for the synthesis of triply-charged MTS 1d from pentaerythritol (a) HBr, AcOH, Δ then HBr, c. $H_2SO_4$, Δ, 49% (b) $NaN_3$, DMF, 100° C. (c) (i) $PPh_3$, $NH_3$(aq)/dioxan (ii) HCl (aq), 57% over 3 steps (d) PhCHO, $Et_3N$, MeOH, 99% (e) MsCl, $Et_3N$, $CH_2Cl_2$, 77% (f) LiBr, acetone, Δ, 78% (g) $NaSSO_2CH_3$, DMF, 80° C., 65% (d) HCl (aq), 69%.
Figure 8A:
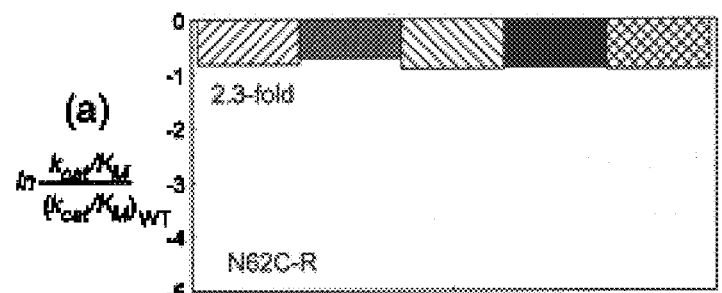
FIGS. 8A, 8B, 8C and 8D show altered specificity patterns for N62C (FIG. 8A), L271C (FIG. 8B), S156C (FIG. 8C), and S166C (FIG. 8D) CMMs: variations in ln ($k_{cat}/K_M$), with suc-AAPF-pNA as the substrate, for cysteine mutants and positively charged CMMs relative to WT. R group key: a=2-aminoethyl; b=2-(trimethylammonium)ethyl; c=5,5-bis (aminomethyl)-3-oxo-hexyl; d=2,2-bis(aminomethyl)-3-aminopropyl.
Figure 8B:
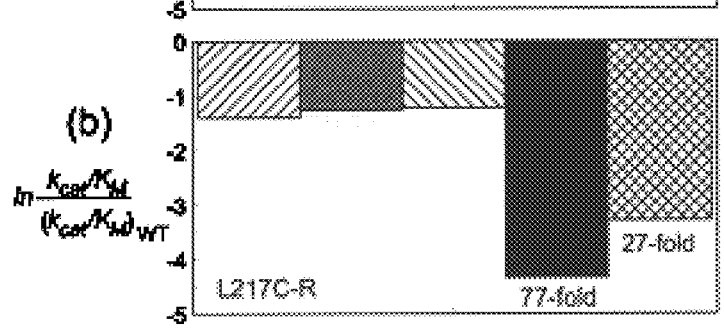
Figure 8C:
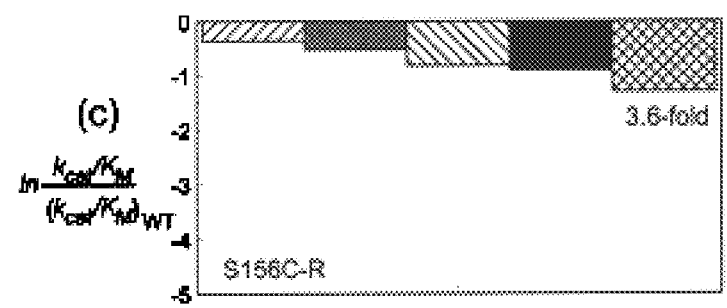
Figure 8D:
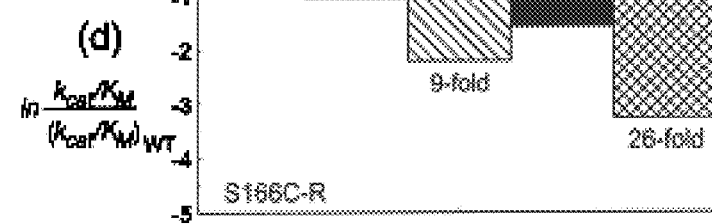

For the synthesis of triply-charged MTS 1d (scheme 4 shown in FIG. 7), pentaerythritol 11 was chosen as a cheap and readily available starting material. In order to introduce three amine groups and one methanethiosulfonate it was necessary to differentiate three of the four alcohol groups found in 11. This was readily achieved through the treatment of 11 with concentrated HBr in the presence of refluxing strong acid (Overburger et al. (1975) *Macromolecules.* 8: 31–36), conditions which allowed the formation of tribromide 12 (D'yachenko and Lukima, (1966) *Izv. Acad. Nauk. SSSR:*2237) in 49% yield.

As for the synthesis of 1c, NaN$_3$ was used to introduce the required amine groups in masked form. Compounds containing high levels of nitrogen, such as triazide 12 ( ) present potential explosion hazards (Dunn et al. (1990) *J. Org. Chem.*55: 6368–6373) and therefore preparations avoided isolation through immediate reduction of a solution of 13 using the Staudinger reaction (Staudinger and Meyer (1919) *Helv. Chim. Acta.* 2: 635–646; Martin et al. (1995) *Org. Prep. Proc. Intl.* 27: 117–120). The iminophosphorane product was hydrolyzed upon acidic work-up to the corresponding triaminoalcohol which was isolated and purified through crystallization as its trihydrochloride salt 14 ( ) (Litherland and Mann (1938) *J. Chem. Soc.* 1588).

Functionalization of the remaining alcohol group in 14 required protection of the three introduced amino groups. This was achieved through the condensation of 14 with PhCHO in the presence of Et$_3$N which allowed the rapid formation of the triazadamantane 15 ( ) (Dunn et al. (1990) *J. Org. Chem.*55: 6368–6373) in an excellent 99% yield. The free alcohol group in 15 was converted to a methanethiosulfonate group in an analogous manner to that used for the synthesis of 1c. Therefore, base-catalyzed mesylation of 15 and subsequent treatment with LiBr and then NaSSO$_2$CH$_3$ gave protected triamino MTS 16 ( ) in 39% yield over 3 steps. Treatment of an ethereal solution of 16 with dilute HCl allowed cleavage of the triaazaadamantane protecting group and crystallization of the target triammonium MTS reagent as its trihydrochloride salt 1d (69% yield, 7% overall yield from 11).

Preparation of Chemically Modified Mutants (CMMs)

MTS reagents 1a–d were used to modify the chosen SBL cysteine mutants, N62C, S156C, S166C and L217C under conditions described previously (Berglund et al. (1997) *J. Am. Chem. Soc.* 119: 5265–5266; Stabile et al. (1996) *Bioorg. Med. Chem. Lett.*6: 2501–2512; DeSantis et al. (1998) *Biochem.* 37: 5968–5973). These reactions proceeded rapidly and quantitatively, as judged by the monitoring of changes in specific activity and by titration of free thiols with Ellman's reagent (Ellman et al. (1961) *Biochem. Pharmacol.* 7: 88–95), respectively. The structure of the charged CMMs was confirmed by ES-MS. Non-reducing native PAGE was used to determine the purity of all the enzymes, which appeared as single bands. Consistent with the introduction of positive charge, each of the CMMs showed increased mobility in the direction of the cathode relative to WT. The active enzyme concentration of the resulting CMM solutions was determined by active site titration with α-toluenesulfonyl fluoride (PMSF) using a fluoride ion-sensitive electrode (Hsia et al. (1996) *Anal. Biochem.* 242: 221–227).

Kinetic Effects of Site Specific Modification

The effects of modification upon SBL were assessed by the determination of $k_{cat}$ and $K_M$ for the hydrolysis of succinyl-AAPF-p-nitroanilide (Suc-AAPF-pNA) at pH of 8.6. The kinetic parameters of the 16 CMMs generated are compared with those of WT and unmodified mutants in Table 2 and FIG. 8.

here and $k_{cat}/K_M$s for N62C-a–d are near-identical to that of N62C. The underlying $k_{cat}$s and $K_M$s of N62C-a–d are also near-identical to each other, although 2-fold lower than N62C. The lowered $k_{cat}$s of N62C-a–d indicate that introduced positive charges destabilize the transition state of catalysis although this destabilization does not increase further with increasing charge.

At position 217, in the $S_1'$ pocket, mutation to cysteine causes a 4-fold decrease in $k_{cat}/K_M$ and demonstrates that mutation at this site is intrinsically more dramatic. Subsequent modification with singly positively charged MTS reagents 1a,b alters $k_{cat}/K_M$ little and the $k_{cat}/K_M$s of L217C-a,b are only 1.2-fold greater than L217C. In stark contrast, the introduction of two and three positive charges dramatically decreases $k_{cat}/K_M$. In fact, the $k_{cat}/K_M$s of L217C-c,d are 77- and 27-fold lower than WT, respectively. These decreases are the result of both decreased $k_{cat}$s that are up to 26-fold lower than WT for L217-c and increased $K_M$s that are up to 4-fold greater than WT for L217C-d.

At position 156, in the $S_1$ pocket, mutation to cysteine decreases $k_{cat}/K_M$ 1.4-fold. From S156C to S156C-a to S156C-d $k_{cat}/K_M$ decreases monotonically to 3.6-fold lower than WT as the level of positive charge increases. This gradual tailoring of the specificity of SBL away from hydrophobic substrate Suc-AAPF-pNA even at surface-exposed position 156 is consistent with a parallel trend for multiply negatively charged CMMs seen in Example 1.

At position 166, in the $S_1$ pocket, mutation of the internally-oriented side chain to cysteine decreases $k_{cat}/K_M$ 3-fold. Subsequent modification with singly positively charged MTS reagents 1a,b decreases $k_{cat}/K_M$ further. In

TABLE 2

Kinetic Parameters[a] for Modified Enzymes

| Entry | Enzyme | Pocket | R[b] | Level of Charge | $k_{cat}$ (s$^{-1}$) | $K_M$ (mM) | $k_{cat}/K_M$ (S$^{-1}$ mM$^{-1}$) |
|---|---|---|---|---|---|---|---|
| 1 | SBL-WT | — | — | — | 153 ± 4 | 0.73 ± 0.05 | 209 ± 15 |
| 2 | N62C | $S_2$ | H | 0 | 174 ± 9 | 1.90 ± 0.20 | 92 ± 11 |
| 3 | | | a | 1 | 103 ± 5 | 1.00 ± 0.10 | 103 ± 11 |
| 4 | | | b | 1 | 73 ± 2 | 0.86 ± 0.05 | 85 ± 5 |
| 5 | | | c | 2 | 92 ± 3 | 1.06 ± 0.07 | 87 ± 6 |
| 6 | | | d | 3 | 98 ± 3 | 1.17 ± 0.08 | 84 ± 6 |
| 7 | L217C | $S_1'$ | H | 0 | 41 ± 1 | 0.80 ± 0.04 | 51 ± 3 |
| 8 | | | a | 1 | 38 ± 1 | 0.64 ± 0.06 | 59 ± 6 |
| 9 | | | b | 1 | 43 ± 1 | 0.69 ± 0.03 | 62 ± 3 |
| 10 | | | c | 2 | 8.0 ± 0.2 | 2.94 ± 0.28 | 2.7 ± 0.3 |
| 11 | | | d | 3 | 23 ± 3 | 2.90 ± 0.16 | 7.8 ± 1.2 |
| 12 | S156C | $S_1$ | H | 0 | 125 ± 4 | 0.85 ± 0.06 | 147 ± 11 |
| 13 | | | a | 1 | 90 ± 2 | 0.73 ± 0.04 | 123 ± 7 |
| 14 | | | b | 1 | 68 ± 2 | 0.74 ± 0.04 | 92 ± 5 |
| 15 | | | c | 2 | 64 ± 1 | 0.76 ± 0.04 | 85 ± 5 |
| 16 | | | d | 3 | 46 ± 1 | 0.81 ± 0.05 | 57 ± 4 |
| 17 | S166C | | H | 0 | 42 ± 1 | 0.50 ± 0.05 | 84 ± 9 |
| 18 | | | a | 1 | 50 ± 1 | 0.68 ± 0.04 | 74 ± 5 |
| 19 | | | b | 1 | 33 ± 2 | 1.42 ± 0.13 | 23 ± 2 |
| 20 | | | c | 2 | 55 ± 2 | 1.27 ± 0.10 | 43 ± 4 |
| 21 | | | d | 3 | 9.3 ± 0.2 | 1.16 ± 0.05 | 8.0 ± 0.4 |

[a]Michaelis-Menten constants were measured at 25° C. according to the initial rates method in 0.1 M Tris-HCl buffer at pH 8.6, 0.005% Tween 80, 1% DMSO, Suc-AAPF-pNA as the substrate.
[b]a = 2-aminoethyl;
b = 2-(trimethylammonium)ethyl;
c = 5,5-bis(aminomethyl)-3-oxo-hexyl;
d = 2,2-bis(aminomethyl)-3-aminopropyl.

At position 62, in the $S_2$ pocket, mutation to cysteine reduces $k_{cat}/K_M$ by 2-fold. The tolerance of the $S_2$ pocket for multiple charge at a single site that was previously observed for negatively charged CMMs (Example 1), is also observed spite of the identical level of positive charge introduced the $k_{cat}/K_M$ of S166C-b is a dramatic 3-fold lower than that of S166C-a and 9-fold lower than WT. This difference is largely a result of decreased substrate binding and the $K_M$ of S166C-(CH$_2$)$_2$NMe$_3^+$ (-b) is 2-fold greater than that of S166C—S(CH$_2$)$_2$NH$_3^+$ (-a). This may be attributed to the added steric bulk of peralkylated side chain —S(CH$_2$)$_2$NMe$_3^+$ (-b) as compared with the unalkylated side chain —S(CH$_2$)$_2$NH$_3^+$ (-a). Modification with doubly positively charged MTS reagent 1c partially restores k$_{cat}$/K$_M$ to only 4-fold lower than WT. This exception to the general decreases in activity with increased positive charge may be a consequence of the added flexibility of tethered side chain c. This may allow the orientation of this side chain out of the S$_1$ pocket and towards external solvent in a manner analogous to that suggested by molecular modeling analysis for other charged CMMs. In contrast, the k$_{cat}$/K$_M$ of S166C-d, which bears a triply positively charged side chain, is severely lowered to 26-fold lower than WT. In contrast to the trend observed at position 217, the general decreases in k$_{cat}$/K$_M$s at position 166 are largely due to decreases in k$_{cat}$ alone. In fact, from S166C-b to -d the K$_M$ decreases monotonically to only 1.6-fold greater than WT.

Conclusions

In summary, we have devised short and efficient synthetic routes to two novel multiply charged methanethiosulfonates, 1c and d. Such compounds, as well as being of interest in our approach to the controlled tailoring of enzyme activity, may prove useful in the study of ion channels. The use of MTS reagents in techniques such as the substituted-cysteine accessibility method (SCAM) (Akabas et al. (1992) *Science* 258: 307–310; Akabas et al. (1994) *Neuron* 13: 919–927; Akabas et al. (1994) *J. Biol. Chem.* 269: 14865–14868) has allowed aspects of membrane ion channel topology and conformation to be determined. In particular the use of charged MTS reagents has given an invaluable insight into ion specificity (Cheung and Akabas (1997) *J Gen. Physiol.* 109: 289–299) and mechanism of action (Stauffer and Karlin (1994) *Biochem.* 33: 6840–6849; Yang et al. (1996) *Neuron* 16: 113–122; Holmgren et al. (1996) i *Neuropharmacol.* 35: 797–804; Huynh et al. (1997) *J. Gen. Physiol.* 110: 229–242; Rassendren et al. (1997) *EMBO J.* 16: 3446–3454).

Using our established methodology, we were able to fully modify the cysteine thiols of SBL mutants, N62C, S156C, S166C, and L217C, with these reagents. Without exception, mutation and modification at all four sites led to reduced catalytic efficiency in the hydrolysis of Suc-AAPF-pNA.

Experimental

Mutants of Subtilisin *Bacillus lentus* (SBL) were generated, and WT and mutant enzymes purified as described previously (Stabile et al. (1996) *Bioorg. Med. Chem. Lett.*6: 2501–2512; DeSantis et al. (1998) *Biochem.* 37: 5968–5973). NaSSO$_2$CH$_3$(Kenyon and Bruice (1977) *Methods Enzymol.* 47: 407–430) (mp 269–269.5° C. (dec.) [lit. (Id.), m.p. 272–273.5° C.]) and toluene-3,5-dicarboxylic acid (2) (Fittig et al. (1868) *Anal. Chem.* 147: 292–312) (mp 294.5–296° C. (water) [lit. (Id), m.p. 287–288° C.]) were prepared according to literature methods. DMF was distilled under N$_2$ from CaH$_2$ and stored over molecular sieve under N$_2$ before use. 2-aminoethyl methanethiosulfonate hydrobromide (1a) was purchased from Toronto Research Chemicals (2 Brisbane Rd., Toronto, ON, Canada). All other chemicals were used as received from Sigma-Aldrich or Baker. All flash chromatography was performed using silica gel (Whatman, 60 Å, 230–400 Mesh). Melting points were determined using an Electrothermal IA9000 series digital melting point apparatus and are uncorrected. IR spectra were recorded on Bomem MB or Perkin-Elmer FTIR Spectrum 1000 spectrophotometers. $^1$H NMR and $^{13}$C NMR spectra were recorded on a Varian Gemini 200 or Unity 400 NMR spectrometers at the frequencies indicated. ES-MS data were acquired using a PE SCIEX API III Biomolecular mass spectrometer. All other MS and HRMS data, were acquired using Micromass 70-250S or Micromass ZAB-SE mass spectrometers according to the ionization methods indicated. Solvents were removed in vacuo.

4.1 2-(Trimethylammonium)ethyl methanethiosulfonate bromide (1b)

A solution of 2-bromoethyltrimethylammonium bromide (1.25 g, 5.06 mmol) and NaSSO$_2$CH$_3$ (0.75 g, 5.60 mmol) in MeOH (10 mL) was heated under N$_2$ under reflux. After 50 h the resulting solution was cooled to −1820 C. The white solid formed was filtered from the mixture and recrystallized from EtOH to give 1b (796 mg, 57%) a white crystalline solid; mp 157.5–158.5° C. (EtOH) [lit.(Ginsberg(1962) *Med. Pharm. Chem.* 5: 1364–1367), 160° C. (EtOH)]; $^1$H NMR (D$_2$O, 200 MHz) δ3.14 (s, 9H, N(CH$_3$)$_3$), 3.54 (s,3H, CH$_3$SO$_2$), 3.57–3.64 (m, 2H, H-1), 3.67–3.77 (m, 2H, H-2).

4.2 5,5-Bis(aminomethyl)-3-oxo-hexyl methanethiosulfonate dihydrochloride (1c)

NaN$_3$ (10.78 g, 166 mol) was added to a solution of 2,2-bis(chloromethyl)-propan-1-ol (2) (1.98 g, 12.6 mmol) in DMF (88 mL) under N$_2$ and the resulting suspension warmed to 130° C. After 6 h the solution was cooled, poured into water (600 mL) and extracted with ether (100 mL then 5×50 mL). The organic fractions were combined, dried (MgSO$_4$), filtered and the solvent removed to give 2,2-bis (azidomethyl)-propan-1-ol (3) (2.10 g, 98%) as a yellow oil; IR (film) 3380 (O—H), 2102 (N$_3$) cm$^{-1}$; $^1$H NMR (CDCl$_1$, 400 MHz) δ0.93 (s, 3H, H-3), 1.76 (br s, 1H, OH), 3.32 (s, 4H, —CH$_2$N—), 3.47 (s, 2H, H-1); $^{13}$C NMR (CDCl$_3$, 100 MHz) δ18.3 (C-3), 41.1 (C-2), 55.7 (—CH$_2$N—), 66.2 (C-1); HRMS m/z (FAB+): Found 171.0970 (M+H$^+$); C$_5$H$_{11}$N$_6$O requires 171.0994.

NaH (480 mg, 80% dispersion, 16 mmol) was added to a solution of 3 (2.10 g, 12.4 mmol) and Bu$_4$NI (228 mg, 0.62 mmol) in THF (50 mL) under N$_2$. After 20 min 2-bromo-1-O-tert-butyldimethylsilylethanol (4.6 g, 19.2 mmol) was added dropwise. After 22 h, the solvent was reduced and the residue partitioned between ether (150 mL) and water (40 mL). The aqueous layer was reextracted with ether (50 mL×2). The organic fractions were combined, washed with brine (40 mL), dried (MgSO$_4$), filtered and the solvent removed. The residue was purified by flash chromatography (EtOAc:hexane, 1:19) to give 5,5-bis(azidomethyl)-1-O-tert-butyldimethylsilyl-3-oxo-hexan-1-ol (5) (2.24 g, 55%) as a colorless oil; IR (film) 2100 (N$_3$) cm$^{-1}$; $^1$H NMR (CDCl$_3$, 400 MHz) δ0.05 (s, 6H, Si(CH$_3$)$_2$), 0.88 (s, 9H, SiC(CH$_3$)$_3$), 0.94 (s, 3H, H-6), 3.24 (d, 2H, J$_{H,H'}$ 11.9 Hz, —CHH'N—×2), 3.26 (s, 2H, H-4), 3.28 (d, 2H, J$_{H,H'}$ 12.1 Hz, —CHH'N—×2), 3.47–3.50 (m, 2H, H-2), 3.72–3.74 (m, 2H, H-1); $^{13}$C NMR (CDCl$_3$, 100 MHz) δ−5.3 (Si(CH$_3$)$_2$), 18.1 (SiC(CH$_3$)), 18.4 (C-6), 25.9 (C(CH$_3$)$_3$), 41.2 (C-5), 55.8 (—CH$_2$N—), 62.6, 73.0, 73.7 (C-1, C-2, C-4); MS m/z (FAB+): 351 (M+Na$^+$, 3), 329 (M+H$^+$, 45).

Pd-black (70 mg) was added to a solution of 5 (1 g, 3.05 mmol) in MeOH (27 mL) under N$_2$. The resulting suspension was thoroughly degassed and H$_2$ introduced. After 18 h the suspension was degassed, N$_2$ introduced, filtered through celite (MeOH as eluant) and the solvent removed to give crude 5,5-bis(aminomethyl)-1-O-tert-butyldimethylsilyl-3 -oxo-hexan-1-ol (6) (800 mg, 2. 90 mmol). This was dissolved in dioxan: 1M aq. NaOH (2:1, 20 mL) and the resulting solution cooled to 0° C. Boc$_2$O (1.4 g, 6.41 mmol) was added and after 30 min. the resulting mixture warmed to RT. After 3 h the reaction mixture was acidified to pH 4 with 1M KHSO$_4$ (aq.) and partitioned between EtOAc (300 mL) and water (100 mL). The aqueous layer was further extracted with EtOAc (200 mL). The organic fractions were combined, washed with sat. NaHCO$_3$ (aq., 100 niL), brine (100 mL), dried (MgSO$_4$), filtered and the solvent removed. The residue was purified by flash chromatography (EtOAc:hexane, 1:9 to 1:3) to give 5,5-bis (aminomethyl)-1-O-tert-butyldimethylsilyl-N,N'-di-tert-butoxycarbonyl-3-oxo-hexan-1-ol (7). (1.04 g, 72% over 2 steps) as a colorless oil; IR (film) 3360 (NH), 1701, (amide I), 1508 (amide II) cm$^{-1}$; $^1$H NMR (CDCl$_3$, 400 MHz) δ–0.02 (s, 6H, Si(CH$_3$)$_2$), 0.75 (s, 3H, H-6), 0.81 (s, 9H, SiC(CH$_3$)$_3$), 1.34 (s, 18H, OC(CH$_3$)$_3$×2), 2.83 (dd, 2H, J$_{H,NH}$ 5.3 Hz, J$_{H,H'}$ 14.0 Hz, —CHH'N—×2), 3.00 (dd, 2H, J$_{H',NH}$ 7.9 Hz, J$_{H,H'}$ 14.1 Hz, —CHH'N—×2), 3.16 (s, 2H, H-4), 3.39 (t, 2H, J4.9 Hz, H-2), 3.65 (t, 2H, J4.9Hz, H-1), 5.30 (br t, 2H, J6.8 Hz, NH×2); $^{13}$C NMR (CDCl$_3$, 100 MHz) δ–5.4 (Si(CH$_3$)$_2$), 18.2 (SiC(CH$_3$)), 18.8 (C-6), 25.7 (SiC(CH$_3$)$_3$), 28.3 (OC(CH$_3$)$_3$×2), 40.2 (C-5), 44.4 (—CH$_2$N—), 62.3, 72.8, 76.3 C-1, C-2, C4), 78.7 (O C(CH$_3$)$_3$×2), 156.7 (—NH(CO)O—×2); MS m/z (FAB+): 351 (M+Na$^+$, 3), 329 (M+H$^+$, 45).

A solution of TBAF in THF (1M, 3.7 mL, 3.7 mmol) was added dropwise to a solution of 7 (1.04 g, 2.18 mmol) in THF (17 mL) under N$_2$. After 3 h, the solvent was removed. The residue was dissolved in EtOAc (200 mL) and washed with water (100 mL×2). The aqueous layer was reextracted with EtOAc (100 mL x 2). The organic fractions were combined, dried (MgSO$_4$), filtered and the solvent removed. The residue was purified by flash chromatography (EtOAc:hexane, 1:1) to give 5,5-bis(aminomethyl)-N,N'-di-tert-butoxycarbonyl-3-oxo-hexan-1-ol (8) (735 mg, 93%) as a colorless oil; IR (film) 3355 (OH, NH), 1700 (amide I), 1520 (amide II) cm$^{-1}$; $^1$H NMR (CDCl$_3$, 400 MHz) δ0.80 (s, 3H, H-6), 1.39 (s, 18H, OC(CH$_3$)$_3$×2), 2.93 (dd, $^2$H, J$_{H,NH'}$ 5.6 Hz, J$_{H,H'}$ 14.0 Hz, —CHH'N—×2), 3.01 (dd, 2H, J$_{H',NH}$ 8.0 Hz, J$_{H,H'}$ 13.9 Hz, —CHH'N—×2), 3.14 (s, 2H, H-4), 3.29 (s, 1H, OH), 3.47 (t, 2H, J 4.5 Hz, H-2), 3.65 (t, 2H, J 4.3 Hz, H-1), 5.30 (br s, 2H, NH×2); $^{13}$C NMR (CDCl$_3$, 100 MHz) δ18.8 (C-6), 28.3 (OC(CH$_3$)$_3$×2), 40.3 (C-5), 44.0 (—CH$_2$N—), 61.3, 72.7, 74.7 (C-1, C-2, C-4), 79.2 (O C(CH$_3$)$_3$×2), 156.7 (—NH(CO)O—×2); MS m/z (FAB+): 385 (M+Na$^+$, 45), 363 (M+H$^+$, 95%).

MsCl (0.24 mL, 3.10 mmol) was added dropwise to a solution of 8 (735 mg, 2.03 mmol) and Et$_3$N (0.57 mL, 4.09 mmol) in DCM (5 mL) under N$_2$ at 0° C. After 1 h the solution was warmed to RT. After a further 16 h the solution was diluted with DCM (100 mL), washed with sat. NaHCO$_3$ (aq., 30 mL), water (30 mL), brine (30 mL), dried (MgSO$_4$), filtered and the solvent removed. The residue was purified by flash chromatography (MeOH:CHCl$_3$, 1:25) to give 5,5-bis(aminomethyl)-N,N'-di-tert-butoxycarbonyl-1-O-methanesulfonyl-3-oxo-hexan-1-ol (9) (880 mg, 99%) as a colorless oil; IR (film) 3360 (NH), 1700 (amide I), 1520 (amide II) 1362, 1173 (O—SO$_2$) cm$^{-1}$; $^1$H NMR (CDCl$_3$, 400 MHz) δ0.83 (s, 3H, H-6), 1.41 (s, 18H, OC(CH$_3$)$_3$×2), 2.94 (dd, 2H, J$_{H,NH}$ 5.9 Hz, J$_{H,H'}$ 14.2 Hz, —CHH'N—×2), 3.05 (s, 3H, CH$_3$SO$_2$), 3.06 (dd, 2H, J$_{H',NH}$ 7.7 Hz, J$_{H,H'}$ 13.9 Hz, —CHH'N—×2), 3.24 (s, 2H, H-4), 3.65–3.67 (m, 2H, H-2), 4.33–4.35 (m, 2H, H-1), 5.27 (br t, 2H, J 6.4 Hz, NH×2); $^{13}$C NMR (CDCl$_3$, 100 MHz) δ18.8 (C-6), 28.4 (OC(CH$_3$)$_3$×2), 37.7 (CH$_3$SO$_2$), 40.5 (C-5), 44.1 (—CH$_2$N—), 68.6, 69.2, 76.3 (C-1, C2, C-4), 79.2 (O C(CH$_3$)$_3$×2), 156.8 (—NH(CO)O—×2); MS m/z (FAB+): 441 (M+H$^+$, 10%).

LiBr (860 mg, 9.89 mmol) was added to a solution of 9 (245 mg, 0.62 mmol) in acetone (25 mL) under N$_2$ and heated under reflux. After 8 h the reaction mixture was cooled and the solvent removed. The residue was partitioned between ether (150 mL) and water (50 mL). The aqueous layer was reextracted with ether (50 mL×2). The organic fractions were combined, dried (MgSO$_4$), filtered and the solvent removed to give 5,5-bis(aminomethyl)-1-bromo-N, N'-di-tert-butoxycarbonyl-3-oxo-hexane (10) (769 mg, 93%) as a yellow oil which was used directly in the next step.

NaSSO$_2$CH$_3$ (315 mg, 2.35 mmol) was added to a solution of 10 (769 mg, 1.81 mmol) in DMF (30 mL) and the resulting solution warmed to 50° C. under N$_2$. After 20 h TLC (EtOAc:hexane, 1:1) showed the conversion of starting material (R$_f$ 0.8) to a major product (R$_f$ 0.35). The solvent was removed and the residue purified by flash chromatography to give (EtOAc:hexane, 1:1) 5,5-Bis(aminomethyl)-N,N'-di-tert-butoxycarbonyl-3-oxo-hexyl methanethiosulfonate (11) (720 mg, 87%) as a colorless oil; IR (film) 3385 (NH), 1700 (amide I), 1508 (amide 11) 1320, 1167 (S—SO$_2$) cm$^{-1}$; $^1$H NMR (CDCl$_3$, 400 MHz) δ0.83 (s, 3H, H-6), 1.42 (s, 18H, OC(CH$_3$)$_3$×2), 2.95 (dd, 2H, J$_{H,NH}$ 6.1 Hz, J$_{H,H'}$ 14.2 Hz, —CHH'N—×2), 3.05 (dd, 2H, J$_{H',H'}$ 7.2 Hz, J$_{H,H'}$ 14.2 Hz, —CHH'N—×2), 3.24 (s, 2H, H-4), 3.34 (s, 3H, CH$_3$SO$_2$), 3.35 (t, 2H, J 4.9 Hz, H-2), 3.71 (t, 2h, J 4.9 Hz, H-1), 5.20 (br s, 2H, NH×2); $^{13}$C NMR (CDCl$_3$, 100 MHz) δ18.7 (C-6), 28.4 (OC(CH$_3$)$_3$×2), 36.2 (C-1), 40.5 (C-5), 44.2 (—CH$_2$N—), 50.6 (CH$_3$SO$_2$), 69.6, 76.2 C-2, C4), 79.2 (OC(CH$_3$)$_3$×2), 156.7 (—NH(CO)O—×2); MS m/z (FAB+): 479 (M+Na$^+$, 8), 457 (M+H$^+$, 10%).

11 (720 mg, 1.58 mmol) was dissolved in DCM (20 mL) under N$_2$ and TFA (20 mL) was added. After 1 h the solvent was removed. The residue was purified by ion exchange chromatography (Dowex 50W(H$^+$), 4×3 cm, eluant aq. HCl, concave gradient 0.5–2.5 M) to give 1c as a white foam (348 mg, 67%); $^1$H NMR (D$_2$O, 400 MHz) δ0.91 (s, 3H, H-6), 2.89 (d, 2H, J$_{H,H'}$ 13.5 Hz, —CHH'N—×2), 2.99 (d, 2H, J$_{H,H'}$ 13.2 Hz, —CHH'N—×2), 3.28 (t, 2H, J 5.6 Hz, H-1), 3.31 (s, 3H, CH$_3$SO$_2$), 3.42 (s, 2H, H-4), 3.63 (t,2H, J 5.9 Hz, H-2); $^{13}$C NMR (D$_2$O, 100 MHz) δ17.8 (C-6), 36.4, 37.1, 45.2 (C-1, C-5, —CH$_2$N—), 50.6 (CH$_3$SO$_2$), 70.1, 75.4 (C-2, C-4); MS m/z (FAB+): 289 (M+Na$^+$, 15), 257 (M+H$^{30}$, 65%). HRMS m/z (FAB+): Found 257.1000 (M+H$^+$); C$_8$H21N$_2$O$_3$S$_2$ requires 257.0994.

4.3 2,2-Bis(aminomethyl)-3-aminopropyl methanethiosulfonate trihydrochloride (1d)

Pentaerythritol (12) (12.8 g, 94 mmol) was dissolved in glacial AcOH/40% HBr (aq.) (1:5 v/v, 60 mL) and heated under reflux. After 24 h 40% HBr (aq.) (50 mL) and c. H$_2$SO$_4$ (23 mL) were added and the resulting solution heated under reflux. After a further 24 h the reaction mixture was cooled. The lower liquid layer from the resulting mixture was separated and dissolved in CHCl$_3$ (50 mL), washed with water (20 mL), dried (anhyd. K$_2$CO$_3$), filtered and the solvent removed. The residue was purified by flash chromatography (EtOAc:hexane, 1:9) to give 2,2-bis (bromomethyl)-3-bromo-propan-1-ol (13) (15.1 g, 49%) as a white crystalline solid; mp 67–69° C. [lit., mp 68–69.5° C. (CCl$_4$)]; $^1$H NMR (200 MHz, CDCl$_3$) δ1.70 (br s, 1H, OH), 3.55 (s, 6H, —CH$_2$Br), 3.75 (d, 2H, J 6 Hz, —CH$_2$OH).

NaN$_3$ (15.7 g, 241.5 mmol) was added to a solution of 13 (6.6 g, 20.3 mmol) in DMF (120 mL) under N$_2$ and the resulting mixture warmed to 100° C. After 28 h the solution formed was cooled, poured into water (1 L) and extracted with Et$_2$O (250 mL then 75 mL×4). The organic fractions were combined, dried (MgSO$_4$), filtered and the volume of solvent reduced to 100 mL. p-Dioxan (200 mL) was added and the volume of solvent reduced again to 100 mL. p-Dioxan (250 mL), PPh$_3$ (26.6 g, 101.4 mmol) and NH$_3$ (aq., 30%, 100 mL) were added with stirring. After 19 h the solvent was removed, the residue suspended in CHCl$_3$ (400 mL) and extracted with HCl (aq., 2.5M, 75 mL×5). The aqueous fractions were combined, washed with CHCl$_3$ (20 mL×4) and concentrated to a volume of 50 mL. c. HCl (aq., 10 mL) was added and the solution cooled to 4° C. The white solid that crystallized from solution was filtered, washed with cold c. HCl (aq., 3 mL), EtOH (3 mL), Et$_2$O (20 mL×5) and dried under vacuum to give 2,2-bis(aminomethyl)-3-amino-propan-1-ol trihydrochloride (15) (2.81 g, 57%) as a white crystalline solid; mp 295–298° C. (dec.) [lit., mp 298° C. (dec.)]; $^1$H NMR (200 MHz, D$_2$O) δ3.28 (s, 6H, —CH$_2$N—), 3.83 (s, 2H, —CH$_2$—).

Et$_3$N (3.3 mL, 23.6 mmol) was added to a suspension of 15 (1.63 g, 6.7 mmol) in MeOH (13 mL) under N$_2$. PhCHO (2.1 mL, 20.8 mmol) was added to the resulting solution and heated under reflux. After 20 min the solution was cooled and the solvent removed. The residue was slurried with water (10 mL) and filtered to give 7-(hydroxymethyl)-2,4,6-triphenyl-1,3,5-triazaadamantane (16) (2.65 g, 99%) as a white solid; R$_f$ 0.5 (EtOAc:hexane, 1:3); mp 91–93° C [lit., mp 92–95° C]; $^1$H NMR (400 MHz, CDCl$_3$) δ2.93 (s, 4H, —CH$_2$N—, —CH$_2$)—), 2.97 (s, 1H, OH), 3.20 (d, J 12.9 Hz, 2H, —CH$_2$N—), 3.50 (d, J 13.2 Hz, 2H, —CH$_2$N—), 5.42 (s, 2H, PhCH$_{ax}$), 5.64 (s,1H, PhCH$_{eq}$), 7.23–7.83 (m, 15H, Ar).

MsCl (0.78 mL, 10.1 mmol) was added dropwise to a solution of 16 (2.65 g, 6.63 mmol) and Et$_3$N (1.9 mL, 13.6 mmol) in CH$_2$Cl$_2$ (15 mL) under N$_2$ at 0° C. the reaction mixture was warmed to room temperature. After 21 h the resulting solution was diluted with CH$_2$Cl$_2$ (150 mL), washed with NaHCO$_3$ (aq., sat., 30 mL), water (30 mL) and brine (30 mL), dried (MgSO$_4$), filtered and the solvent removed. The residue was purified by flash chromatography (EtOAc:hexane, 1:3) to give (2,4,6-triphenyl-1,3,5-triazaadamantanyl)methyl methanesulfonate (2.44 g, 77%) as a white solid; R$_f$ 0.5 (EtOAc:hexane, 1:3); mp 167–170° C. (dec.); IR (KBr) 1440 cm$^{-1}$ (Ar), 1348, 1173 cm$^{-1}$ (O—SO$_2$); $^1$H NMR (400 MHz, CDCl$_3$) δ2.85 (s, 3H, CH$_3$SO$_2$—), 2.96 (s, 2H, —CH$_2$N—), 3.30 (d, J 12.7 Hz, 2H, —CH$_2$N—), 3.50 (s, 2H, —CH$_2$O—), 3.54 (d, J 13.2 Hz, 2H, —CH$_2$N—), 5.45 (s, 2H, PhCH$_{ax}$), 5.64 (s, 1H, PhCH$_{eq}$), 7.33–7.80 (m, 15H, Ar); $^{13}$C NMR (100 MHz, CDCl$_3$) δ26.3 (C-7), 37.1 (CH$_3$SO$_2$—), 45.9, 54.6, 73.5 (—CH$_2$O—, —CH$_2$N—) 75.3, 82.8 (PhCH—), 126.5 126.6, 127.4, 127.6, 128.8, 129.0, 139.1, 139.4 (Ar); HRMS m/z (FAB+): Found 476. 1996 (M+H$^+$); C$_{27}$H$_{30}$N$_3$O$_3$S requires 476.2008.

LiBr (3.2 g, 36.8 mmol) was added to a solution of this mesylate (2.44 g, 5.10 mmol) in dry acetone (30 mL) under N$_2$ and heated under reflux. After 22 h TLC (EtOAc:hexane, 1:3) showed the loss of starting material (R$_f$ 0.5) and the formation of a major product (R$_f$ 0.8). The reaction mixture was cooled and the solvent removed. The residue was partitioned between Et$_2$O (200 mL) and brine (50 mL), dried (MgSO$_4$), filtered and the solvent removed. The residue was purified by flash chromatography (EtOAc:hexane, 2:23) to give 7-(bromomethyl)-2,4,6-triphenyl-1,3,5-triazaadamantane (1.82 mg, 78%) as a yellow oil; R$_f$ 0.8 (EtOAc:hexane, 1:3) which was used directly in the next step.

NaSSO$_2$CH$_3$ (440 mg, 3.28 mmol) was added to a solution of this bromide (1.1 g, 2.38 mmol) in DMF (35 mL) under N$_2$ and the resulting solution heated to 80° C. After 96 h TLC (EtOAc:hexane, 1:3) showed the loss of starting material (R$_f$ 0.8) and the formation of a major product (R$_f$ 0.2). The solution was cooled and the solvent removed. The residue was purified by flash chromatography (EtOAc:hexane, 1:3) to give (2,4,6-triphenyl-1,3,5-triazaadamantanyl)methyl methanethiosulfonate (17) (759 mg, 65%) as a colorless oil; IR (film) 1451 cm$^{-1}$ (Ar), 1323, 1132 cm$^{-1}$ (S—SO$_2$); $^1$H NMR (400 MHz, CDCl$_3$) δ2.63 (s, 2H, —CH$_2$S—), 2.98 (s, 2H, —CH$_2$N—), 3.18 (s, 3H, CH$_3$SO$_2$—), 3.24 (d, 2H, J 13.2 Hz, —CH$_2$N—), 3.51 (d, 2H, J 13.2 Hz, —CH$_2$N—), 5.44 (s, 2H, PhCH$_{ax}$), 5.63 (s, 1H, PhCH$_{eq}$), 7.22–7.83 (m, 15H, Ar); $^{13}$C NMR (100 MHz, CDCl$_3$) δ26.4 (C-7), 43.0, 48.7, 56.6 (—CH$_2$O—, —CH$_2$N—), 50.3 (CH$_3$SO$_2$—), 75.1, 82.7 (PhCH—), 126.5, 126.6, 127.5, 127.6, 128.9, 129.0, 139.1, 139.3 (Ar); HRMS m/z (FAB+): Found 492.1768 (M+H$^+$); C$_{27}$H$_{30}$N$_3$O$_2$S$_2$ requires 492.1779.

Conc. HCl (aq., 50 drops) was added to a solution of 17 (759 mg, 1.54 mmol) in EtOH/Et$_2$O (5/1 v/v, 24 mL) and the resulting solution cooled to 4° C. After 1 h, the white solid that crystallized from solution was filtered, washed with cold EtOH and Et$_2$O and dried under vacuum to give 1d (358 mg, 69%) as a fine white powder; mp 199–204° C. (dec.); IR (KBr) 2890, 1605, 1513 cm$^{-1}$ (NH$_3^+$), 1284, 1123 cm$^{-1}$ (S—SO$_2$); $^1$H NMR (400 MHz, D$_2$O) δ3.17 (s, 6H, —CH$_2$N—), 3.38 (s, 3H, CH$_3$SO$_2$—), 3.44 (s, 2H, —CH$_2$S—); $^{13}$C NMR (100 MHz, CDCl$_3$) δ37.0 (C-2), 40.7, 40.8 (—CH$_2$S—, —CH$_2$N—), 50.6 (CH$_3$SO$_2$—); HRMS m/z (FAB+): Found 228.0844 (M+H$^+$); C$_6$H$_{18}$N$_3$O$_2$S$_2$ requires 228.0840.

Site-specific Chemical Modification

To approximately 25 mg of each of the SBL mutants in CHES buffer (2.5 mL; 70 mM CHES, 5 mM MES, 2 mM CaCl$_2$, pH 9.5) at 20° C. was added each of the methanethiosulfonate reagents (100 μL of a 0.2 M solution in water), in a PEG(MW 10,000)-coated polypropylene test tube and mixed using an end-over-end rotator. The progress of modification was followed using specific activity measurement, monitored spectrophotometrically (10 μL aliquots in 0.1 M Tris-HCl buffer, pH 8.6, 0.005% Tween 80, and 1% DMSO, with succinyl-AAPF-pNA (1 mg/mL) as substrate at 25° C., $\epsilon_{410}$=8800 M$^{-1}$ cm$^{-1}$) (Bonneau et al. (1991) *J. Am. Chem. Soc.*119: 1026–1030) on a Perkin-Elmer Lambda 2 spectrophotometer. The reaction was terminated when the addition of a further 100 μL of methanethiosulfonate solution gave no further change in specific activity, typically after 2 to 3 h. The reaction solution was purified on a disposable desalting column (Pharmacia Biotech PD-10, Sephadex G-25 M) pre-equilibrated with MES buffer (5 mM MES, 2 mM CaCl$_2$, pH 6.5). The CMM was eluted with this buffer (3.5 mL), dialyzed against MES buffer (10 mM MES, 1 mM CaCl$_2$ pH 5.8, 1 L×3) at 4° C. and subsequently flash frozen and stored at −18° C. The free thiol content of all CMMs, was determined spectrophotometrically by titration with Ellman's reagent ($\epsilon_{412}$=13600 M$^{-1}$ cm$^{-1}$) in phosphate buffer 0.25 M, pH 8.0. In all cases no free thiol was detected. Modified enzymes were analyzed by nondenaturing gradient (8–25%) gels at pH 4.2, run towards the cathode, on the Pharmacia Phast-system and appeared as a single band. Each of the CMMs showed increased mobility relative to wild-type. Prior to ES-MS analysis CMMs were purified by FPLC (BioRad, Biologic System) on a Source 15 RPC matrix (17-0727-20 from Pharmacia) with 5% acetonitrile, 0.01% TFA as the running buffer and eluted with 80% acetonitrile, 0.01% TFA in a one step gradient. MS m/z (ES-MS): N62C-a (Berglund et al. (1997) *J. Am. Chem. Soc.* 119: 5265–5266) calculated 26763, found 26764; S156C-a (DeSantis et al. (1998) *Biochem.* 37: 5968–5973) calculated 26790, found 26791; S166C-a (Id.) calculated 26790, found 26784; L217C-a (Berglund et al. (1997) *J. Am. Chem. Soc.*

119: 5265–5266) calculated 26764, found 26764; N62C-b calculated 26805, found 26808; S156C-b calculated 26832, found 26835; S166C-b calculated 26832, found 26835; L217C-b calculated 26806, found 26808; N62C-c calculated 26863, found 26863; S156C-c calculated 26890, found 26892; S166C-c calculated 26890, found 26899; L217C-c calculated 26864, found 26869; N62C-d calculated 26834, found 26835; S156C-d calculated 26861, found 26866; S166C-d calculated 26861, found 26862; L217C-d calculated 26835, found 26837.

Active Site Titrations

The active enzyme concentration was determined as previously described (Hsia et al. (1996) Anal. Biochem. 242: 221–227) by monitoring fluoride release upon enzyme reaction with α-toluenesulfonyl fluoride (PMSF) as measured by a fluoride ion sensitive electrode (Orion Research 96–09). The active enzyme concentration determined in this way was used to calculate $k_{cat}$ values for each CMM.

Kinetic Measurements

Michaelis-Menten constants were measured at 25(±0.2)° C. by curve fitting (GraFit® 3.03) of the initial rate data determined at eight or nine concentrations (0.125 mM–4.0 mM) of succinyl-AAPF-pNA substrate in 0.1 M Tris-HCl buffer containing 0.005% Tween 80, 1% DMSO, pH 8.6 ($\epsilon_{440}$=8800 $M^{-1}cm^{-1}$) (Bonneau et al. (1991) *J. Am. Chem. Soc.*119: 1026–1030).

Example 3

Tailoring the Specificity of the $S_1$ Pocket of Subtilisin *B. lentus*: Chemical Modification of Mutant Enzymes as a Strategy for Removing Specificity Limitations In both protein chemistry studies and organic synthesis applications, it is desirable to have available a toolbox of inexpensive proteases with high selectivity and diverse substrate preferences. This example describes the generation of a series of chemically modified mutant enzymes (CMMs) of subtilisin *B.lentus* (SBL) possessing expanded $S_1$ pocket specificity. Wild-type SBL shows a marked preference for substrates with large hydrophobic $P_1$ residues, such as the large Phe $P_1$ residue of the standard suc-AAPF-pNA substrate. In order to confer more universal $P_1$ specificity on $S_1$, a strategy of chemical modification of mutant enzymes was applied. For example, WT-SBL does not readily accept small uncharged $P_1$ residues such as the —$CH_3$ side chain of alanine. Accordingly, with a view to creating a $S_1$ pocket that would be of reduced volume providing a better fit for small $P_1$ side chains, a large cyclohexyl group was introduced by the CMM approach at position S166C with the aim of partially filling up the Si pocket. The S166C-S—$CH_2$-c-$C_6H_{11}$ CMM thus created showed a 2-fold improvement in $k_{cat}/K_M$ with the suc-AAPA-pNA substrate and a 51-fold improvement in suc-AAPA-pNA/suc-AAPF-pNA selectivity relative to WT-SBL. Furthermore, WT-SBL does not readily accept positively or negatively charged $P_1$ residues. Therefore, to improve SBL's specificity toward positively and negatively charged $P_1$ residues, we applied the CMM methodology to introduce complementary negatively and positively charged groups respectively at position S166C in $S_1$. A series of mono-, di-, and tri-negatively charged CMMs were generated and all showed improved $k_{cat}/K_MS$ with the positively charged $P_1$ residue containing substrate, suc-AAPR-pNA. Furthermore, virtually arithmetic improvements in $k_{cat}/K_M$ were exhibited with increasing number of negative charges on the S166C-R side chain. These increases culminated in a 9-fold improvement in $k_{cat}/K_M$ for the suc-AAPR-pNA substrate and a 61-fold improvement in suc-AAPR-pNA/suc-AAPF-pNA selectivity compared to WT-SBL for the tri-negatively charged S166C-S—$CH_2CH_2C(COO^-)_3$ CMM. Conversely, the positively charged S166C-S—$CH_2CH_2NH_3^+$ CMM generated showed a 19-fold improvement in $k_{cat}/K_M$ for the suc-AAPE-pNA substrate and a 54-fold improvement in suc-AAPE-pNA/suc-AAPF-pNA selectivity relative to WT-SBL.

Figure 9:
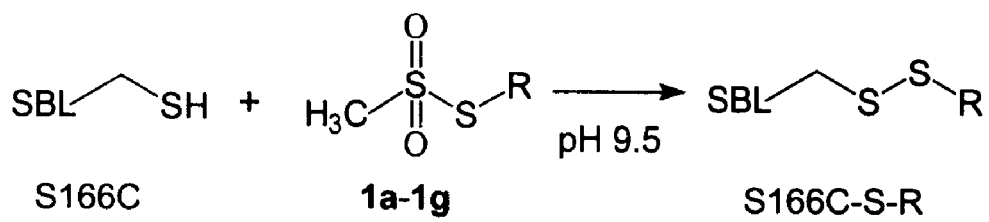
FIG. 9 show scheme 5 for the preparation of chemically modified mutant enzymes (CMMs) having multiply charged substituents. This approach entails the introduction of a unique cysteine residue at a selected position, followed by its chemical modification with methanethiosulfonate reagents (e.g., MTS, 1a–1j) to generate chemically modified mutant enzymes (CMMs).
Figure 9:
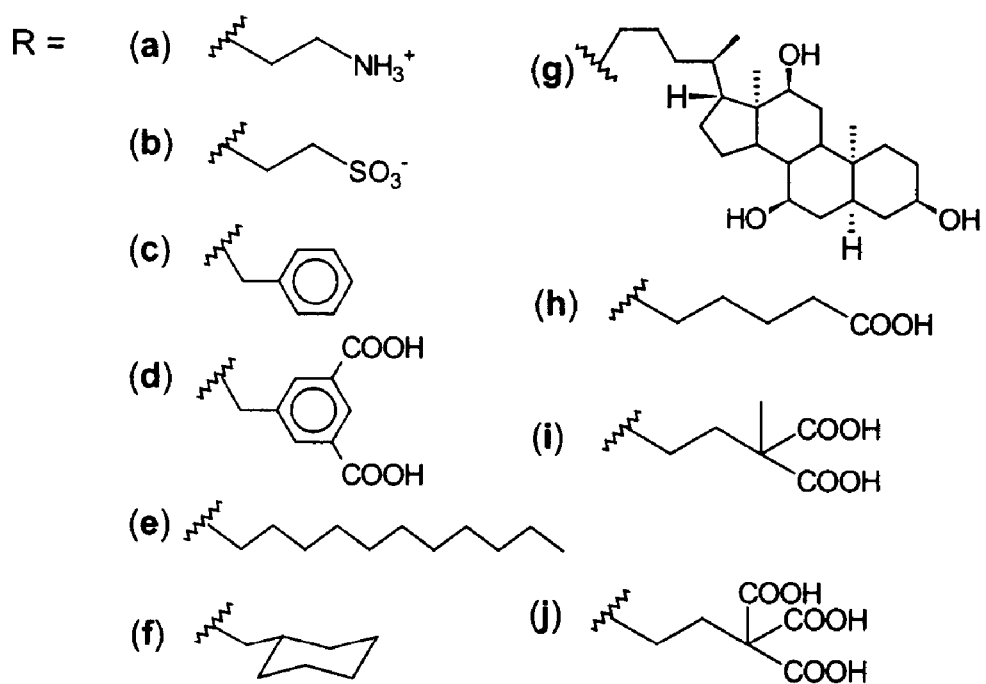

In this example, we exploit strategy of applying a combination of site-directed mutagenesis and chemical modification to modify enzyme specificity. This approach This approach is illustrated in Scheme 5 (FIG.9) and entails the introduction of a unique cysteine residue at a selected position, followed by its chemical modification with methanethiosulfonate (Kenyon and Bruice (1977) *Meth. Enzymol.* 47: 407–430; Wynn and Richards (1995) *Meth. Enzymol.* 251: 351–356; Brocklehurs (1979) *Int.J. Biochem.*10: 259–274) reagents (MTS, 1a–1j) to generate chemically modified mutant enzymes (CMMs). The combination of site-directed mutagenesis and chemical modification has previously been recognized as a powerful tool for the creation of new active-site environments (Sorensen et al. (1993) *Biochemistry* 32: 8994–8999; Bech and Breddam (1988) *Carlsberg Res.Commun.* 53: 381–393), in mechanistic studies (Gloss and Kirsch (1995) *Biochemistry* 34: 12323–12332; Smith and Hartman (1966)*J. Biol. Chem.*263 (10): 4921–4925), for the investigation of protein packing (Wynn et al. (1996) *Protein Sci.* 5: 1026–1031), and for cofactor incorporation (Kuang et al. (1996) *J. Am. Chem. Soc.*118: 10702–10706). This approach has also been applied to detailed studies of ion-channel properties (Foong et al. (1996) *Biochemistry* 36: 1343–1348; Holmgren et al. (1996) *Neuropharmacology* 35: 797–804; Yang et al. (1996) *Neuron* 16: 113–122) for site-directed introduction of spin-labels (Hubbell et al. (1996) *Structure* 4: 779–783; Lin et al. (1998) *Science* 279(5358): 1925–1929), to probe receptor binding (Heinonen et al. (1998) *Bioconjugate Chem.* 9: 358–364), and in investigations of membrane spanning proteins (Akabas et al. (1994) *Neuron* 13: 913–927; Chen et al. (197) *Biochemistry* 36: 1479–1486).

The subtilisin from *Bacillus lentus* (SBL, EC 3.4.21.14) is well suited as an exploratory vehicle for evaluating the potential of this combined site-directed mutagenesis chemical modification approach since it is a well characterized enzyme and is of synthetic (Shao and Arnold (1996) *Cur. Opin. Struct. Biol.* 6: 513–518; Lloyd et al (1998) *Tetrahedron: Asymmetry* 9(4): 551–561) as well as industrial (van der Osten et al. (1993) *Biotechnol* 28(1): 55–68) interest. Furthermore, SBL's high resolution crystal structure has been solved (Knapp et al. Brookhaven Database Entry 1*JEA*; Kuhn et al. (1998) *Biochemistry* 37 (39): 13446–13452), it has been cloned, over expressed and purified (Stabile et al. (1996) *Bioorg. Med. Chem. Lett.*6 (21): 2501–2506), and its kinetic behavior well characterized (Grøn: H. et al. (1992) *Biochemistry* 31(26): 6011–6018; Egmond et al. (1994) *Protein Eng.*7(6): 793–800; Maurer et al. (1996) *Adv. Exp. Med. Biol.* 379: 243–256; Olsen et al. (1996) *Adv. Exp. Med. Biol.* 379: 235–241). In addition, and importantly, wild type (WT) SBL contains no natural cysteine residues, and methanethiosulfonate reagents therefore react only with the introduced cysteine residue. The validity of the CMM approach for altering the stability (Grøn et al. (1990) *Eur. J. Biochem.* 194: 897–901), specificity (Bech et al. (1993) *Biochemistry* 32: 2845–2852), kinetic properties (Berglund et al. (1996) *Bioorg. Med. Chem. Lett.* 6(21): 2507–2512; Berglund et al. (1997) *J. Am. Chem. Soc.* 119: 5265–5266; DeSantis et al. (1998) *Biochemistry* 37: 5968–5973; Plettner et al. (1998) *Biorg. Med. Chem. Lett.*8(17): 2291–2296), and pH-profiles (DeSantis and Jones (1998) *J. Am. Chem. Soc.* 120(34): 8582–8586) of subtilisins has been recognized.

WT-SBL has a marked preference for substrates with large hydrophobic uncharged $P_1$ residues. In this study, we explore tailoring of the $S_1$ pocket of SBL to also accept small hydrophobic, positively charged, and negatively charged $P_1$ residues. In order to achieve this broadened $P_1$ tolerance, a simplistic strategy of steric and electrostatic complementarity was applied (Fersht (1985) *A. Enzyme Structure and Mechanism:* 2nd ed.; W.H. Freeman and Company: New York). Employing the crystal structure of SBL as our guide (Knapp et al. *Brookhaven Database Entry* 1*JEA*), the Ser166 residue, which is located at the bottom of the $S_1$ pocket and whose side chain points inward toward the pocket, was chosen for mutagenesis to cysteine and subsequent chemical modification. Firstly, to expand SBL's specificity toward small uncharged $P_1$ residues, such as the small $P_1$ Ala residue of the suc-AAPA-pNA substrate, we introduced large moieties at position 166 in $S_1$, such as benzyl (-c), decyl (-e), cyclohexyl (-f) and steroidyl (-g) groups with a view to reducing the volume of $S_1$ and inducing a better fit of small $P_1$ groups, thereby conferring elastase-like (Bode et al. (1989) *Biochemistry* 28(5): 1951–1963) substrate specificity on SBL. Then, to expand SBL's specificity toward positively charged $P_1$ residues, such as the $P_1$ Arg residue of the suc-AAPR-pNA substrate, we introduced negatively charged groups at position S166C in $S_1$, such as the ethylsulfonato (-b) moiety, and the dicarboxylic aromatic (-d) and aliphatic mono- (h) di- (i) and tri (-j) aliphatic groups, to elicit complementary electrostatic attractions with a view to making SBL trypsin-like in its specificity (Perona et al. (1995) *Biochemistry* 7(34): 1489–1499). Conversely, to expand SBL's specificity toward negatively charged $P_1$ residues, such as the negatively charged $P_1$ Glu residue of the suc-AAPE-pNA substrate, we introduced the positively charged ethylamino (-a) group at position S166C in $S_1$.

Results

The preparations of the requisite MTS reagents 1c (Berglund et al. (1997) *J. Am. Chem. Soc.* 119: 5265–5266), 1e–f (Id.) and 1d (Berglund et al. (1997) *J. Am. Chem. Soc.* 119: 5265–5266; Examples 1 and 2), 1i–j (Id.) are as reported, and the steroidyl MTS reagent 1g was prepared from cholic acid by the same methodology.

Each of the CMMs obtained was characterized in order to establish its purity and integrity. Titration of the CMMs with Ellman's reagent showed a residual thiol content of less than 2% in all cases, demonstrating that the MTS reactions were virtually quantitative. Mass analyses of the CMMs by electrospray mass spectrometry were consistent (±6 Da) with the calculated masses. The purities of the modified enzymes were assessed by native-PAGE and in all cases only one band was visible. Furthermore, as expected relative to WT, the negatively charged CMMs S166C-S-b,-d, and -i to -j displayed retarded mobility in the direction of the cathode, while the positively charged S166C-S-a CMM displayed greater mobility. That modification of cysteine is wholly responsible for altered activity was established by the absence of reaction of WT-SBL with the MTS reagents. Also, the modifications are fully reversible by treatment of each of the CMMs with β-mercaptoethanol, further verifying that chemical modification at cysteine was solely responsible for the observed changes in activity. The total amount of active enzyme was determined by titration with phenylmethanesulfonyl fluoride (Hsia et al. (1996) *J. Anal. Biochem.* 242: 221–227).

Figure 10:
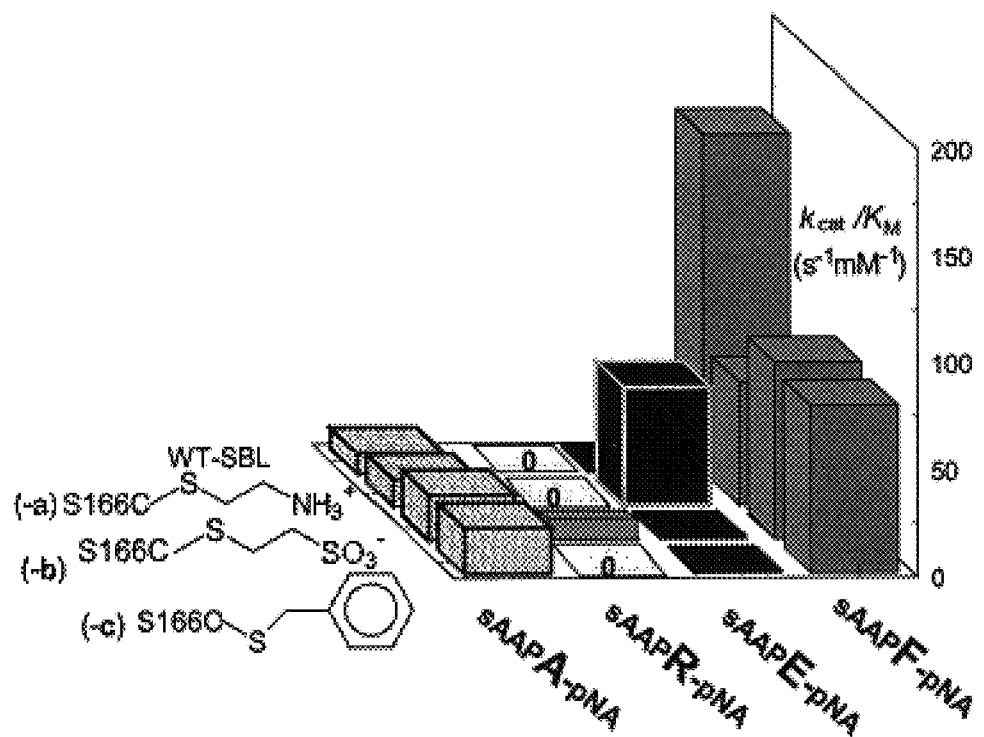
FIG. 10 shows the $k_{cat}/K_M$ screen of WT-SBL and S 166C-S-a to -c CMMs with each of the standard suc-AAPF-pNA substrate and with the suc-AAP-A/R/E-pNA substrates.

Initially, three CMMs S166C-S-a, -b and -c, with a positive, a negative, and with a large hydrophobic side chain respectively, were subjected to a $k_{cat}/K_M$ screen with each of the test substrates, suc-AAP-F/A/R/E-pNA in order to identify any induced complementary electrostatic or improved hydrophobic interactions (FIG. 10). While as expected $k_{cat}/K_M$ s with the standard suc-AAPF-pNA were lowered, the $k_{cat}/K_M$s of the CMMs whose $S_1$ sites were tailored toward the Ala, Arg, and Glu $P_1$ residues, improved with the appropriate substrate. This is illustrated in FIG. 10 in the higher activity of S166C-S-c with suc-AAPA-pNA, of S166C-S-b with suc-AAPR-pNA, and of S166C-S-a with suc-AAPE-pNA, all relative to WT.

Following the validation of the general design strategy from this initial screen, more complete kinetic analyses were undertaken. The substrate specificity of each of the CMMs was evaluated kinetically with the standard large hydrophobic $P_1$ residue containing substrate, suc-AAPF-pNA. In addition, the S166C CMMs modified with the large hydrophobic MTS reagents 1c, 1e–g, were evaluated with the small hydrophobic $P_1$ residue containing substrate, suc-AAPA-pNA. The S166C CMMs modified with the negatively charged MTS reagents 1b, 1d, 1h–1j were evaluated with the positively charged $P_1$ residue containing substrate, suc-AAPR-pNA. The S166C CMM modified with the positively charged MTS reagent 1a was evaluated with the negatively charged $P_1$ residue containing substrate, suc-AAPE-pNA. The results are summarized in Table 3.

TABLE 3

Kinetic Evaluation[a] of Altered $S_1$ Pocket Specificity

| Entry | Enzyme | Substrate | $K_M$ mM | $k_{cat}$ $s^{-1}$ | $k_{cat}/K_M$ $s^{-1}$ $mM^{-1}$ |
|---|---|---|---|---|---|
| 1 | WT | suc-AAPF-pNA | 0.73 ± 0.08 | 153 ± 4 | 209 ± 15 |
| 2 | S166C-S-a | suc-AAPF-pNA | 0.68 ± 0.04 | 50 ± 1 | 74 ± 5 |
| 3 | S166C-S-b | suc-AAPF-pNA | 1.34 ± 0.08 | 25.0 ± 0.7 | 19 ± 1 |
| 4 | S166C-S-c | suc-AAPF-pNA | 1.17 ± 0.06 | 23.1 ± 0.5 | 20 ± 1 |
| 5 | S166C-S-d | suc-AAPF-pNA | 1.6 ± 0.2 | 47 ± 3 | 29 ± 4 |
| 6 | S166C-S-e | suc-AAPF-pNA | 1.09 ± 0.07 | 82 ± 2 | 75 ± 5 |
| 7 | S166C-S-f | suc-AAPF-pNA | 0.70 ± 0.05 | 4.8 ± 0.1 | 6.90 ± 0.05 |
| 8 | S166C-S-g | suc-AAPF-pNA | 0.74 ± 0.07 | 29 ± 1 | 41 ± 4 |
| 9 | S166C-S-h[b] | suc-AAPF-pNA | 1.52 ± 0.06 | 48 ± 1 | 31 ± 1 |
| 10 | S166C-S-i[b] | suc-AAPF-pNA | 2.26 ± 0.10 | 67 ± 2 | 30 ± 2 |
| 11 | S166C-S-j[b] | suc-AAPF-pNA | 2.46 ± 0.11 | 76 ± 2 | 31 ± 2 |
| 12 | WT | suc-AAPA-pNA | 2.0 ± 0.1 | 17.7 ± 0.3 | 8.8 ± 0.4 |
| 13 | S166C-S-c | suc-AAPA-pNA | 0.8 ± 0.1 | 6.8 ± 0.3 | 9 ± 1 |
| 14 | S166C-S-e | suc-AAPA-pNA | 1.90 ± 0.03 | 6.8 ± 0.4 | 3.6 ± 0.6 |

TABLE 3-continued

Kinetic Evaluation[a] of Altered $S_1$ Pocket Specificity

| Entry | Enzyme | Substrate | $K_M$ mM | $k_{cat}$ $s^{-1}$ | $k_{cat}/K_M$ $s^{-1}$ $mM^{-1}$ |
|---|---|---|---|---|---|
| 15 | S166C-S-f | suc-AAPA-pNA | 1.90 ± 0.07 | 28.2 ± 0.4 | 14.8 ± 0.6 |
| 16 | S166C-S-g | suc-AAPA-pNA | 1.74 ± 0.04 | 9.65 ± 0.07 | 5.54 ± 0.3 |
| 17 | WT | suc-AAPR-pNA | 7.2 ± 0.7 | 0.16 ± 0.01 | 0.022 ± 0.002 |
| 18 | S166C-S-b | suc-AAPR-pNA | 3.4 ± 0.3 | 0.17 ± 0.01 | 0.050 ± 0.005 |
| 19 | S166C-S-d | suc-AAPR-pNA | 5.5 ± 1.1 | 0.68 ± 0.08 | 0.12 ± 0.03 |
| 20 | S166C-S-h | suc-AAPR-pNA | 8.2 ± 0.9 | 0.35 ± 0.02 | 0.041 ± 0.005 |
| 21 | S166C-S-i | suc-AAPR-pNA | 5.3 ± 0.5 | 0.43 ± 0.02 | 0.080 ± 0.008 |
| 22 | S166C-S-j | suc-AAPR-pNA | 5.2 ± 0.6 | 1.06 ± 0.07 | 0.20 ± 0.03 |
| 23 | WT | suc-AAPE-pNA | 4.4 ± 0.4 | 1.75 ± 0.08 | 0.40 ± 0.04 |
| 24 | S166C-S-a | suc-AAPE-pNA | 1.9 ± 0.1 | 14.5 ± 0.3 | 7.6 ± 0.4 |

[a]Michaelis-Menten constants were measured by the initial rates method in pH 8.6 Tris-HCl buffer at 25° C. with suc-AAPF-pNA as the substrate.
[b]Based on total protein concentration. Certain inconsistencies between active enzyme concentration as determined by active site titration with PMSF (Hsia et al. (1996) J. Anal. Biochem. 242: 221–227) and total protein concentration have been reported for negatively charged mutants of SBL. These are characterized by sluggish fluoride ion concentration bursts and high rates of background PMSF hydrolysis. Active enzyme concentration values for S166C-S-h, S166C-S-i, and S166C-S-j were low and gave rise to anomalous values for kcat. Consequently the values shown were calculated using total protein concentration as determined by absorbance at 280 mn ($\epsilon_{280}$ = 23000 M-1 cm-1) (Grøn et al. (1990) Eur. J. Biochem. 194: 897–901). The $K_M$ values determined are not concentration dependent.
[c]a = 2-aminoethyl;
b = sulfonatoethyl;
c = $CH_2C_6H_5$;
d = $CH_2C_6H_4$-3,5-$(COO^-)_2$;
e = $CH_2(CH_2)_8CH_3$;
f = $CH_2C_6H_{11}$;
g = steroidyl;
h = $CH_2(CH_2)_2CH_2COO^-$;
i = $CH_2C(CH_3)(COO^-)_2$;
j = $CH_2CH_2C(COO^-)_3$.

Discussion

The significant substrate preference of WT-SBL for large hydrophobic $P_1$ residues is apparent from its preference for the Phe $P_1$ residue of the standard suc-AAPF-pNA substrate, by a factor of 9500-fold over the small $P_1$ residue of suc-AAPA-pNA, by a factor of 24-fold compared to the positively charged $P_1$ residue of suc-AAPR-pNA, and by a factor of 522-fold compared to the negatively charged $P_1$ residue of suc-AAPE-pNA (Table 3, entries 1,12,17 and 23). These kinetic differences are due to changes in both binding, as reflected by $K_M$, and in turnover number, $k_{cat}$. Moreover, and predictably, the WT enzyme is by far the best catalyst with suc-AAPF-pNA, and its conversions to any of the CMMs were deleterious with respect to this substrate and resulted in $k_{cat}/K_M$ decreases of up to 34-fold (Table 3, entries 2–11).

To improve the substrate specificity of SBL toward small hydrophobic $P_1$ residues such as Ala, the simplistic approach of filling up the $S_1$ binding cleft was addressed by preparing the S166C-S—$CH_2C_6H_5$ (-c), S166C-S—$CH_2(CH_2)_8CH_3$ (-e), S166C-S—$CH_2C_6H_{11}$ (-f), and S166C-S-steroidyl (-g) CMMs. This design strategy attempted to mimic the function of the bulky $S_1$-pocket side chains of α-lytic protease (Bone et al. (1989) *Biochemistry* 28: 7600–7609; Bone et al. (1991) *Biochemistry* 30: 10388–10398; Bauer et al. (1981) *Eur. J. Biochem.* 120: 289–294), and of elastase (Bode et al. (1989) *Biochemistry* 28(5): 1951–1963), which are responsible for their substantial preference for the small $P_1$-group containing suc-AAPA-pNA substrate over the large $P_1$-group containing suc-AAPF-pNA substrate (Bone et al. (1989) *Biochemistry* 28: 7600–7609; Bone et al. (1991) *Biochemistry* 30: 10388–10398; Bauer et al. (1981) *Eur. J. Biochem.* 120: 289–294; Bode et al. (1989) *Biochemistry* 28(5): 1951–1963). The se CMMs (S166C-S-c,-e,-f, -g. Table 3, entries 12–16) were then evaluated with the suc-AAPA-pNA substrate. All revealed slightly improved binding compared to WT, with the greatest improvement in $K_M$ being 2-fold for the S166C-S—$CH_2C_6H_5$ (-c) CMM. However, of these four CMMs, only S166C-S—$CH_2C_6H_{11}$ (-f) showed both an improved $k_{cat}$ and an improved $k_{cat}/K_M$. While this design strategy yielded only one CMM with an increased preference for the small Ala $P_1$ residue, all of these modifications effectively excluded the larger Phe $P_1$ residue preferred by WT-SBL (Table 3, entries 4, 6–8).Overall the selectivities with respect to $k_{cat}/K_M$ for the suc-AAPA-pNA substrate compared to the suc-AAPF-pNA substrate were improved by 11-fold for S166C-S—$CH_2C_6H_5$ (-c), 1.1-fold for S166C-S—$CH_2(CH_2)_8CH_3$ (-e), 51-fold for S166C-S—$CH_2C_6H_{11}$ (-f), and 3.2-fold for S166C-S-steroidyl (-g), all compared to WT. These differences in $P_1$ Ala selectivity may be a reflection of the orientation of the R side-chain of the CMM, with the side-chains of S166C-S—$CH_2C_6H_5$ (-c), and —$CH_2C_6H_{11}$ (-f), behaving as though directed into the pocket and favoring $P_1$=Ala, whereas the side chains of S166C-S—$CH_2(CH_2)_8CH_3$ (-e) and S166C-S-steroidyl (-g) behave as though directed outward, thus not significantly altering the shape of the $S_1$ pocket.

The above improvements in $P_1$ Ala acceptance, although modest, are encouraging and demonstrate the effectiveness of the adopted strategy. Tailoring the steric complementarity between enzymes and substrates has already been found to be challenging and comparison of these CMM results with previous literature studies targeting the same goal are both interesting and intriguing. For example, the G166I mutation of subtilisin BPN' effected an almost 1000-fold decrease in $k_{cat}/K_M$ with the $P_1$=Phe suc-AAPF-pNA substrate. However, this same G166I mutant, which was by far the most effective mutation, elicited a 10-fold improved $k_{cat}/K_M$ compared to WT with the $P_1$=Ala suc-AAPA-pNA substrate (Estell et al. (1986) *Science* 233: 659–663). Notably, the G166I subtilisin mutant is more selective for Ala over Phe than is our most selective CMM. However, in both cases the increases in selectivity are due mainly to decrease in $k_{cat}/K_M$ for suc-AAPF-pNA rather than increases in $k_{cat}/K_M$ for suc-AAPA-pNA. Both the results for both CMM and SDM approaches agree that decreasing the selectivity of an enzyme for a large hydrophobic residue containing substrate can be accomplished in a relatively facile manner by the introduction of large amino acid in the enzyme pocket, but that increasing the selectivity of an enzyme for a small hydrophobic residue containing substrate is much more difficult. Similarly, the G127A mutant of subtilisin YaB, whose specificity was already elastase-like, effected a 10-fold improvement in $k_{cat}/K_M$ with the suc-AAPA-pNA substrate (Mei et al. (1998) *Protein Eng.* 11(2): 109–117). However, the G127V mutant of subtilisin E induced a decrease in $k_{cat}/K_M$ with the suc-AAPA-pNA substrate, identifying an inconsistency in the SDM strategy (Takagi et al. (1996) *FEBS Lett.* 395: 127–132). Thus the CMM approach offers a complementary alternative to conventional site-directed mutagenesis toward the goal of tailoring the steric complementarity between enzymes and substrates (Takagi et al. (1997) *Protein Eng.* 10(9): 985–989).

Improving the substrate specificity of SBL toward positively charged $P_1$ residues such as Arg, was based on mimicking the common motif in trypsin-like enzymes (Knapp et al. *Brookhaven Database Entry* 1JEA) of high negative charge density of acidic residues that favor binding of positively charged substrate structures (Perona et al. (1995) *Biochemistry* 7(34): 1489–1499; Nakayama (2997) *Biochem J.* 327: 625–635). This goal was addressed by S166C-S—$CH_2CH_2SO_3^-$ (-b), S166C-S—$CH_2(CH_2)_2CH_2COO^-$ (-h), S166C-S—$CH_2C_6H_4$-3,5-$(COO^-)_2$ (-d), S166C-S—$CH_2CH_2C(CH_3)(COO^-)_2$ (-i) and S166C-S—$CH_2CH_2C(COO^-)_3$ (-j), a series of CMMs which provide a $S_1$ pocket which is potentially mono-, di-, and tri-negatively charged. Evaluation of each of these CMMs with the suc-AAPR-pNA substrate revealed $K_M$s that were up to 2-fold improved compared to WT (Table 3, entries 17–22). The general success of this approach is evident since all of the CMMs with a negatively charged –R side-chain showed improved activity compared to WT with an up to 7-fold improved $k_{cat}$ and an up to 9-fold improved $k_{cat}/K_M$ with the suc-AAPR-pNA substrate (Table 1: entries 17–22). Overall, the selectivities, with respect to $k_{cat}/K_M$, for the suc-AAPR-pNA substrate compared to the suc-AAPF-pNA substrate were improved 25-fold for S166C-S—$CH_2CH_2SO_3^-$ (-b), 13-fold for S166C-S—$CH_2(CH_2)_2CH_2COO^-$ (-h), 39-fold for S166C-S—$CH_2C_6H_4$-3,5-$(COO^-)_2$ (-d), 25-fold for S166C-S—$CH_2CH_2C(CH_3)(COO^-)_2$ (-i) and 61-fold for S166C-S—$CH_2CH_2C(COO^-)_3$ (-j) relative to WT.

The strategy of introducing charge complementarity to induce trypsin-like $P_1$ specificity in subtilisins has previously been explored using site-directed mutagenesis (SDM) (Wells et al. (1987) *Proc. Nat. Acad. Sci. USA*, 84: 1219–1223; Ballinger et al. (196) *Biochemistry* 33: 13579–13585; Bonneau et al. (1991) *J. Am. Chem. Soc.* 113: 1026–1030). Interestingly however, the G166D and G 166E mutants of subtilisin BPN' caused decreases in $k_{cat}K_M$ with the suc-AAPK-pNA substrate rather than the anticipated increases (Wells et al. (1987) *Proc. Nat. Acad. Sci. USA*, 84: 1219–1223). Furthermore, while the G166D subtilisin BPN' mutant was reported to exhibit a 18-fold improvement in Arg/Phe $P_1$ selectivity this was accompanied by a 2.5-fold decrease in $k_{cat}/K_M$ with the suc-AAPR-pNA substrate compared to WT (Ballinger et al. (196) *Biochemistry* 33: 13579–13585). Thus, compared to WT, both with respect to improved $k_{cat}/K_M$ with the suc-AAPR-pNA substrate and improved Arg/Phe $P_1$ selectivity, the CMMs reported herein are more successful.

Figure 11:
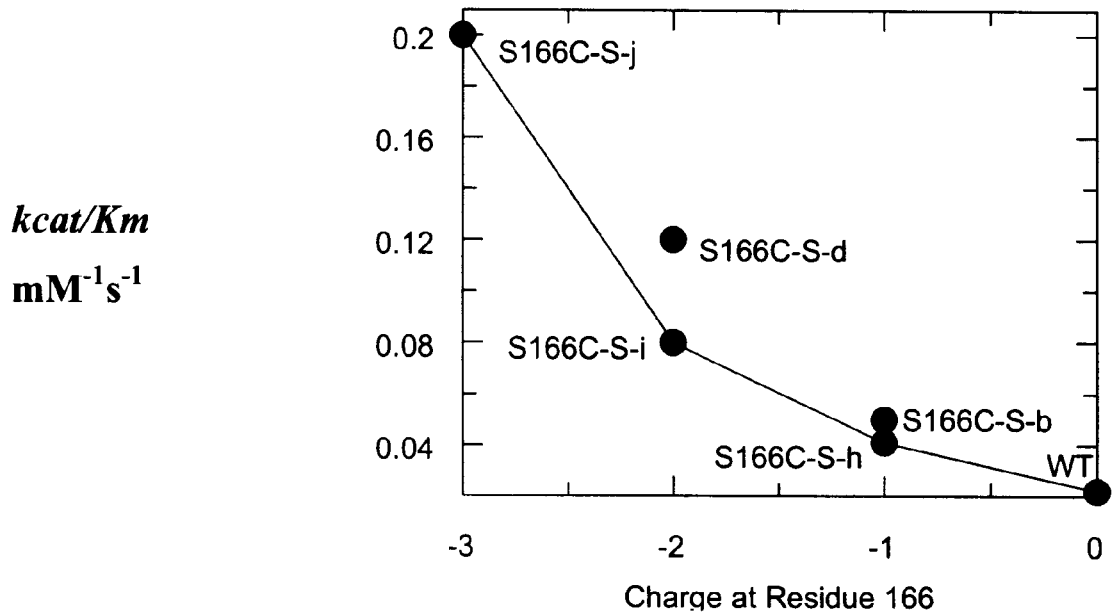
FIG. 11 shows a plot of side-chain negative charge on R at position 166 versus $k_{cat}/K_M$ with suc-AAPR-pNA. The points on the line are for the aliphatic series of carboxylated -R groups and the WT, Ser166.

Furthermore, these improvements correlate directly with the number of introduced negative charges, such that each additional negative charge introduced at position 166 causes an approximate doubling in $k_{cat}/K_M$ with the complementary charged suc-AAPR-pNA substrate (FIG. 11). This arithmetic improvement is interesting since it contrasts the previous observation that while remote noninteracting charged mutations are additive, multiple interacting adjacent charged mutations often are not additive. Rather, in most cases the empirically observed effects are lower than predicted from their individual sums.[80] This phenomenon is particularly problematic for charged mutations due to the long range effects of electrostatic interactions. For example, the sum of the transition state stabilization energy, $\Delta\Delta G\ddagger_T$, for the two single positively charged subtilisin mutations (D99K and E156K) over estimates the empirically observed effect of the double mutant, when assayed with an Arg $P_1$ containing substrate (Wells (1990) *Biochemistry* 29(37): 8509–8517). In contrast, in all cases the empirically determined $\Delta\Delta G\ddagger_T$ values for the aliphatic carbxylate series of mono- di- and tri- negatively charged side chains, of the S166C-S-h, -i, and -j CMMs exhibit an additive effect of additional charge $(\Delta\Delta G\ddagger_T$=RT $\ln[(k_{cat}/K_M)_{WT}/(k_{cat}/K_M)_{CMM}]$ S166C-S-b −0.49; S166C-S-d -1.00; S166C-S-h −0.37; S166C-S-i −0.76; S166C-S-j −1.31 (kcal mol$^{-1}$)). Thus, the CMM approach offers a convenient method to circumvent the problem of the attenuation of the augmenting effect of the introduction of additional charges by SDM by permitting the introduction of a larger local charge density.

Conversely, the adopted design strategy of introducing a complementary positive charge in the $S_1$ binding cleft by the CMM approach to improve $P_1$=Glu selectivity was based on mimicking the specificity determinants of the serine proteases pronase (Nienaber et al. (1993) *Biochemistry* 32(43): 11469–11475; Svendsen et al. (1991) *FEBS* 292(1): 165–167) and granzyme B (Smyth et al. (1996) *Leukoc. Biol.* 60: 555–562; Murphy et al. (1998) *Proteins: Structure: Function: and Genectics* 4: 190–204; Caputo et al. (1994) *Nature: Struct. Biol.* 1(6): 364–367), which exhibit a substrate preference for negatively charged $P_1$ residues, and whose $S_1$ pockets are lined with positively charged residues. The success of the current approach is apparent from the remarkable 19-fold increase in $k_{cat}/K_M$, with the suc-AAPE-pNA substrate displayed by S166C-S—$CH_2CH_2NH_3^+$ (-a). This enhancement is due to a combination of better binding, evident from the 2-fold lower $K_M$, and 8-fold higher $k_{cat}$ (Table 3, entries 23, 24). The induction of electrostatic complementarity was most unequivocally demonstrated by the 54-fold improvement in suc-AAPE-pNA to suc-AAPF-pNA substrate selectivity, with respect to $k_{cat}/K_M$, for S166C-S—$CH_2CH_2NH_3$+ (-a) compared to WT. Previously, the individual G166R and G166K subtilisin BPN' mutations, elicited 23- and 340-fold improvements in $k_{cat}/K_M$ for the suc-AAPE-pNA substrate. [12,14]However, it must be noted that the E156Q-G166K double mutant was much more receptive to Glu $P_1$ and exhibited a 1900-fold improvement compared to WT (Wells et al. (1987) *Proc. Nat. Acad. Sci. USA*, 84: 1219–1223). Interestingly, both the G166R and G166K mutants displayed even higher $k_{cat}/K_MS$ with the hydrophobic $P_1$ residue containing substrates suc-AAPN-pNA and suc-AAPM-pNA and even with the positively charged $P_1$ residue containing substrate suc-AAPK-pNA (Id.) While S166C-S—CH$_2$CH$_2$NH$_3^+$ (-a) still exhibits a 10-fold preference for suc-AAPF-pNA compared to suc-AAPE-pNA (Table 3, entry 2) the substrate screen (FIG. 10) shows that suc-AAPA-pNA and suc-AAPR-pNA are poorer substrates.

Since the S166C-S—CH$_2$CH$_2$NH$_3^+$ (-a) and suc-AAPE-pNA CMM-substrate pair exhibited the greatest k$_{cat}$/K$_M$ improvement relative to WT, at 19-fold (Table 3, entry 24), more detailed insights into the molecular basis of their interaction was sought using molecular modelling. Using the modelling approach reported previously (DeSantis et al. (1998) *Biochemistry* 37: 5968–5973), the product inhibitor, AAPE bound to WT-SBL and to the S166C-S—CH$_2$CH$_2$NH$_3^+$ (-a) CMM was minimized. Molecular modeling revealed that the minimized binding conformations of AAPE to both the WT and S166C-S—CH$_2$CH$_2$NH$_3^+$ enzymes are quite similar despite the 19-fold difference in k$_{cat}$/K$_M$. However, the ammonium moiety of the S166C-S—CH$_2$CH$_2$NH$_3^+$ CMM side chain is oriented toward the carboxylate of the glutamic acid P$_1$ residue, and although it is not quite within salt-bridge distance (N$^+$-to-$^-$OOC, 4.76 Å), this additional favorable coulombic interaction between the ammonium side chain of S166C-S—CH$_2$CH$_2$NH$_3^+$ and the carboxylate of the glutamic acid P$_1$ residue is deemed responsible for the observed 19-fold improvement in k$_{cat}$/K$_M$ for this CMM-substrate pair, compared to WT.

Conclusion

The overall data clearly provides an encouraging validation of the practical effectiveness of the CMM strategy for generating complementary electrostatic and steric enzyme-substrate interactions. For each of the Ala, Arg, and Glu P$_1$ residues at least one, and up to five, of the designed CMMs exhibit improved k$_{cat}$/K$_M$s compared to WT. The CMM approach is complementary to the SDM approach and also offers the additional opportunity for the introduction of multiply charged side-chains generating high charge densities at single active site locations. The beneficial effects of the introduction of a localized high charge density was demonstrated by the arithmetic increases in k$_{cat}$/K$_M$, with the suc-AAPR-pNA substrate, induced by incremental increases in the negative charge of the S$_1$ pocket.

Experimental

Sulfonatoethyl methanethiosulfonate (1a) and ethylamnmonium methanethiosulfonate (1b) were purchased from Toronto Research Chemicals (2 Brisbane Rd., Toronto, ON, Canada). Reagents 1c–1f (Berglund et al. (1997) *J. Am. Chem. Soc.* 119: 5265–5266) and 1h—1j were prepared as previously described. ES-MS data were acquired using a PE SCIEX API III Biomolecular mass spectrometer. The tetrapeptide substrates suc-AAPF/A/R/E-pNA were purchased from Bachem Bioscience Inc. (Torrance, Calif.). All buffer solutions were made up in deionized water.

Site-specific Chemical Modification

To 25 mg of a S166C mutant, purified as previously described (DeSantis et al. (1998) *Biochemistry* 37: 5968–5973; Stabile et al. (1996) *Bioorg. Med. Chem. Lett.* 6(21): 2501–2506) and stored flash frozen in CHES buffer (2.5 mL; 70 mM CHES, 5 mM MES, 2 mM CaCl$_2$, pH 9.5) at 20° C. was added one of the methanethiosulfonate reagents (1a–g) (100 μL of a 0.2 M solution) in a PEG (10,000) coated polypropylene test tube, and the mixture agitated in an end-over-end rotator. Blank reactions containing 100 μL of solvent instead of the reagent solution were run in parallel. Each of the modification reactions was monitored spectrophotometrically ($\epsilon_{410}$=8800 M$^{-1}$ cm$^{-1}$) (Bonneau et al. (1991) *J. Am. Chem. Soc.* 113: 1026–1030) on a Perkin Elmer Lambda 2 spectrophotometer, by specific activity measurements. After the reaction was quenched by dilution in MES buffer (5 mM MES, 2 mM CaCl$_2$, pH 6.5) at 0° C., the specific activity of the CMM (10 μL), was determined in buffer containing: 0.1 M TRIS pH 8.6, 0.005% Tween 80, and 1% DMSO, with the suc-AAPF-pNA substrate (1 mg/mL) at 25° C. The reaction was terminated when the addition of a further 100 μL of methanethiosulfonate solution effected no further change in specific activity, generally in 30 min. to 3 h. The reaction solution was purified on a disposable desalting column (Pharmacia Biotech PD-10, Sephadex G-25 M) pre-equilibrated with MES buffer (5 mM MES, 2 mM CaCl$_2$, pH 6.5) then dialyzed against 20 mM MES, 1 mM CaCl$_2$, pH 5.8 (3×1 L) at 4° C. and aliquoted into 0.5–1.5 mL volumes, flash frozen in liquid nitrogen and then stored at −20 C. Modified enzymes were analyzed by nondenaturing gradient (8–25%) gels at pH 4.2, run towards the cathode on the Pharmacia Phast-System,™ and appeared as one single band.

Electrospray Mass Stectrometry

Prior to ES-MS analysis, CMMs were purified by FPLC (BioRad, Biologic System) on a Source 15 RPC matrix (17-0727-20 from Pharmacia) with 5% acetonitrile, 0.01% TFA as the running buffer and eluted with 80% acetonitrile, 0.01% TFA in a one step gradient. Mass: WT: Calc. 26698, Found 26694. S166C-S-a: Calc. 26714, Found 26708 S166C-S-b: Calc. 26853, Found 26851. S166C-S-c: Calc. 26836, Found 26832. S166C-S-d; Calc. 26924, Found 26928. [70]S166C-S-e: Calc. 26886, Found 26890. S166C-S-f: Calc. 26842, Found 26844. S166C-S-g: Calc. 27128, Found 27123. S166C-S-h; Calc. 26846, Found 26846.[7] S166C-S-i; Calc. 26890, Found 26894.[70] S166C-S-i; Calc. 26934, Found 26939.

Regeneration of Unmodified Enzyme by Treatment with β-mercaptoethanol

To a solution of CMM (2.0 mg) in 250 μL of CHES-buffer (70 mM CHES, 5 mM MES, 2 mM CaCl$_2$, pH 9.5) was added 10 μL of a solution of β-mercaptoethanol (1 M in 95% EtOH ). The reaction was monitored by specific activity measurements.

Free Thiol Titration

The free thiol content of S166C CMMs, was determined spectrophotometrically by titration with Ellman's reagent ($\epsilon_{412}$=13600 M$^{-1}$ cm$^{-1}$)[87] in phosphate buffer 0.25 M, pH 8.0.

Active Site Titrations

The active enzyme concentration was determined as previously described[71] by monitoring fluoride release upon enzyme reaction with phenylmethanesulfonyl fluoride (Aldrich Chemical Co. Inc. ) as measured by a fluoride ion sensitive electrode (Orion Research 96-09). The active enzyme concentration determined in this way was used to calculate kinetic parameters for each CMM.

Kinetic Measurements

Michaelis-Menten constants were measured at 25° C. by curve fitting (GraFit® 3.03) of the initial rate data determined at eight concentrations (0.125 mM–8.0 mM) of the suc-AAPX-pNA substrate in pH 8.6 0.1 M Tris-HCl buffer containing 0.005% Tween 80, 1% DMSO ($\epsilon_{410}$=8800 M$^{-1}$ cm$^{-1}$).

Molecular Modeling

The X-ray structure of subtilisin *Bacillus lentus*[59] was used as the starting point for calculations on the wild type and chemically modified mutant enzymes. The enzyme setup was performed with Insight II.[88] To create initial coordinates for the minimization, hydrogens were added at the pH used for kinetic measurements. This protonated all Lys and Arg residues and the N-terminus and deprotonated all Glu and Asp residues and the C-terminus. In addition, the active site His64 was protonated. The model system with the Ala-Ala-Pro-Phe (from crystal structure) (Knapp et al. *Brookhaven Database Entry 1JEA*, [without Ala-Ala-Pro-Phe]) product inhibitor bound in the $S_1$–$S_4$ pocket was solvated with a 5 Å layer of water molecules giving a total number of water molecules of 1143 in this system. The overall charge of the enzyme-inhibitor complex resulting from this setup was +4 for the WT enzyme. Energy simulations were performed with the Discover program (*Discover* [Biosym Technologies: Inc. San Diego: Cailf.: USA]), on a Silicon Graphics Iris Indigo computer, using the consistent valence force field function (CVFF). A non-bonded cutoff distance of 18 Å with a switching distance of 2 Å was employed. The non-bonded pair list was updated every 20 cycles and a dielectric constant of 1 was used in all calculations. The WT enzyme was minimized in stages, with initially only the water molecules being allowed to move, then the water molecules and the amino acid side chains, and then the entire enzyme. The mutated and chemically modified enzymes were generated using the Builder module of Insight. Then the amino acid side chains within a 10 Å radius of the a-carbon of the mutated residue were minimized while all other residues were constrained, then all of the atoms within a 10 Å shell were minimized, followed by minimization of the whole system. To examine the effect of a different $P_1$ residue (Glu), the Phe to Glu mutation of the product inhibitor was constructed using insightII, and then this structure was minimized as above.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A modified subtilisin enzyme, comprising a subtilisin wherein an amino acid residue selected from the group consisting of residue 62, residue 96, residue 104, residue 107, residue 156, residue 166, residue 189, residue 209, residue 217 and residue 222 is replaced by a cysteine residue, wherein the cysteine residue is modified by replacing the thiol hydrogen in said cysteine residue with a substituent group providing a thiol side chain comprising a multiply charged moiety, and wherein said amino acid residue is numbered according to its equivalent in the amino acid sequence of *Bacillus amyloliquefaciens* subtilisin BPN' (SEQ ID NO: 2).

2. The modified subtilisin enzyme of claim 1, wherein the multiply charged moiety is negatively charged.

3. The modified subtilisin enzyme of claim 2, wherein the multiply charged moiety is selected from the group consisting of 3,5-dicarboxybenzyl thiol, 3,3-dicarboxybutyl thiol, and 3,3,4-tricarboxybutyl thiol.

4. The modified subtilisin enzyme of claim 2, wherein the multiply charged moiety is a dendrimer or a polymer.

5. The modified subtilisin enzyme of claim 1, wherein the multiply charged moiety is positively charged.

6. The modified subtilisin enzyme of claim 5, wherein the multiply charged moiety is selected from the group consisting of 4,4-bis(aminomethyl)-3-oxo-hexyl thiol, and 2,2-bis(aminomethyl)-3-aminopropyl thiol.

7. The modified subtilisin enzyme of claim 5, wherein the multiply charged moiety is a dendrimer or a polymer.

8. The modified subtilisin of claim 1, wherein said amino acid residue is selected from the group consisting of residue 62, residue 156, residue 166 and residue 217.

9. The modified subtilisin enzyme of claim 4, wherein said dendrimer or polymer comprises X and Y, wherein X and Y are individually the same or different and are independently selected from the group consisting of sulfonatoethyl thiol and 4-carboxybutyl thiol.

10. The modified subtilisin enzyme of claim 7, wherein said dendrimer or polymer comprises X and Y, wherein X and Y are individually the same or different and are independently selected from the group consisting of aminoethyl thiol group and 2-(trimethylammoniun)ethyl thiol.

11. The modified subtilisin enzyme of claim 1, wherein said subtilisin is subtilisin *Bacillus lentus* (SEQ ID NO: 1).

12. The modified subtilisin enzyme of claim 11, wherein the multiply charged moiety is negatively charged.

13. The modified subtilisin enzyme of claim 12, wherein the multiply charged moiety is selected from the group consisting of 3,5-dicarboxybenzyl thiol, 3,3-dicarboxybutyl thiol, and 3,3,4-tricarboxybutyl thiol.

14. The modified subtilisin enzyme of claim 12, wherein the multiply charged moiety is a dendrimer or a polymer.

15. The modified subtilisin enzyme of claim 11, wherein the multiply charged moiety is positively charged.

16. The modified subtilisin enzyme of claim 15, wherein the multiply charged moiety is selected from the group consisting of 4,4-bis(aminomethyl)-3-oxo-hexyl thiol, and 2,2-bis(aminomethyl)-3-aminopropyl thiol.

17. The modified subtilisin enzyme of claim 15, wherein the multiply charged moiety is a dendrimer or a polymer.

18. The modified subtilisin enzyme of claim 11, wherein said amino acid residue is selected from the group consisting of residue 62, residue 156, residue 166 and residue 217.

19. The modified subtilisin enzyme of claim 14, wherein said dendrimer or polymer comprises X and Y, wherein X and Y are individually the same or different and are independently selected from the group consisting of sulfonatoethyl thiol and 4-carboxybutyl thiol.

20. The modified subtilisin enzyme of claim 17, wherein said dendrimer or polymer comprises X and Y, wherein X and Y are individually the same or different and are independently selected from the group consisting of aminoethyl thiol group and 2-(trimethylammonium)ethyl thiol.

21. A composition comprising the modified subtilisin enzyme of any one of claims 1 through 10 or 12 through 17 and a detergent.

* * * * *

SEQUENCE LISTING

```
<160> NUMBER OF SEQ ID NOS: 2

<210> SEQ ID NO 1
<211> LENGTH: 269
<212> TYPE: PRT
<213> ORGANISM: Bacillus lentus
<220> FEATURE:
<223> OTHER INFORMATION: Subtilisin SBL

<400> SEQUENCE: 1

Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
                100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
```

```
              210                 215                 220
Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                    245                 250                 255

Tyr Gly Ser Gly Leu Val Asn Ala Glu Ala Ala Thr Arg
                260                 265

<210> SEQ ID NO 2
<211> LENGTH: 275
<212> TYPE: PRT
<213> ORGANISM: Bacillus amyloliquefaciens
<220> FEATURE:
<223> OTHER INFORMATION: Subtilisin BPN'

<400> SEQUENCE: 2

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Lys Val Ala Gly Gly Ala
            35                  40                  45

Ser Met Val Pro Ser Glu Thr Asn Pro Phe Gln Asp Asn Asn Ser His
50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
            115                 120                 125

Pro Ser Gly Ser Ala Ala Leu Lys Ala Ala Val Asp Lys Ala Val Ala
130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
            195                 200                 205

Leu Pro Gly Asn Lys Tyr Gly Ala Tyr Asn Gly Thr Ser Met Ala Ser
210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
            275
```